US010912786B2

(12) United States Patent
Barany et al.

(10) Patent No.: US 10,912,786 B2
(45) Date of Patent: Feb. 9, 2021

(54) SILYL MONOMERS CAPABLE OF MULTIMERIZING IN AN AQUEOUS SOLUTION, AND METHODS OF USING SAME

(71) Applicants: Cornell University, Ithaca, NY (US); Purdue Research Foundation, West Lafayette, IN (US)

(72) Inventors: Francis Barany, New York, NY (US); Maneesh Pingle, New York, NY (US); Donald E. Bergstrom, West Lafayette, IN (US); Sarah F. Giardina, New York, NY (US); Lee Daniel Arnold, Mt. Sinai, NY (US)

(73) Assignees: Cornell University, Ithaca, NY (US); Purdue Research Foundation, West Lafayette, IN (US)

( * ) Notice: Subject to any disclaimer, the term of this patent is extended or adjusted under 35 U.S.C. 154(b) by 121 days.

(21) Appl. No.: 15/247,539

(22) Filed: Aug. 25, 2016

(65) Prior Publication Data

US 2017/0080001 A1 Mar. 23, 2017

Related U.S. Application Data

(63) Continuation of application No. 14/110,060, filed as application No. PCT/US2012/032813 on Apr. 9, 2012, now abandoned.

(60) Provisional application No. 61/473,091, filed on Apr. 7, 2011.

(51) Int. Cl.
*A61K 31/695* (2006.01)
*A61K 47/55* (2017.01)
*C07F 7/10* (2006.01)

(52) U.S. Cl.
CPC ............ *A61K 31/695* (2013.01); *A61K 47/55* (2017.08); *C07F 7/10* (2013.01)

(58) Field of Classification Search
CPC .................................................. A61K 31/395
See application file for complete search history.

(56) References Cited

U.S. PATENT DOCUMENTS

| | | | | |
|---|---|---|---|---|
| 5,624,802 A * | 4/1997 | Urdea | ..................... | C07H 19/06 435/6.11 |
| 6,222,094 B1 * | 4/2001 | Hansson | ............ | A01K 67/0278 526/72 |
| 6,326,011 B1 | 12/2001 | Miyazawa et al. | | |
| 7,511,139 B2 | 3/2009 | Zhou et al. | | |
| 7,807,699 B2 * | 10/2010 | Hanson | ................ | C07D 207/16 514/359 |
| 8,222,291 B2 * | 7/2012 | Hanson | ................ | C07D 207/16 514/408 |
| 8,586,542 B2 * | 11/2013 | Hanson | ................ | C07D 207/16 514/18.9 |
| 2002/0150890 A1 | 10/2002 | Nakayama et al. | | |
| 2004/0241748 A1 | 12/2004 | Ault-Riche et al. | | |
| 2004/0265902 A1 | 12/2004 | Fricker et al. | | |
| 2008/0255425 A1 | 10/2008 | Voegele et al. | | |
| 2009/0149399 A1 | 6/2009 | Tung | | |
| 2010/0081792 A1 | 4/2010 | Grant et al. | | |
| 2010/0159446 A1 | 6/2010 | Haff et al. | | |
| 2014/0161729 A1 | 6/2014 | Barany et al. | | |
| 2014/0194383 A1 | 7/2014 | Barany et al. | | |

FOREIGN PATENT DOCUMENTS

| | | | | |
|---|---|---|---|---|
| JP | H08-302016 | | 11/1996 | |
| WO | 98/54255 A1 | | 3/1998 | |
| WO | 2000002896 A1 | | 1/2000 | |
| WO | 2005118585 A1 | | 12/2005 | |
| WO | 2008/131921 A1 | | 11/2008 | |
| WO | 2009/018003 A2 | | 2/2009 | |
| WO | 2009/020589 A1 | | 2/2009 | |
| WO | 2009126290 A1 | | 10/2009 | |
| WO | 2011/043817 A1 | | 4/2011 | |
| WO | 2012154213 A1 | | 11/2011 | |
| WO | 2013058824 A1 | | 4/2013 | |
| WO | WO-2015081280 A1 * | | 6/2015 | ......... A61K 31/5517 |

OTHER PUBLICATIONS

Venkatesh et al., J. Pharm. Sci. 89, 145-54 (2000) (p. 146, left column).*
Elrod, Am J Respir Crit Care Med vol. 156. pp. 375-381, 1997.*
Williamon, Biochem. J. (1994) 297, 249-260.*
Medzihradszky, Anal. Chem. 2014, 86, 8906-8909.*
Pan, Rapid Commun. Mass Spectrom. 2008; 22: 3555-3560.*
Dorwald F. A. Side Reactions in Organic Synthesis, 2005, Wiley: VCH, Weinheim p. IX of Preface p. 1-15.*
Vidal, Biochemistry 2004, 43, 7336-7344 Biochemistry 2004, 43, 7336-7344).*
Hadden Anticancer Agents Med Chem. Oct. 2008 ; 8(7): 807-816.*
Liang, Bioorganic & Medicinal Chemistry Letters 22 (2012) 3370-3376.*
Levell, Bioorganic & Medicinal Chemistry 13 (2005) 2859-2872.*

(Continued)

*Primary Examiner* — Noble E Jarrell
(74) *Attorney, Agent, or Firm* — Troutman Pepper Hamilton Sanders LLP

(57) ABSTRACT

Described herein are silyl monomers capable of forming a biologically useful multimer when in contact with one, two, three or more other monomers in an aqueous media. Such multimer forming associations of monomers may be promoted by the proximal binding of the monomers to their target biomolecule(s). In one aspect, such monomers may be capable of binding to another monomer in an aqueous media (e.g. in vivo) to form a multimer, (e.g. a dimer). Contemplated monomers may include a ligand moiety, a linker element, and a connector element that joins the ligand moiety and the linker element. In an aqueous media, such contemplated monomers may join together via each linker element and may thus be capable of modulating one or more biomolecules substantially simultaneously, e.g., modulate two or more binding domains on a protein or on different proteins.

17 Claims, 4 Drawing Sheets

Specification includes a Sequence Listing.

(56) References Cited

OTHER PUBLICATIONS

Hopkins, Bioorganic & Medicinal Chemistry Letters 15 (2005) 2734-2737.*
Liang, Med. Chem. Commun., 2011, 2, 794-799.*
Krokowski, Cell Cycle 10:16, 2691-2702, 2011.*
Venkatesh J. Pharm. Sci. 89, 145-54 (2000).*
Wright et al., Science, 10.1126/science.aag1465 (2016.*
Bunyapaiboonsri et al., "Generation of Bis-Cationic Heterocyclic Inhibitors of Bacillus subtills HPr Kinase/Phosphatase from a Ditopic Dynamic Combinatorial Library," J. Med. Chem. 46:5803-11 (2003).
Burke et al., "Development and Application of Fluorescence Polarization Assays in Drug Discovery," Combinatorial Chem. High Throughput Screening 6:183-94 (2003).
Delord et al., "Novel C-Organosilicon Derivatives as Leads for Reverse-Transcriptase-Mediated Anti-HIV-1 Activity," Eur. J. Med. Chem. 31(2):111-22 (1996).
European Patent Application No. 12842368, Supplementary European Search Report (dated Aug. 8, 2014).
European Patent Application No. 12842488, Supplementary European Search Report (dated Sep. 4, 2014).
Lafay et al., "Synthesis of Novel C-Organosilicon Derivatives, Potential Inhibitors of Hiv Reverse Transcription," Phosphorus Sulfur Silicon Relat. Elem. 102(1-4):155-68 (1995).
PCT/US2012/000198, International Search Report and Written Opinion (dated Oct. 1, 2012).
PCT/US2012/032809, International Search Report and Written Opinion (dated Oct. 1, 2012).
PCT/US2012/032813, International Search Report and Written Opinion (dated Sep. 24, 2012).
Shin et al., "Assembling Ligands In Situ Using Bioorthogonal Boronate Ester Synthesis," Chem. Biol. 17:1171-76 (2010).
Trinquet et al., "Fluorescence Technologies for the Investigation of Chemical Libraries," Mol. Biosyst. 2:380-87 (2006).
Wang et al., "Synthesis, Curing Behavior and Properties of Siloxane and Imide-Containing Tetrafunctional Epoxy," J. Polymer Res. 15(1):1-9 (2008).
Anthony R. West, Solid-State Chemistry and Its Applications (1984).
Molnar et al, "New Silicon Compounds as Resistance Modifiers Against Multidrug-Resistant Cancer Cells," Anticancer Res. 24:865-72 (2004).
Pohl & Osterholtz, "Kinetics and Mechanism of Aqueous Hydrolysis and Condensation of Alkyltrialkoxysilanes," in Molecular Characterization of Composite Interfaces 157-70 (H. Ishida & G. Kumar eds. 1985).
Tacke et al., "The SiOH-Containing Alpha-Amino Acid HOMe2SiCH2CH(NH2)COOH and Its Immobilization on Silica via an Si—O—Si Linkage," Organometallics 24:1780-83 (2005).
Tokuda et al., "Effects of Two Disiloxanes ALIS-409 and ALIS-421 on Chemoprevention in Model Experiments," Anticancer Res. 33:2021-28 (2013).

* cited by examiner

SEQUENCE LISTING

```
<160> NUMBER OF SEQ ID NOS: 9

<210> SEQ ID NO 1
<211> LENGTH: 13
<212> TYPE: PRT
<213> ORGANISM: Artificial
<220> FEATURE:
<223> OTHER INFORMATION: Peptide inhibitor of ERK activation
<220> FEATURE:
<221> NAME/KEY: MISC_FEATURE
<222> LOCATION: (1)..(1)
<223> OTHER INFORMATION: Residue 1 is stearated

<400> SEQUENCE: 1

Met Pro Lys Lys Lys Pro Thr Pro Ile Gln Leu Asn Pro
1               5                   10

<210> SEQ ID NO 2
<211> LENGTH: 26
<212> TYPE: PRT
<213> ORGANISM: Artificial
<220> FEATURE:
<223> OTHER INFORMATION: Peptide inhibitor of ERK activation

<400> SEQUENCE: 2
```

```
Gly Tyr Gly Arg Lys Lys Arg Arg Gln Arg Arg Gly Met Pro Lys
1               5                   10                  15

Lys Lys Pro Thr Pro Ile Gln Leu Asn Pro
            20                  25

<210> SEQ ID NO 3
<211> LENGTH: 5
<212> TYPE: PRT
<213> ORGANISM: Artificial
<220> FEATURE:
<223> OTHER INFORMATION: Peptide inhibitor of B-Amyloid

<400> SEQUENCE: 3

Lys Leu Val Phe Phe
1               5

<210> SEQ ID NO 4
<211> LENGTH: 5
<212> TYPE: PRT
<213> ORGANISM: Artificial
<220> FEATURE:
<223> OTHER INFORMATION: Peptide inhibitor of B-Amyloid

<400> SEQUENCE: 4

Leu Val Phe Phe Ala
1               5

<210> SEQ ID NO 5
<211> LENGTH: 4
<212> TYPE: PRT
<213> ORGANISM: Artificial
<220> FEATURE:
<223> OTHER INFORMATION: Peptide inhibitor of SH2 domain
<220> FEATURE:
<221> NAME/KEY: MISC_FEATURE
<222> LOCATION: (3)..(3)
<223> OTHER INFORMATION: Xaa is Aib

<400> SEQUENCE: 5

Glu Tyr Xaa Asn
1

<210> SEQ ID NO 6
<211> LENGTH: 6
<212> TYPE: PRT
<213> ORGANISM: Artificial
<220> FEATURE:
<223> OTHER INFORMATION: Peptide inhibitor of SH2 domain
<220> FEATURE:
<221> NAME/KEY: MISC_FEATURE
<222> LOCATION: (1)..(1)
<223> OTHER INFORMATION: residue 1 is acetylated
<220> FEATURE:
<221> NAME/KEY: MISC_FEATURE
<222> LOCATION: (2)..(2)
<223> OTHER INFORMATION: Xaa is phosphotyrosine

<400> SEQUENCE: 6

Ser Xaa Val Asn Val Gln
1               5

<210> SEQ ID NO 7
<211> LENGTH: 6
<212> TYPE: PRT
<213> ORGANISM: Artificial
<220> FEATURE:
<223> OTHER INFORMATION: Peptide inhibitor of phosphotyrosine-binding
      domains
```

```
<220> FEATURE:
<221> NAME/KEY: MISC_FEATURE
<222> LOCATION: (6)..(6)
<223> OTHER INFORMATION: Xaa is phosphotyrosine,
      phosphonomethylphenylalanine,
      difluorophosphonomethylphenylalanine, 0-malonyltyrosine, or 0-
      fluoromalonyltyrosine

<400> SEQUENCE: 7

Leu Ser Asn Pro Thr Xaa
1               5

<210> SEQ ID NO 8
<211> LENGTH: 9
<212> TYPE: PRT
<213> ORGANISM: Artificial
<220> FEATURE:
<223> OTHER INFORMATION: Peptide inhibitor of phosphotyrosine-binding
      domains
<220> FEATURE:
<221> NAME/KEY: MISC_FEATURE
<222> LOCATION: (9)..(9)
<223> OTHER INFORMATION: Xaa is phosphotyrosine,
      phosphonomethylphenylalanine,
      difluorophosphonomethylphenylalanine, 0-malonyltyrosine, or 0-
      fluoromalonyltyrosine

<400> SEQUENCE: 8

Leu Tyr Ala Ser Ser Asn Pro Ala Xaa
1               5

<210> SEQ ID NO 9
<211> LENGTH: 10
<212> TYPE: PRT
<213> ORGANISM: Artificial
<220> FEATURE:
<223> OTHER INFORMATION: Peptide inhibitor of SH3 domain

<400> SEQUENCE: 9

Val Pro Pro Pro Val Pro Pro Arg Arg Arg
1               5                   10
```

SILYL MONOMERS CAPABLE OF MULTIMERIZING IN AN AQUEOUS SOLUTION, AND METHODS OF USING SAME

CROSS-REFERENCE TO RELATED APPLICATIONS

This application is a continuation of U.S. patent application Ser. No. 14/110,060, filed Apr. 9, 2012, which is a national stage application, submitted under 35 U.S.C. § 371, of PCT Application No. PCT/US2012/032813, filed Apr. 9, 2012, which claims priority to U.S. Provisional Application No. 61/473,091, filed Apr. 7, 2011, each of which is hereby incorporated by reference in its entirety.

BACKGROUND

Current drug design and drug therapies have not addressed the urgent need for therapies that interact with extended areas or multiple domains of biomolecules such as proteins. For example, there is an urgent need for therapies that are capable of, e.g., modulating protein-protein interactions, e.g., by interacting, simultaneously, with multiple domains on a single protein, or a domain on one protein along with a domain on another protein. There is also an urgent need for such therapies that modulate fusion proteins, such as those that occur in cancer.

For example, signaling pathways are used by cells to generate biological responses to external or internal stimuli. A few thousand gene products control both ontogeny/development of higher organisms and sophisticated behavior by their many different cell types. These gene products can work in different combinations to achieve their goals and often do so through protein-protein interactions. Such proteins possess modular protein domains that recognize, bind, and/or modify certain motifs. Protein-protein and protein-nucleic acid recognition often function through protein interactions domains, for example, such as the SH2, SH3, and PDZ domains. These protein-interaction domains may represent a meaningful area for developing targeted therapies. Other macromolecular interactions that may serve as potential targets for effective therapies include protein-nucleic acid interactions, protein-carbohydrate interactions, and protein-lipid interactions.

Current drug design and drug therapy approaches do not address this urgent need to find drugs that interfere with intracellular protein-protein interactions or protein signaling. Although antibodies and other biological therapeutic agents may have sufficient specificity to distinguish among closely related protein surfaces, factors such as their high molecular weight prevent oral administration and uptake of the antibodies. Conversely, orally active pharmaceuticals are generally too small to disrupt protein-protein surface interactions, which can be much larger than the orally active pharmaceuticals. Further, previous attempts to link, e.g., two pharmacophores that each interact with e.g. different protein domains have focused on large covalently linked compounds assembled in organic solvents. These assemblies typically have a molecular weight too large for oral administration or effective cellular and tissue permeation.

SUMMARY

Described herein are monomers capable of forming a biologically useful multimer when in contact with one, two, three or more other monomers in an aqueous media. In one aspect, such monomers may be capable of binding to another monomer in an aqueous media (e.g. in vivo) to form a multimer, (e.g. a dimer). Contemplated monomers may include a ligand moiety (e.g. a ligand or pharmacophore for the target biomolecule), a linker element, and a connector element that joins the ligand moiety and the linker element. In an aqueous media, such contemplated monomers may join together via each linker element and may thus be capable of modulating one or more biomolecules substantially simultaneously, e.g., modulate two or more binding domains on a protein or on different proteins.

In one aspect, a first silyl monomer capable of forming a biologically useful multimer when in contact with one, two, three or more second silyl monomers in an aqueous media is provided. The first and second silyl monomer are represented by the formula:

$$X^3-Y^3-Z^3 \quad \text{(Formula III)}$$

and pharmaceutically acceptable salts, stereoisomers, metabolites and hydrates thereof, wherein
$X^3$ is a first ligand moiety capable of binding to and modulating a first target biomolecule;
$Y^3$ is absent or is a connector moiety covalently bound to $X^3$ and $Z^3$;
$Z^3$ is independently selected from the group consisting of:

a)

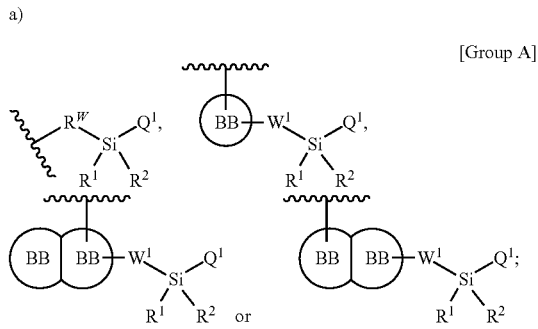

[Group A]

wherein
$R^W$ is selected from the group consisting of a bond, $-C_{1-4}$alkyl-, $-O-C_{1-4}$alkyl-, $-N(R^a)-C_{1-4}$alkyl-, $-C_{1-4}$alkyl-C(O)-, $-C(O)C_{1-4}$alkyl-, $-C_{1-4}$alkyl-O-C(O)-, $-C(O)-O-C_{1-4}$alkyl-, $-NR^a-C(O)-$, $-C_{2-6}$alkenyl-, $-C_{2-6}$alkynyl-, $-C_{3-6}$cycloalkyl-, -phenyl-, -heteroaryl-, and -heterocyclic-; wherein $C_{1-4}$alkyl, $R^a$, $R^b$, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, $-C(O)C_{1-4}$alkyl, $-C(O)-O-C_{1-4}$alkyl, $-C(O)-NR^aR^b$, halogen, cyano, hydroxyl, cycloalkyl, heterocyclic, phenyl, heteroaryl, $R^a$ and $R^b$, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;
$W^1$, independently for each occurrence, is (a) absent; or (b) selected from the group consisting of $-C_{1-4}$alkyl-, $-O-C_{1-4}$alkyl-, $-C_{1-4}$alkyl-C(O)-, $-C(O)-C_{1-4}$alkyl-, $-N(R^a)-C_{1-4}$alkyl-, $-C_{1-4}$alkyl-O-C(O)-, $-C(O)-O-C_{1-4}$alkyl-, $-NR^a-C(O)-$, $-C_{2-6}$alkenyl-, $-C_{2-6}$alkynyl-, $-C_{3-6}$cycloalkyl-, -phenyl-, -heteroaryl-, and heterocyclic; wherein $C_{1-4}$alkyl, $C_{2-6}$alkenyl, $C_{2-6}$alkynyl, $C_{3-6}$cycloalkyl, R', phenyl, heterocyclic, and heteroaryl are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

R' is independently selected, for each occurrence, from the group consisting of hydrogen, substituted or unsubstituted aliphatic, and substituted or unsubstituted heteroaliphatic;

Q' is independently selected, for each occurrence, from the group consisting of —NHR', —N(R')$_2$, —NR$^a$R$^b$, —O—Si(R')$_3$, —O—SiR$^a$R$^b$R', —SH, —OH, —O—$C_{1-6}$alkyl, —S—$C_{1-6}$alkyl, —O-aryl, —S-aryl, heteroaryl, —O-heteroaryl, —S-heteroaryl, halogen and —O—$C_{1-6}$alkyl-NR$^a$R$^b$;

R$^a$ and R$^b$ are independently selected, for each occurrence, from the group consisting of hydrogen, $C_{1-4}$alkyl, —O—$C_{1-4}$alkyl and —NH—$C_{1-4}$alkyl; wherein $C_{1-4}$alkyl may be optionally substituted by one or more substituents selected from the group consisting of halogen, cyano, oxo and hydroxyl; or R$^a$ and R$^b$, together with the nitrogen to which they are attached, may form a 4-7 membered heterocyclic ring, which may have one or more additional heteroatoms selected from O, S, or N; wherein the 4-7 membered heterocyclic ring may be optionally substituted by one or more substituents selected from the group consisting of halogen, cyano, oxo, amino and hydroxyl;

R$^1$ and R$^2$ are selected independently, for each occurrence, from the group consisting of —OH, $C_{1-6}$alkyl, —O—$C_{1-6}$alkyl, $C_{2-6}$alkenyl, $C_{3-6}$cycloalkyl, —$C_{1-6}$alkyl-NR$^a$R$^b$, phenyl and heteroaryl; wherein $C_{1-6}$alkyl, $C_{2-6}$alkenyl, $C_{3-6}$cycloalkyl, R$^a$, R$^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or R$^1$ and R$^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

BB, independently for each occurrence, is a 4-7-membered cycloalkyl, heterocyclic, aryl, or heteroaryl moiety, wherein the cycloalkyl, heterocyclic, aryl, or heteroaryl moiety is optionally substituted with one, two, three or more groups represented by R$^{BB}$; wherein R$^1$, independently for each occurrence, may be optionally bonded to BB;

each R$^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —$C_{1-4}$alkyl, —O—$C_{1-4}$alkyl, —N(R$^a$)—$C_{1-4}$alkyl, —C(O)$C_{1-4}$alkyl, —C(O)—O—$C_{1-4}$alkyl, —C(O)—NR$^a$R$^b$, —$C_{2-6}$alkenyl, —$C_{2-6}$alkynyl, —$C_{3-6}$cycloalkyl), heterocyclic, phenyl, phenoxy, heteroaryl, —$C_{1-4}$alkylene-phenyl, —$C_{1-4}$alkylene-heteroaryl, —$C_{1-4}$alkylene-heterocyclyl, —$C_{2-6}$alkenylene-phenyl, —$C_{2-6}$alkenylene-heteroaryl, —$C_{2-6}$alkenylene-heterocyclyl, —$C_{2-6}$alkynyl-phenyl, —$C_{2-6}$alkynyl-heteroaryl, —$C_{2-6}$alkynyl-heterocyclyl; wherein $C_{1-4}$alkyl, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—NR$^a$R$^b$, halogen, cyano, hydroxyl, cycloalkyl, heterocyclic, phenyl, or heteroaryl, and R$^a$ and R$^b$ are defined herein; or two R$^{BB}$ together with the atoms to which they are attached form a fused 5- or 6-membered cycloalkyl or heterocyclic bicyclic ring system; and b)

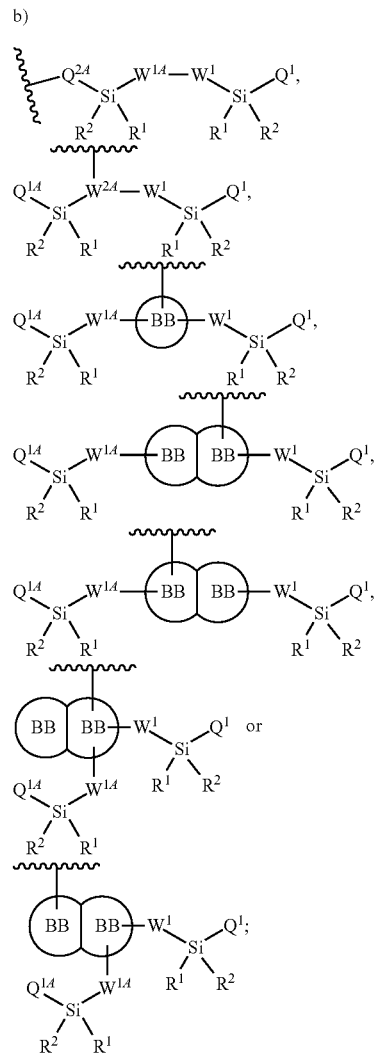

wherein
Q$^{2A}$ is selected from the group consisting of a bond, —O—$C_{1-6}$alkyl-, —N(R')—$C_{1-6}$alkyl-, and —S—$C_{1-6}$alkyl-;

W$^1$, independently for each occurrence, is (a) absent; or (b) selected from the group consisting of —$C_{1-4}$alkyl-, —O—$C_{1-4}$alkyl-, —N(R$^a$)—$C_{1-4}$alkyl-, —$C_{1-4}$alkyl-C(O)—, —C(O)$C_{1-4}$alkyl-, —$C_{1-4}$alkyl-O—C(O)—, —C(O)—O—$C_{1-4}$alkyl-, —NR'—C(O)—, —$C_{2-6}$alkenyl-, —$C_{2-6}$alkynyl-, —$C_{3-6}$cycloalkyl-, -phenyl-, and -heteroaryl-; wherein $C_{1-4}$alkyl, $C_{2-6}$alkenyl, $C_{2-6}$alkynyl, $C_{3-6}$cycloalkyl, R', R$^a$ phenyl and heteroaryl may be optionally substituted independently, for each occurrence, with one, two, three or more substituents selected from the group consisting of $C_{1-4}$alkyl, $C_{1-4}$alkoxy, —C(O)$C_{1-6}$alkyl, —C(O)—O—$C_{1-4}$alkyl, halogen, hydroxyl, nitro, carbamate, carbonate and cyano;

$W^{1A}$, independently for each occurrence, is (a) absent; or (b) selected from the group consisting of —$C_{1-4}$alkyl-, —$C_{1-4}$alkyl-O—, —$C_{1-4}$alkyl-N($R^a$)—, —$C_{1-4}$alkyl-C(O)—, —C(O)$C_{1-4}$alkyl-, —$C_{1-4}$alkyl-O—C(O)—, —C(O)—O—$C_{1-4}$alkyl-, —C(O)—NR'—, —$C_{2-6}$alkenyl-, —$C_{2-6}$alkynyl-, —$C_{3-6}$cycloalkyl-, -phenyl-, and -heteroaryl-; wherein $C_{1-4}$alkyl, $C_{2-6}$alkenyl, $C_{2-6}$alkynyl, $C_{3-6}$cycloalkyl, R', $R^a$ phenyl and heteroaryl may be optionally substituted independently, for each occurrence, with one, two, three or more substituents selected from the group consisting of $C_{1-4}$alkyl, $C_{1-4}$alkoxy, —C(O)$C_{1-6}$alkyl, —C(O)—O—$C_{1-4}$alkyl, halogen, hydroxyl, nitro, carbamate, carbonate and cyano;

R' is independently selected, for each occurrence, from the group consisting of hydrogen, substituted or unsubstituted aliphatic, and substituted or unsubstituted heteroaliphatic;

$Q^1$ and $Q^{1A}$ are independently selected, for each occurrence, from the group consisting of —NHR', —$NR^aR^b$, —O—Si(R')$_3$, —O—Si$R^aR^b$R', —SH, —OH, —O—$C_{1-6}$alkyl, —S—$C_{1-6}$alkyl, —O-aryl, —S-aryl, heteroaryl, —O-heteroaryl, —S-heteroaryl, halogen and —O—$C_{1-6}$alkyl-$NR^aR^b$;

$R^a$ and $R^b$ are independently selected, for each occurrence, from the group consisting of hydrogen and $C_{1-4}$alkyl; wherein $C_{1-4}$alkyl may be optionally substituted by one or more substituents selected from the group consisting of halogen, cyano, oxo and hydroxyl; or $R^a$ and $R^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl;

$R^1$ and $R^2$ are selected independently, for each occurrence, from the group consisting of —OH, $C_{1-6}$alkyl, —O—$C_{1-6}$alkyl, $C_{2-6}$alkenyl, $C_{3-6}$cycloalkyl, —$C_{1-6}$alkyl-$NR^aR^b$, phenyl and heteroaryl; wherein $C_{1-6}$alkyl, $C_{2-6}$alkenyl, $C_{3-6}$cycloalkyl, $R^a$, $R^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

$W^{2A}$ is $CR^{W2A}$.

$R^{W2A}$ is selected from the group consisting of hydrogen, $C_{1-4}$alkyl, —O—$C_{1-4}$alkyl, $C_{2-6}$alkenyl, $C_{2-6}$alkynyl, $C_{3-6}$cycloalkyl, phenyl and heteroaryl; wherein $C_{1-4}$alkyl, $C_{2-6}$alkenyl, $C_{2-6}$alkynyl, $C_{3-6}$cycloalkyl, phenyl and heteroaryl may be optionally substituted independently, for each occurrence, with one, two, three or more substituents selected from the group consisting of halogen, hydroxyl and cyano;

BB, independently for each occurrence, is a 4-7-membered cycloalkyl, heterocyclic, aryl, or heteroaryl moiety; wherein the cycloalkyl, heterocyclic, aryl, or heteroaryl moiety may be optionally substituted with one, two, three or more groups represented by $R^{BB}$; wherein $R^1$, independently for each occurrence, may be optionally bonded to BB;

each $R^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —$C_{1-4}$alkyl, —O—$C_{1-4}$alkyl, —N($R^a$)—$C_{1-4}$alkyl, —C(O)$C_{1-4}$alkyl, —C(O)—O—$C_{1-4}$alkyl, —C(O)—$NR^aR^b$, —$C_{2-6}$alkenyl, —$C_{2-6}$alkynyl, —$C_{3-6}$cycloalkyl), heterocyclic, phenyl, phenoxy, heteroaryl, —$C_{1-4}$alkylene-phenyl, —$C_{1-4}$alkylene-heteroaryl, —$C_{1-4}$alkylene-heterocyclyl, —$C_{2-6}$alkenylene-phenyl, —$C_{2-6}$alkenylene-heteroaryl, —$C_{2-6}$alkenylene-heterocyclyl, —$C_{2-6}$alkynyl-phenyl, —$C_{2-6}$alkynyl-heteroaryl, —$C_{2-6}$alkynyl-heterocyclyl; wherein $C_{1-4}$alkyl, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-14}$alkyl, —C(O)—O—$C_{1-4}$alkyl, —C(O)—$NR^aR^b$, halogen, cyano, hydroxyl, cycloalkyl, heterocyclic, phenyl, or heteroaryl, and $R^a$ and $R^b$ are defined herein; or two $R^{BB}$ together with the atoms to which they are attached may form a fused 5- or 6-membered cycloalkyl or heterocyclic bicyclic ring system.

In another aspect, a therapeutic multimer compound formed from the multimerization in an aqueous media of a first monomer $X^3$—$Y^3$—$Z^3$ with a second monomer $X^3$—$Y^3$—$Z^3$ is provided.

In yet another aspect, a method of treating a disease associated with a target protein or a target protein-protein interaction in a patient in need thereof is provided. The method comprises administering to the patient the monomer selected from $X^3$—$Y^3$—$Z^3$ (Formula IV), wherein upon administration, the silyl monomer forms a homomultimer in vivo that binds to one, two, three or more protein domains in said target protein, or to at least one protein domain in each of the proteins involved in the protein-protein interaction.

In still another aspect, a first monomer capable of forming a biologically useful multimer when in contact with one, two, three or more second monomers in an aqueous media is provided. The first monomer is represented by the formula:

$X^1$—$Y^1$—$Z^1$            (Formula I)

and pharmaceutically acceptable salts, stereoisomers, metabolites and hydrates thereof, wherein $X^1$ is a first ligand moiety capable of binding to and modulating a first target biomolecule;

$Y^1$ is absent or is a connector moiety covalently bound to $X^1$ and $Z^1$;

$Z^1$ comprises one, two, three or more silyl moieties; and the second monomer comprises one, two, three or more silyl moieties, capable of binding with the $Z^1$ moiety of Formula I to form the multimer.

In another aspect, a method of administering a pharmaceutically effective amount of a multimeric compound to a patient in need thereof is provided. The method comprises administering to the patient thereof an amount of the first monomer and an amount of the second monomer in amounts effective such that the pharmaceutically effective amount of the resulting multimer is formed in vivo.

In yet another aspect, a therapeutic multimer compound formed from the multimerization in an aqueous media of the first and second monomer is provided. The first monomer is represented by:

$X^1$—$Y^1$—$Z^1$            (Formula I)

and pharmaceutically acceptable salts, stereoisomers, metabolites and hydrates thereof, and the second monomer represented by:

$$X^2—Y^2—Z^2 \quad \text{(Formula II)}$$

and pharmaceutically acceptable salts, stereoisomers, metabolites and hydrates thereof.

In still another aspect, a method of modulating two or more target biomolecule domains substantially simultaneously is provided. The method comprises contacting an aqueous composition comprising said target biomolecule domains with a first monomer represented by:

$$X^1—Y^1—Z^1 \quad \text{(Formula I)}$$

and pharmaceutically acceptable salts, stereoisomers, metabolites and hydrates thereof, wherein
$X^1$ is a first ligand moiety capable of binding to and modulating a first target biomolecule domain; and
a second monomer represented by:

$$X^2—Y^2—Z^2 \quad \text{(Formula II)},$$

wherein
$X^2$ is a ligand moiety capable of binding to and modulating a second target biomolecule domain;
wherein upon contact with the aqueous composition, said first monomer and said second monomer forms a multimer that binds to the first target biomolecule domain and the second target biomolecule domain.

In yet another aspect, a method of treating a disease associated with two or more target biomolecule domains in a patient in need thereof is provided. The method comprises administering to said patient a first monomer represented by:

$$X^1—Y^1—Z^1 \quad \text{(Formula I)}$$

and pharmaceutically acceptable salts, stereoisomers, metabolites and hydrates thereof, wherein
$X^1$ is a first ligand moiety capable of binding to and modulating a first target biomolecule domain; and
administering to said patient a second monomer represented by:

$$X^2—Y^2—Z^2 \quad \text{(Formula II)},$$

wherein
$X^2$ is a second ligand moiety capable of binding to a second target biomolecule domain, wherein upon administration, said first monomer and said second monomer forms a multimer in vivo that binds to the first target biomolecule domain and the second target biomolecule domain.

In still another aspect, a compound is selected from the group consisting of: (4-(3-(aminomethyl)phenyl)piperidin-1-yl)(4-((hydroxydimethylsilyl)methoxy)-phenyl)methanone; N-(4-(4-(3-(aminomethyl)phenyl)-piperidine-1-carbonyl)-2-chlorophenyl)-2-(hydroxydimethylsilyl) acetamide; N-(3-(4-(3-(aminomethyl)phenyl)piperidine-1-carbonyl)-phenyl)-2-(hydroxydimethylsilyl)acetamide; (4-(3-(aminomethyl)phenyl)piperidin-1-yl)(3-chloro-4-((hydroxydimethylsilyl)methoxy)-phenyl)methanone; (4-(3-(aminomethyl)phenyl)-piperidin-1-yl)(3-((hydroxydimethylsilyl)-methoxy)phenyl)methanone; (4-(3-(aminomethyl)-phenyl)piperidin-1-yl)(3-chloro-5-((hydroxydimethylsilyl)methoxy)phenyl)methanone; N-(4-(4-(3-(aminomethyl)phenyl)-piperidine-1-carbonyl) phenyl)-2-(hydroxydimethylsilyl)acetamide; and pharmaceutically acceptable salts, stereoisomers, metabolites and hydrates thereof.

DETAILED DESCRIPTION

Figure 1A:
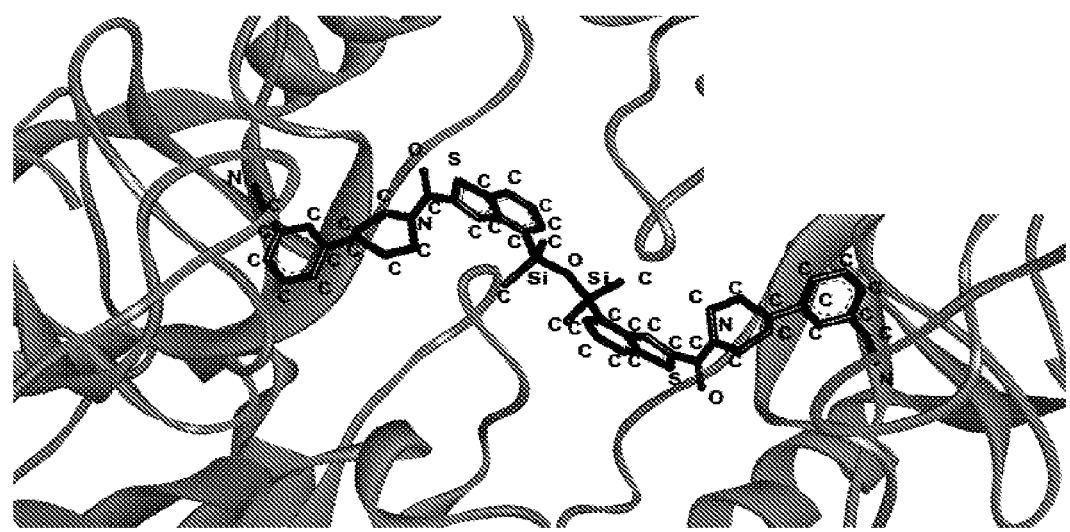
FIG. 1A shows an x-ray co-crystal structure of a silyl multimer bound to adjacent subunits of mast cell beta-tryptase-II, according to an embodiment. The cationic aminomethyl-phenyl-piperidine moieties of the multimer are bound in the pharmacophoric pockets of the tryptase subunits, and the coferon monomers are joined by a covalent disiloxane linkage.
Figure 1B:
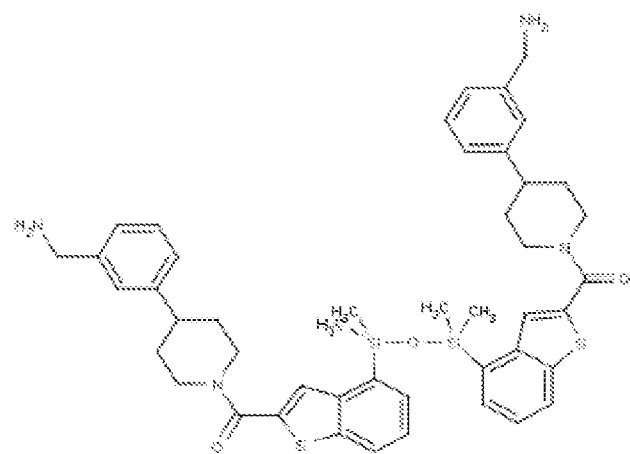
FIG. 1B shows the chemical structure of the multimer bound to tryptase in FIG. 1A, according to an embodiment.
Figure 2:
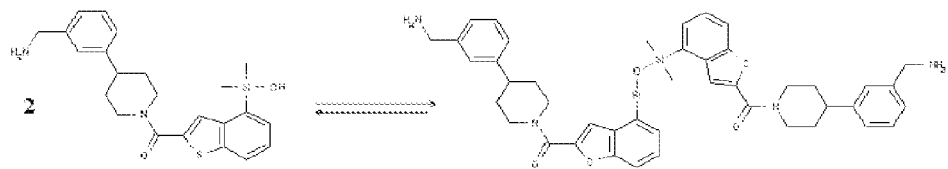
FIG. 2 shows a reaction scheme for the formation of the 1:1 multimer, T46 homodimer (see FIG. 1A and FIG. 1B), from two T46 monomers, according to an embodiment.
Figure 3A:
FIG. 3A shows an x-ray co-crystal structure of T148 Homodimer bound to adjacent subunits of mast cell beta-tryptase-II, according to an embodiment. The cationic aminomethyl-phenyl-piperidine moieties of the multimer are bound in the pharmacophoric pockets of the tryptase subunits, and the coferon monomers are joined by a covalent disiloxane linkage.
Figure 3B:
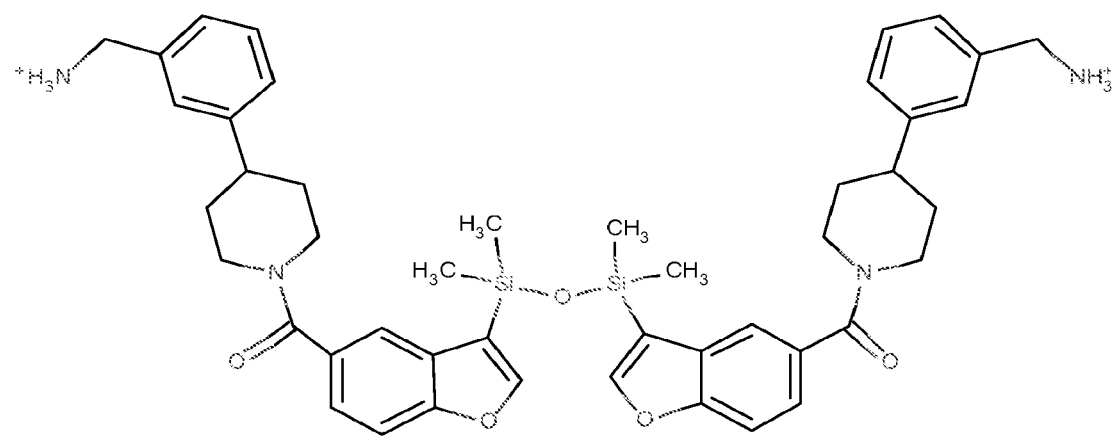
FIG. 3B shows the chemical structure of the homodimeric T148 bound to tryptase in FIG. 3A, according to an embodiment.
Figure 4:
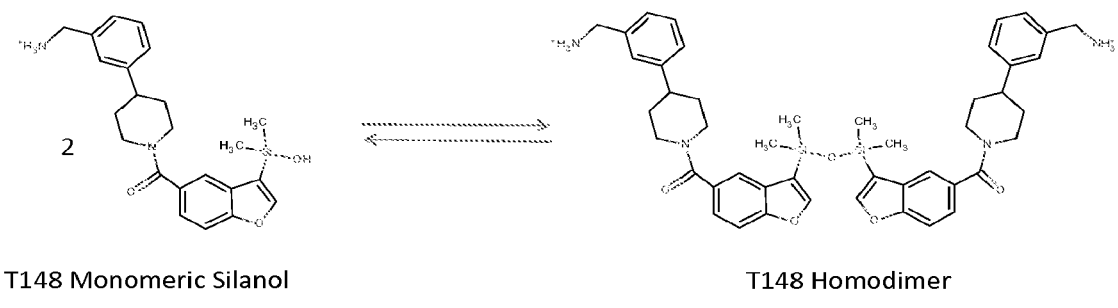
FIG. 4 shows a reaction scheme for the formation of the 1:1 multimer, T148 homodimer (right; see FIG. 3A and FIG. 3B), from two T148 silanol monomers (left), according to an embodiment.

Described herein are monomers capable of forming a biologically useful multimer when in contact with one, two, three or more other monomers in an aqueous media. In one aspect, such monomers may be capable of binding to another monomer in an aqueous media (e.g. in vivo) to form a multimer, (e.g. a dimer). Contemplated monomers may include a ligand moiety (e.g. a ligand or pharmacophore moiety), a linker element, and a connector element that joins the ligand moiety and the linker element. In an aqueous media, such contemplated monomers may join together via each linker element and may thus be capable of modulating one or more biomolecules substantially simultaneously, e.g., modulate two or more binding domains on a protein or on different proteins. For example, contemplated monomers may be separate or separatable in a solid or in an aqueous media under one set of conditions, and when placed in an aqueous media having one or more biomolecules, with another (e.g., under a different set of conditions), can 1) form a multimer through the linker on each monomer; and either: 2a) bind to the biomolecule in two or more locations (e.g. protein domains) through each ligand moiety of the respective monomer or 2b) bind to two or more biomolecules through each ligand moiety of the respective monomer. In an exemplary embodiment, disclosed monomers may interact with another appropriate monomer (i.e. a monomeric pair) in an aqueous media (e.g., in vivo) to form a multimer (e.g. a dimer) that can bind to two separate target biomolecule domains (e.g. protein domains).

The ligand moiety of a contemplated monomer, in some cases, may be a pharmacophore or a ligand moiety that is e.g., capable of binding to a biomolecule, such as for example, a protein, e.g. a specific protein domain, a component of a biological cell such as ribosome (composed of proteins and nucleic acids), or an enzyme active site (e.g. a protease, such as tryptase). In some embodiments, the linker element comprises a functional group capable of forming a chemical bond with another linker element. In some embodiments, the linker moiety may also serve as a signaling entity or "reporter," and in some instances the assembly of two or more linkers can produce a fluorescent entity or fluorophore with properties distinct from the individual linker moiety. In another aspect, a plurality of monomers, each comprising a linker element, may react to form a multimer connected by the linker elements. In some embodiments, the multimer may be formed in vivo. In some instances, the multimer may have enhanced properties relative to the monomers that form the multimer. For example, in certain embodiments, the multimer may bind to a target with greater affinity than any of the monomers that form the multimer. Also described are methods of making the compositions and methods of administering the compositions.

In some embodiments, a plurality of monomers may assemble to form a multimer. The multimer may be used for a variety of purposes. For example, in some instances, the multimer may be used to perturb a biological system. As described in more detail below, in some embodiments, the multimer may bind to a target biomolecule, such as a protein, nucleic acid, or polysaccharide. In certain embodiments, the multimer may be used as a pharmaceutical.

Advantageously, in some embodiments, the multimer may form in vivo upon administration of suitable monomers to a subject. Also advantageously, the multimer may be capable of interacting with a relatively large target site as compared to the individual monomers that form the multimer. For example, a target may comprise, in some embodiments, two protein domains separated by a distance such that a multimer, but not a monomer, may be capable of binding to both domains essentially simultaneously. In some embodiments, contemplated multimers may bind to a target with greater affinity as compared to a monomer binding affinity alone.

In some embodiments, a contemplated multimer may advantageously exhibit enhanced properties relative to the monomers that form the multimer. As discussed above, a multimer may have improved binding properties as compared to the monomers alone. In some embodiments, a multimer may have improved signaling properties. For example, in some cases, the fluorescent properties of a multimer may be different as compared to a monomer. As discussed in more detail below, in some embodiments the fluorescent brightness of a multimer at a particular wavelength may be greater than the fluorescent brightness at the same wavelength of the monomers that form the multimer. Advantageously, in some embodiments, a difference in signaling properties between the multimer and the monomers that form the multimer may be used to detect formation of the multimer. In some embodiments, detection of the formation of the multimer may be used to screen monomers, as discussed in more detail below. Also as discussed in more detail below, in some embodiments, the multimers may be used for imaging or as diagnostic agents.

It should be understood that a multimer, as used herein, may be a homomultimer (i.e., a multimer formed from two or more essentially identical monomers) or may be a heteromultimer (i.e., a multimer formed from two or more substantially different monomers). In some embodiments, a contemplated multimer may comprise 2 to about 10 monomers, for example, a multimer may be a dimer, a trimer, a tetramer, or a pentamer.

In some embodiments, a monomer may comprise a ligand moiety, a linker element, and a connector element that associates the ligand moiety with the linker element. In some embodiments, the linker element of a first monomer may combine with the linker element of a second monomer. In some cases, the linker element may comprise a functional group that can react with a functional group of another linker element to form a bond linking the monomers. In some embodiments, the linker element of a first monomer may be substantially the same as the linker element of a second monomer. In some embodiments, the linker element of a first monomer may be substantially different than the linker element of a second monomer.

In some cases, the ligand moiety may be a pharmacophore. In some embodiments, the ligand moiety (e.g., a pharmacophore) may bind to a target molecule with a dissociation constant of less than 1 mM, in some embodiments less than 500 microM, in some embodiments less than 300 microM, in some embodiments less than 100 microM, in some embodiments less than 10 microM, in some embodiments less than 1 microM, in some embodiments less than 100 nM, in some embodiments less than 10 nM, and in some embodiments less than 1 nM.

In some embodiments, the $IC_{50}$ of the first monomer against a first target biomolecule and the $IC_{50}$ of the second monomer against a second target biomolecule (or second binding site on the first biomolecule) may be greater than the apparent $IC_{50}$ of a combination of the monomers against the first target biomolecule and the second target biomolecule (or second binding site on the first biomolecule). That is, the apparent $IC_{50}$ of a combination of the monomers against the first target biomolecule and the second target biomolecule may advantageously be lower than the $IC_{50}$ of the first monomer against a first target biomolecule and the $IC_{50}$ of the second monomer against a second target biomolecule. The combination of monomers may be any suitable ratio. For example, the ratio of the first monomer to the second monomer may be between 10:1 to 1:10, in some embodiments between 5:1 and 1:5, and in some embodiments between 2:1 and 1:2. In some cases, the ratio of the first monomer to the second monomer may be essentially 1:1. In some instances, the ratio of the smaller of the $IC_{50}$ of the first monomer and the second monomer to the apparent $IC_{50}$ of the multimer may be at least 3.0. In other instances, the ratio of the smaller $IC_{50}$ of the first monomer or the second monomer to the apparent $IC_{50}$ of the multimer may be at least 10.0. In some embodiments, the ratio of the smaller $IC_{50}$ of the first monomer or the second monomer to the apparent $IC_{50}$ of the multimer may be at least 30.0.

For example, for disclosed monomers forming a heteromultimer, the apparent $IC_{50}$ resulting from an essentially equimolar combination of monomers against the first target biomolecule and the second target biomolecule is at least about 3 to 10 fold lower, at least about 10 to 30 fold lower, at least about 30 fold lower, or at least about 40 to 50 fold lower than the lowest of the $IC_{50}$ of the second monomer against the second target biomolecule or the $IC_{50}$ of the first monomer against the first target biomolecule.

It will be appreciated that for monomers forming homodimers (or homo-oligomeric or homomultimeric, as described below), in aqueous solution, there may an equilibrium between the monomeric and dimeric (or oligomeric) states with higher concentrations favoring greater extent of dimer formation. As the binding of monomers to the target biomolecule increases their proximity and effectively increases their local concentration on the target, the rate and extent of dimerization (oligomerization) is promoted when geometries are favorable. As a result, the occupancy of the target by favorable monomers may be nearly completely in the homodimeric (or oligomeric) state. In this manner the target for example, may serve as a template for the dimerization of the monomers, significantly enhancing the extent and rate of dimerization.

Affinities of heterodimerizing monomers for the target biomolecule(s) can often be assessed through the testing of the respective monomers in appropriate assays for the target activity or biology because their self-association to form homo-dimers may not be promoted by binding to the target(s). In contrast, the testing of homodimerizing monomers may not, in some embodiments, afford an affinity solely for the monomeric or dimeric state, but rather the observed effect (e.g. $IC_{50}$) is a result of the monomer-dimer dynamics and equilibrium, with the apparent binding affinity (or $IC_{50}$) being e.g., a weighted measure of the monomer and dimeric inhibitory effects upon the target. In some embodiments, a dimeric species may not form in detectable concentrations in solution, yet a target biomolecule may be bound primarily by the dimeric species, indicating that a dimeric species does in fact form. Thus, the ability or lack of ability to detect a dimeric species in solution should not be construed as an indication of whether dimeric species is being formed.

In some cases, the pH of the aqueous fluid in which the multimer forms may be between pH 1 and and 9, in some embodiments between pH 1 and 3, in some embodiments between pH 3 and 5, in some embodiments between pH 5 and 7, and in some embodiments between pH 7 and 9. In some embodiments, the multimer may be stable in an aqueous solution having a pH between pH 1 and 9, in some embodiments between pH 1 and 3, in some embodiments between pH 3 and 5, in some embodiments between pH 5 and 7, and in some embodiments between pH 7 and 9. In some embodiments, the aqueous solution may have a physiologically acceptable pH.

In some embodiments, the ligand moiety may be capable of binding to a target and at least partially disrupting a biomolecule-biomolecule interaction (e.g., a protein-protein interaction). In some embodiments, the ligand moiety may be capable of binding to a target and at least partially disrupting a protein-nucleic acid interaction. In some cases, the ligand moiety may be capable of binding to a target and at least partially disrupting a protein-lipid interaction. In some cases, the ligand moiety may be capable of binding to a target and at least partially disrupting a protein-polysaccharide interaction. In some embodiments, the ligand moiety may be capable of at least partially stabilizing a biomolecule-biomolecule interaction. In certain embodiments, the ligand moiety may be capable of at least partially inhibiting a conformational change in a biomolecule target.

In some instances, the linker element may be capable of generating a signal. For example, in some embodiments, the linker element may be capable of fluorescing. In some cases, the linker element may have greater fluorescence when the monomer to which it is attached is part of a multimer as compared to when the monomer to which it is attached is not part of a multimer. In some embodiments, upon multimer formation, the fluorescent brightness of a linker element may increase by at least 2-fold, in some embodiments by at least 5-fold, in some embodiments by at least 10-fold, in some embodiments by at least 50-fold, in some embodiments by at least 100-fold, in some embodiments by at least 1000-fold, and in some embodiments by at least 10000-fold. In some embodiments, a linker element in a multimer may have a peak fluorescence that is red-shifted relative to the peak fluorescence of the linker element in a monomer. In other embodiments, a linker element may have a peak fluorescence that is blue-shifted relative to the peak fluorescence of a linker element in a monomer.

Monomers

In a certain embodiment, a first silyl monomer may be capable of forming a biologically useful multimer when in contact with one, two, three or more second silyl monomers. The first and second silyl monomer are represented by the formula:

$$X^3-Y^3-Z^3 \quad \text{(Formula III)}$$

and pharmaceutically acceptable salts, stereoisomers, metabolites and hydrates thereof, wherein
$X^3$ is a first ligand moiety capable of binding to and modulating a first target biomolecule;
$Y^3$ is absent or is a connector moiety covalently bound to $X^3$ and $Z^3$;
$Z^3$ is independently selected from the group consisting of:

a)

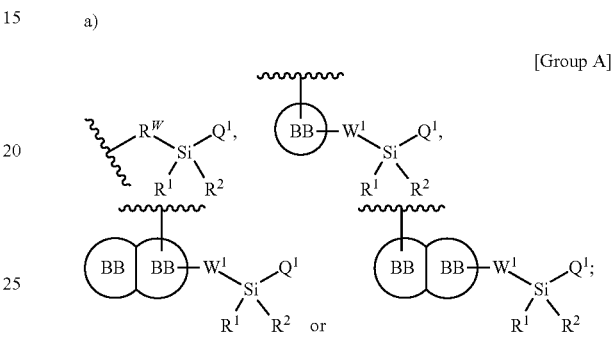

[Group A]

wherein
$R^W$ is selected from the group consisting of a bond, —$C_{1-4}$alkyl-, —O—$C_{1-4}$alkyl-, —N($R^a$)—$C_{1-4}$alkyl-, —$C_{1-4}$ alkyl-C(O)—, —C(O)$C_{1-4}$alkyl-, —$C_{1-4}$alkyl-O—C(O)—, —C(O)—O—$C_{1-4}$alkyl-, —$NR^a$—C(O)—, —$C_{2-6}$alkenyl-, —$C_{2-6}$alkynyl-, —$C_{3-6}$cycloalkyl-, -phenyl-, -heteroaryl-, and -heterocyclic-; wherein $C_{1-4}$alkyl, $R^a$, $R^b$, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—$NR^aR^b$, halogen, cyano, hydroxyl, cycloalkyl, heterocyclic, phenyl, heteroaryl, $R^a$ and $R^b$, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

$W^1$, independently for each occurrence, is (a) absent; or (b) selected from the group consisting of —$C_{1-4}$alkyl-, —O—$C_{1-4}$alkyl-, —$C_{1-4}$alkyl-C(O)—, —C(O)—$C_{1-4}$alkyl-, —N($R^a$)—$C_{1-4}$alkyl-, —$C_{1-4}$alkyl-O—C(O)—, —C(O)—O—$C_{1-4}$alkyl-, —$NR^a$—C(O)—, —$C_{2-6}$alkenyl-, —$C_{2-6}$alkynyl-, —$C_{3-6}$cycloalkyl-, -phenyl-, -heteroaryl-, and heterocyclic; wherein $C_{1-4}$alkyl, $C_{2-6}$alkenyl, $C_{2-6}$alkynyl, $C_{3-6}$cycloalkyl, R', phenyl, heterocyclic, and heteroaryl are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

R' may be independently selected, for each occurrence, from the group consisting of hydrogen, substituted or unsubstituted aliphatic, and substituted or unsubstituted heteroaliphatic;

Q¹ may be independently selected, for each occurrence, from the group consisting of —NHR', —N(R')$_2$, —NR$^a$R$^b$, —O—Si(R')$_3$, —O—SiR$^a$R$^b$R', —SH, —OH, —O—C$_{1-6}$alkyl, —S—C$_{1-6}$alkyl, —O-aryl, —S-aryl, heteroaryl, —O-heteroaryl, —S-heteroaryl, halogen and —O—C$_{1-6}$alkyl-NR$^a$R$^b$;

R$^a$ and R$^b$ may be independently selected, for each occurrence, from the group consisting of hydrogen, C$_{1-4}$alkyl, —O—C$_{1-4}$alkyl and —NH—C$_{1-4}$alkyl; wherein C$_{1-4}$alkyl may be optionally substituted by one or more substituents selected from the group consisting of halogen, cyano, oxo and hydroxyl; or R$^a$ and R$^b$, together with the nitrogen to which they are attached, may form a 4-7 membered heterocyclic ring, which may have one or more additional heteroatoms selected from O, S, or N; wherein the 4-7 membered heterocyclic ring may be optionally substituted by one or more substituents selected from the group consisting of halogen, cyano, oxo, amino and hydroxyl;

R¹ and R² are selected independently, for each occurrence, from the group consisting of —OH, C$_{1-6}$alkyl, —O—C$_{1-6}$alkyl, C$_{2-6}$alkenyl, C$_{3-6}$cycloalkyl, —C$_{1-6}$alkyl-NR$^a$R$^b$, phenyl and heteroaryl; wherein C$_{1-6}$alkyl, C$_{2-6}$alkenyl, C$_{3-6}$cycloalkyl, R$^a$, R$^b$, phenyl and heteroaryl, independently selected, for each occurrence, may be optionally substituted by one or more substituents selected from the group consisting of halogen, cyano, hydroxyl, amino, C$_{1-6}$alkyl, heteroaryl, and phenyl; or R¹ and R², together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

BB, independently for each occurrence, may be a 4-7-membered cycloalkyl, heterocyclic, aryl, or heteroaryl moiety, wherein the cycloalkyl, heterocyclic, aryl, or heteroaryl moiety is optionally substituted with one, two, three or more groups represented by R$^{BB}$; wherein R¹, independently for each occurrence, may be optionally bonded to BB;

each R$^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —C$_{1-4}$alkyl, —O—C$_{1-4}$alkyl, —N(R$^a$)—C$_{1-4}$alkyl, —C(O)C$_{1-4}$alkyl, —C(O)—O—C$_{1-4}$alkyl, —C(O)—NR$^a$R$^b$, —C$_{2-6}$alkenyl, —C$_{2-6}$alkynyl, —C$_{3-6}$cycloalkyl), heterocyclic, phenyl, phenoxy, heteroaryl, —C$_{1-4}$alkylene-phenyl, —C$_{1-4}$alkylene-heteroaryl, —C$_{1-4}$alkylene-heterocyclyl, —C$_{2-6}$alkenylene-phenyl, —C$_{2-6}$alkenylene-heteroaryl, —C$_{2-6}$alkenylene-heterocyclyl, —C$_{2-6}$alkynyl-phenyl, —C$_{2-6}$alkynyl-heteroaryl, —C$_{2-6}$alkynyl-heterocyclyl; wherein C$_{1-4}$alkyl, C$_{2-6}$alkenyl, C$_{2-6}$alkynyl, C$_{3-6}$cycloalkyl, phenyl and heteroaryl may be optionally substituted by one, two, three or more substituents selected from the group consisting of C$_{1-4}$alkyl, C$_{1-4}$alkoxy, —C(O)C$_{1-4}$alkyl, —C(O)—O—C$_{1-4}$alkyl, —C(O)—NR$^a$R$^b$ halogen, cyano, hydroxyl, cycloalkyl, heterocyclic, phenyl, or heteroaryl, and R$^a$ and R$^b$ are defined herein; or two R$^{BB}$ together with the atoms to which they are attached form a fused 5- or 6-membered cycloalkyl or heterocyclic bicyclic ring system; and b)

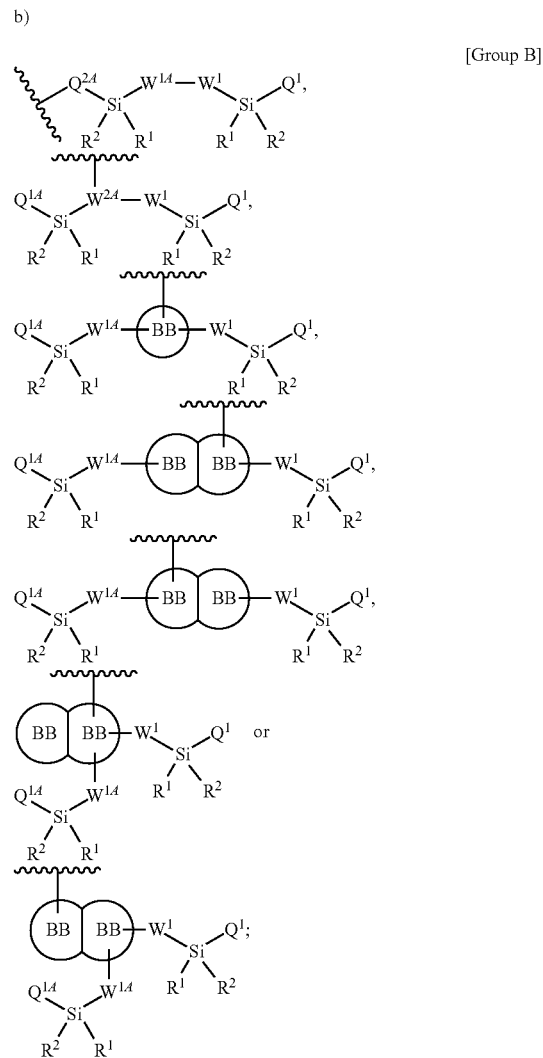

[Group B]

wherein

Q$^{2A}$ may be selected from the group consisting of a bond, —O—C$_{1-6}$alkyl-, —N(R')—C$_{1-6}$alkyl-, and —S—C$_{1-6}$alkyl-;

W¹, independently for each occurrence, is (a) absent; or (b) selected from the group consisting of —C$_{1-4}$alkyl-, —O—C$_{1-4}$alkyl-, —N(R$^a$)—C$_{1-4}$alkyl-, —C$_{1-4}$alkyl-C(O)—, —C(O)C$_{1-4}$alkyl-, —C$_{1-4}$alkyl-O—C(O)—, —C(O)—O—C$_{1-4}$alkyl-, —NR'—C(O)—, —C$_{2-6}$alkenyl-, —C$_{2-6}$alkynyl-, —C$_{3-6}$cycloalkyl-, -phenyl-, and -heteroaryl-; wherein C$_{1-4}$alkyl, C$_{2-6}$alkenyl, C$_{2-6}$alkynyl, C$_{3-6}$cycloalkyl, R', R$^a$ phenyl and heteroaryl may be optionally substituted independently, for each occurrence, with one, two, three or more substituents selected from the group consisting of C$_{1-4}$alkyl, C$_{1-4}$alkoxy, —C(O)C$_{1-6}$alkyl, —C(O)—O—C$_{1-4}$alkyl, halogen, hydroxyl, nitro, carbamate, carbonate and cyano;

W$^{1A}$, independently for each occurrence, is (a) absent; or (b) selected from the group consisting of —C$_{1-4}$alkyl-, —C$_{1-4}$alkyl-O—, —C$_{1-4}$alkyl-N(R$^a$)—, —C$_{1-4}$alkyl-C(O)—, —C(O)C$_{1-4}$alkyl-, —C$_{1-4}$alkyl-O—C(O)—, —C(O)—O—C$_{1-4}$alkyl-, —C(O)—NR'—, —C$_{2-6}$alkenyl-, —C$_{2-6}$alkynyl-, —C$_{3-6}$cycloalkyl-, -phenyl-, and -heteroaryl-; wherein C$_{1-4}$alkyl, C$_{2-6}$alkenyl, C$_{2-6}$alkynyl, C$_{3-6}$cycloalkyl, R', R$^a$ phenyl and heteroaryl may be optionally substituted independently, for each occurrence, with one, two, three or more substituents selected from the group consisting of $C_{1-4}$alkyl, $C_{1-4}$alkoxy, —C(O)$C_{1-6}$alkyl, —C(O)—O—$C_{1-4}$alkyl, halogen, hydroxyl, nitro, carbamate, carbonate and cyano;

R' may be independently selected, for each occurrence, from the group consisting of hydrogen, substituted or unsubstituted aliphatic, and substituted or unsubstituted heteroaliphatic;

$Q^1$ and $Q^{1A}$ may be independently selected, for each occurrence, from the group consisting of —NHR', —NR$^a$R$^b$, —O—Si(R')$_3$, —O—SiR$^a$R$^b$R', —SH, —OH, —O—$C_{1-6}$alkyl, —S—$C_{1-6}$alkyl, —O-aryl, —S-aryl, heteroaryl, —O-heteroaryl, —S-heteroaryl, halogen and —O—$C_{1-6}$alkyl-NR$^a$R$^b$;

R$^a$ and R$^b$ may be independently selected, for each occurrence, from the group consisting of hydrogen and $C_{1-4}$alkyl; wherein $C_{1-4}$alkyl may be optionally substituted by one or more substituents selected from the group consisting of halogen, cyano, oxo and hydroxyl; or R$^a$ and R$^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl;

$R^1$ and $R^2$ are selected independently, for each occurrence, from the group consisting of —OH, $C_{1-6}$alkyl, —O—$C_{1-6}$alkyl, $C_{2-6}$alkenyl, $C_{3-6}$cycloalkyl, —$C_{1-6}$alkyl-NR$^a$R$^b$, phenyl and heteroaryl; wherein $C_{1-6}$alkyl, $C_{2-6}$alkenyl, $C_{3-6}$cycloalkyl, R$^a$, R$^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

$W^{2A}$ may be CR$^{W2A}$.

R$^{W2A}$ may be selected from the group consisting of hydrogen, $C_{1-4}$alkyl, —O—$C_{1-4}$alkyl, $C_{2-6}$alkenyl, $C_{2-6}$alkynyl, $C_{3-6}$cycloalkyl, phenyl and heteroaryl; wherein $C_{1-4}$alkyl, $C_{2-6}$alkenyl, $C_{2-6}$alkynyl, $C_{3-6}$cycloalkyl, phenyl and heteroaryl may be optionally substituted independently, for each occurrence, with one, two, three or more substituents selected from the group consisting of halogen, hydroxyl and cyano;

BB, independently for each occurrence, may be a 4-7-membered cycloalkyl, heterocyclic, aryl, or heteroaryl moiety; wherein the cycloalkyl, heterocyclic, aryl, or heteroaryl moiety may be optionally substituted with one, two, three or more groups represented by R$^{BB}$; wherein $R^1$, independently for each occurrence, may be optionally bonded to BB;

each R$^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —$C_{1-4}$alkyl, —O—$C_{1-4}$alkyl, —N(R$^a$)—$C_{1-4}$alkyl, —C(O)$C_{1-4}$alkyl, —C(O)—O—$C_{1-4}$alkyl, —C(O)—NR$^a$R$^b$, —$C_{2-6}$alkenyl, —$C_{2-6}$alkynyl, —$C_{3-6}$cycloalkyl), heterocyclic, phenyl, phenoxy, heteroaryl, —$C_{1-4}$alkylene-phenyl, —$C_{1-4}$alkylene-heteroaryl, —$C_{1-4}$alkylene-heterocyclyl, —$C_{2-6}$alkenylene-phenyl, —$C_{2-6}$alkenylene-heteroaryl, —$C_{2-6}$alkenylene-heterocyclyl, —$C_{2-6}$alkynyl-phenyl, —$C_{2-6}$alkynyl-heteroaryl, —$C_{2-6}$alkynyl-heterocyclyl; wherein $C_{1-4}$alkyl, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—NR$^a$R$^b$ halogen, cyano, hydroxyl, cycloalkyl, heterocyclic, phenyl, or heteroaryl, and R$^a$ and R$^b$ are defined herein; or two R$^{BB}$ together with the atoms to which they are attached form a fused 5- or 6-membered cycloalkyl or heterocyclic bicyclic ring system;

R$^W$ is selected from the group consisting of a bond, —$C_{1-4}$alkyl-, —O—$C_{1-4}$alkyl-, —N(R$^a$)—$C_{1-4}$alkyl-, —$C_{1-4}$ alkyl-C(O)—, —C(O)$C_{1-4}$alkyl-, —$C_{1-4}$alkyl-O—C(O)—, —C(O)—O—$C_{1-4}$alkyl-, —NR$^a$—C(O)—, —$C_{2-6}$alkenyl-, —$C_{2-6}$alkynyl-, —$C_{3-6}$cycloalkyl-, -phenyl-, -heteroaryl-, and -heterocyclic-; wherein $C_{1-4}$alkyl, R$^a$, R$^b$, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—NR$^a$R$^b$, halogen, cyano, hydroxyl, cycloalkyl, heterocyclic, phenyl, heteroaryl, R$^a$ and R$^b$, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino.

It should be noted that substituents R$^w$, $Q^{2A}$, $W^1$, and $W^{1A}$ are oriented such that a Si-heteroatom bond does not occur (e.g., a Si—O bond, a Si—N bond, or a Si—S bond). For example, when R$^w$ is —O—$C_{1-4}$alkyl-, the —O—$C_{1-4}$alkyl-substituent would be oriented such that Si is bonded to the $C_{1-4}$alkyl group (e.g., —O—$C_{1-4}$alkyl-Si—) and not to the O atom.

In some cases, the first silyl monomer may form a biologically useful multimer when in contact with one, two, three or more second silyl monomers in vivo. For example, the multimer may be a biologically useful dimer when the first silyl monomer is in contact with the second silyl monomer. Alternatively, the multimer may be a biologically useful trimer when the first silyl monomer is in contact with two second silyl monomers. In other instances, the multimer may be a biologically useful cyclic tetramer when the first silyl monomer is in contact with three second silyl monomers.

In some embodiments, the ligand moiety may be a pharmacophore and the target biomolecule may be a protein target. For example, the first target biomolecule may be a protein component of the ribosome. In another embodiment, the first target biomolecule may be a subunit of tryptase. In other cases, $X^3$ may be a non-peptidyl ligand moiety.

In another embodiment, the modulating effects of the multimer formed from the silyl monomers is greater than the sum of the modulating effects of the individual monomers.

In certain embodiments, a first monomer may be capable of forming a biologically useful multimer when in contact with one, two, three or more second monomers in an aqueous media, wherein the first monomer is represented by the formula:

$$X^1—Y^1—Z^1 \qquad \text{(Formula I)}$$

and pharmaceutically acceptable salts, stereoisomers, metabolites and hydrates thereof, wherein $X^1$ is a first ligand moiety capable of binding to and modulating a first target biomolecule;

$Y^1$ is absent or is a connector moiety covalently bound to $X^1$ and $Z^1$;

$Z^1$ comprises one, two, three or more silyl moieties; and the second monomer comprises one, two, three or more silyl moieties, capable of binding with the $Z^1$ moiety of Formula I to form the multimer.

In some instances, $Z^1$ may further comprise a diol moiety. Additionally, the second monomer may further comprise a boronic acid or oxaborale moiety, which may be capable of binding with the $Z^1$ moiety.

In some embodiments, $Z^1$ may be independently selected, for each occurrence, from the group consisting of:

a)

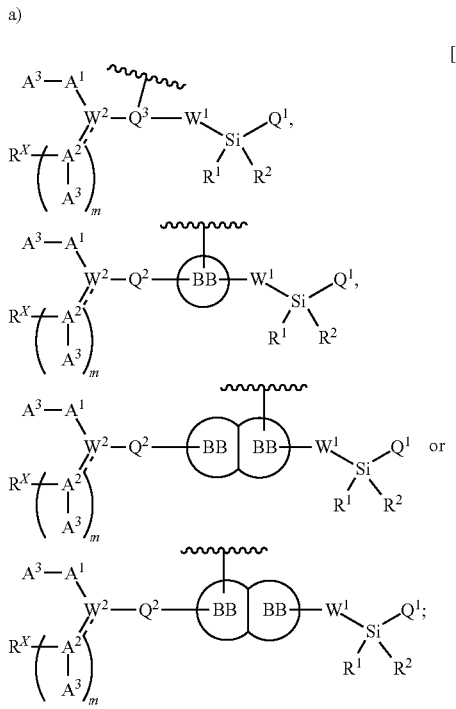

[Group C6]

wherein $A^1$ is (a) absent; or (b) selected from the group consisting of acyl, substituted or unsubstituted aliphatic, and substituted or unsubstituted heteroaliphatic;

$A^2$, independently for each occurrence, is (a) absent; or (b) selected from the group consisting of —N—, acyl, substituted or unsubstituted aliphatic, and substituted or unsubstituted heteroaliphatic, provided that at least one of $A^1$ and $A^2$ is present; or $A^1$ and $A^2$, together with the atoms to which they are attached, form a 4-8 membered cycloalkyl or heterocyclic ring;

$A^3$ is selected from the group consisting of —NHR', —SH, and —OH;

$W^2$ is selected from the group consisting of CR' or N;

m is 1-6;

═ represents a single or double bond; and $R^X$ is (a) absent; or (b) selected from the group consisting of hydrogen, substituted or unsubstituted aliphatic, and substituted or unsubstituted heteroaliphatic;

$Q^2$ is (a) absent; or (b) selected from the group consisting of a substituted or unsubstituted aliphatic and a substituted or unsubstituted heteroaliphatic moiety; or $R^X$ and $Q^2$ together with the atoms to which they are attached form a 4-, 5-, 6-, 7-, or 8-membered cycloalkyl or heterocyclic ring;

$Q^3$ is selected from the group consisting of a substituted or unsubstituted aliphatic and a substituted or unsubstituted heteroaliphatic moiety;

$W^1$, independently for each occurrence, is (a) absent; or (b) selected from the group consisting of —$C_{1-4}$alkyl-, —O—$C_{1-4}$alkyl-, —$C_{1-4}$alkyl-C(O)—, —C(O)—$C_{1-4}$alkyl-, —N($R^a$)—$C_{1-4}$alkyl-, —$C_{1-4}$alkyl-O—C(O)—, —C(O)—O—$C_{1-4}$alkyl-, —$NR^a$—C(O)—, —$C_{2-6}$alkenyl-, —$C_{2-6}$alkynyl-, —$C_{3-6}$cycloalkyl-, -phenyl-, -heteroaryl-, and heterocyclic; wherein $C_{1-4}$alkyl, $C_{2-6}$alkenyl, $C_{2-6}$alkynyl, $C_{3-6}$cycloalkyl, R', phenyl, heterocyclic, and heteroaryl are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

R' is independently selected, for each occurrence, from the group consisting of hydrogen, substituted or unsubstituted aliphatic, and substituted or unsubstituted heteroaliphatic;

$Q^1$ is independently selected, for each occurrence, from the group consisting of —NHR', —N(R')$_2$, —$NR^aR^b$, —O—Si(R')$_3$, —O—Si$R^aR^b$R', —SH, —OH, —O—$C_{1-6}$alkyl, —S—$C_{1-6}$alkyl, —O-aryl, —S-aryl, heteroaryl, —O-heteroaryl, —S-heteroaryl, halogen and —O—$C_{1-6}$alkyl-$NR^aR^b$ $R^a$ and $R^b$ are independently selected, for each occurrence, from the group consisting of hydrogen and $C_{1-4}$alkyl; wherein $C_{1-4}$alkyl may be optionally substituted by one or more substituents selected from the group consisting of halogen, cyano, oxo and hydroxyl; or $R^a$ and $R^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl;

$R^1$ and $R^2$ are selected independently, for each occurrence, from the group consisting of —OH, $C_{1-6}$alkyl, —O—$C_{1-6}$alkyl, $C_{2-6}$alkenyl, $C_{3-6}$cycloalkyl, —$C_{1-6}$alkyl-$NR^aR^b$, phenyl and heteroaryl; wherein $C_{1-6}$alkyl, $C_{2-6}$alkenyl, $C_{3-6}$cycloalkyl, $R^a$, $R^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

BB, independently for each occurrence, is a 5- or 6-membered cycloalkyl, heterocyclic, aryl, or heteroaryl moiety, wherein the cycloalkyl, heterocyclic, aryl, or heteroaryl moiety is optionally substituted with one, two, three or more groups represented by $R^{BB}$; wherein $R^1$, independently for each occurrence, may be optionally bonded to BB;

each $R^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —C$_{1-4}$alkyl, —O—C$_{1-4}$alkyl, —N(R$^a$)—C$_{1-4}$alkyl, —C(O)C$_{1-4}$alkyl, —C(O)—O—C$_{1-4}$alkyl, —C(O)—NR$^a$R$^b$, —C$_{2-6}$alkenyl, —C$_{2-6}$alkynyl, —C$_{3-6}$cycloalkyl), heterocyclic, phenyl, phenoxy, heteroaryl, —C$_{1-4}$alkylene-phenyl, —C$_{1-4}$alkylene-heteroaryl, —C$_{1-4}$alkylene-heterocyclyl, —C$_{2-6}$alkenylene-phenyl, —C$_{2-6}$alkenylene-heteroaryl, —C$_{2-6}$alkenylene-heterocyclyl, —C$_{2-6}$alkynyl-phenyl, —C$_{2-6}$alkynyl-heteroaryl, —C$_{2-6}$alkynyl-heterocyclyl; wherein C$_{1-4}$alkyl, C$_{2-6}$alkenyl, C$_{2-6}$alkynyl, C$_{3-6}$cycloalkyl, phenyl and heteroaryl may be optionally substituted by one, two, three or more substituents selected from the group consisting of C$_{1-4}$alkyl, C$_{1-4}$alkoxy, —C(O)C$_{1-4}$alkyl, —C(O)—O—C$_{1-4}$alkyl, —C(O)—NR$^a$R$^b$, halogen, cyano, hydroxyl, cycloalkyl, heterocyclic, phenyl, or heteroaryl, and R$^a$ and R$^b$ are defined herein; or two R$^{BB}$ together with the atoms to which they are attached form a fused 5- or 6-membered cycloalkyl or heterocyclic bicyclic ring system; and b)

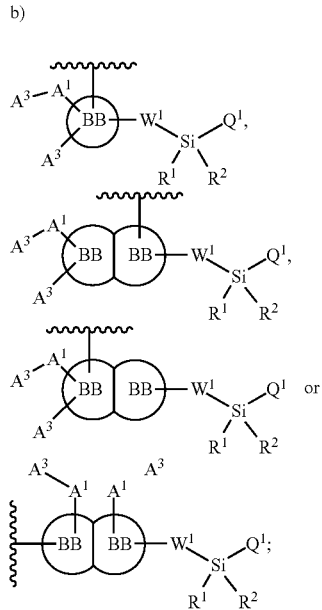

[Group C9]

wherein

A$^1$, independently for each occurrence, is (a) absent; or (b) selected from the group consisting of acyl, substituted or unsubstituted aliphatic, and substituted or unsubstituted heteroaliphatic;

A$^3$, independently for each occurrence, is selected from the group consisting of —NHR', —N(R')$_2$, —SH, and —OH;

W$^1$, independently for each occurrence, is (a) absent; or (b) selected from the group consisting of —C$_{1-4}$alkyl-, —O—C$_{1-4}$alkyl-, —C$_{1-4}$alkyl-C(O)—, —C(O)—C$_{1-4}$alkyl-, —N(R$^a$)—C$_{1-4}$alkyl-, —C$_{1-4}$alkyl-O—C(O)—, —C(O)—O—C$_{1-4}$alkyl-, —NR$^a$—C(O)—, —C$_{2-6}$alkenyl-, —C$_{2-6}$alkynyl-, —C$_{3-6}$cycloalkyl-, -phenyl-, -heteroaryl-, and heterocyclic; wherein C$_{1-4}$alkyl, C$_{2-6}$alkenyl, C$_{2-6}$alkynyl, C$_{3-6}$cycloalkyl, R', phenyl, heterocyclic, and heteroaryl are optionally substituted independently, for each occurrence, with one, two, three or more substituents selected from the group consisting of C$_{1-4}$alkyl, C$_{2-6}$alkenyl, C$_{2-6}$alkynyl, C$_{1-4}$alkoxy, —C(O)C$_{1-6}$alkyl, —C(O)—O—C$_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, C$_{1-6}$alkyl, phenyl, heteroaryl, and amino;

R' is independently selected, for each occurrence, from the group consisting of hydrogen, substituted or unsubstituted aliphatic, and substituted or unsubstituted heteroaliphatic;

Q$^1$ is independently selected, for each occurrence, from the group consisting of —NHR', —N(R')$_2$, —NR$^a$R$^b$, —O—Si(R')$_3$, —O—SiR$^a$R$^b$R', —SH, —OH, —O—C$_{1-6}$alkyl, —S—C$_{1-6}$alkyl, —O-aryl, —S-aryl, heteroaryl, —O-heteroaryl, —S-heteroaryl, halogen and —O—C$_{1-6}$alkyl-NR$^a$R$^b$;

R$^a$ and R$^b$ are independently selected, for each occurrence, from the group consisting of hydrogen and C$_{1-4}$alkyl; wherein C$_{1-4}$alkyl may be optionally substituted by one or more substituents selected from the group consisting of halogen, cyano, oxo and hydroxyl; or R$^a$ and R$^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl;

R$^1$ and R$^2$ are selected independently, for each occurrence, from the group consisting of —OH, C$_{1-6}$alkyl, —O—C$_{1-6}$alkyl, C$_{2-6}$alkenyl, C$_{3-6}$cycloalkyl, —C$_{1-6}$alkyl-NR$^a$R$^b$, phenyl and heteroaryl; wherein C$_{1-6}$alkyl, C$_{2-6}$alkenyl, C$_{3-6}$cycloalkyl, R$^a$, R$^b$, phenyl and heteroaryl, independently selected, for each occurrence, may be optionally substituted by one or more substituents selected from the group consisting of halogen, cyano, hydroxyl, amino, C$_{1-6}$alkyl, heteroaryl, and phenyl; or R$^1$ and R$^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

BB, independently for each occurrence, is a 5- or 6-membered cycloalkyl, heterocyclic, aryl, or heteroaryl moiety, wherein the cycloalkyl, heterocyclic, aryl, or heteroaryl moiety is optionally substituted with one, two, three or more groups represented by R$^{BB}$; wherein R$^1$, independently for each occurrence, may be optionally bonded to BB;

each R$^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —C$_{1-4}$alkyl, —O—C$_{1-4}$alkyl, —N(R$^a$)—C$_{1-4}$alkyl, —C(O)C$_{1-4}$alkyl, —C(O)—O—C$_{1-4}$alkyl, —C(O)—NR$^a$R$^b$, —C$_{2-6}$alkenyl, —C$_{2-6}$alkynyl, —C$_{3-6}$cycloalkyl), heterocyclic, phenyl, phenoxy, heteroaryl, —C$_{1-4}$alkylene-phenyl, —C$_{1-4}$alkylene-heteroaryl, —C$_{1-4}$alkylene-heterocyclyl, —C$_{2-6}$alkenylene-phenyl, —C$_{2-6}$alkenylene-heteroaryl, —C$_{2-6}$alkenylene-heterocyclyl, —C$_{2-6}$alkynyl-phenyl, —C$_{2-6}$alkynyl-heteroaryl, —C$_{2-6}$alkynyl-heterocyclyl; wherein C$_{1-4}$alkyl, C$_{2-6}$alkenyl, C$_{2-6}$alkynyl, C$_{3-6}$cycloalkyl, phenyl and heteroaryl may be optionally substituted by one, two, three or more substituents selected from the group consisting of C$_{1-4}$alkyl, C$_{1-4}$alkoxy, —C(O)C$_{1-4}$alkyl, —C(O)—O—C$_{1-4}$alkyl, —C(O)—NR$^a$R$^b$, halogen, cyano, hydroxyl, cycloalkyl, heterocyclic, phenyl, or heteroaryl, and R$^a$ and R$^b$ are defined herein; or two $R^{BB}$ together with the atoms to which they are attached form a fused 5- or 6-membered cycloalkyl or heterocyclic bicyclic ring system; and c)

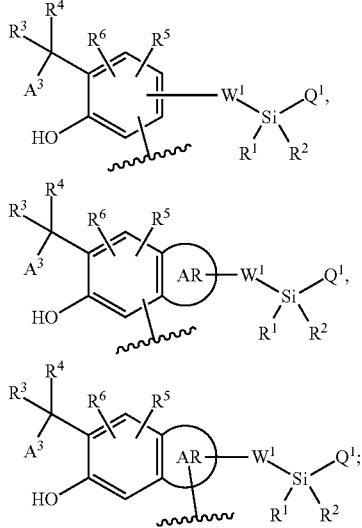 [Group C11]

wherein $A^3$, independently for each occurrence, is selected from the group consisting of —NHR', —SH, and —OH;

$R^3$ and $R^4$ are independently selected from the group consisting of H, $C_{1-4}$alkyl and phenyl; or $R^3$ and $R^4$ taken together form a 3-6 membered ring;

$R^5$ and $R^6$ are independently selected from the group consisting of H, $C_{1-4}$alkyl; wherein $C_{1-4}$alkyl is optionally substituted independently, for each occurrence, with one, two, three or more substituents selected from the group consisting of hydroxyl, amino, halo, thio, $C_{1-4}$alkoxy, halogen, —OH, —CN, —COOH, and C(O)—NHR″; or $R_5$ and $R_6$, taken together form phenyl or a 4-6 membered heterocycle;

R″ is selected from the group consisting of H and $C_{1-4}$alkyl;

$W^1$, independently for each occurrence, is (a) absent; or (b) selected from the group consisting of —$C_{1-4}$alkyl-, —O—$C_{1-4}$alkyl-, —$C_{1-4}$alkyl-C(O)—, —C(O)—$C_{1-4}$alkyl-, —N($R^a$)—$C_{1-4}$alkyl-, —$C_{1-4}$alkyl-O—C(O)—, —C(O)—O—$C_{1-4}$alkyl-, —$NR^a$—C(O)—, —$C_{2-6}$alkenyl-, —$C_{2-6}$alkynyl-, —$C_{3-6}$cycloalkyl-, -phenyl-, -heteroaryl-, and heterocyclic; wherein $C_{1-4}$alkyl, $C_{2-6}$alkenyl, $C_{2-6}$alkynyl, $C_{3-6}$cycloalkyl, R', phenyl, heterocyclic, and heteroaryl are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

R' is independently selected, for each occurrence, from the group consisting of hydrogen, substituted or unsubstituted aliphatic, and substituted or unsubstituted heteroaliphatic;

$Q^1$ is independently selected, for each occurrence, from the group consisting of —NHR', —N(R')$_2$, —$NR^aR^b$, —O—Si(R')$_3$, —O—Si$R^aR^b$R', —SH, —OH, —O—$C_{1-6}$alkyl, —S—$C_{1-6}$alkyl, —O-aryl, —S-aryl, heteroaryl, —O-heteroaryl, —S-heteroaryl, halogen and —O—$C_{1-6}$alkyl-$NR^aR^b$;

$R^a$ and $R^b$ are independently selected, for each occurrence, from the group consisting of hydrogen and $C_{1-4}$alkyl; wherein $C_{1-4}$alkyl may be optionally substituted by one or more substituents selected from the group consisting of halogen, cyano, oxo and hydroxyl; or $R^a$ and $R^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl;

$R^1$ and $R^2$ are selected independently, for each occurrence, from the group consisting of —OH, $C_{1-6}$alkyl, —O—$C_{1-6}$alkyl, $C_{2-6}$alkenyl, $C_{3-6}$cycloalkyl, —$C_{1-6}$alkyl-$NR^aR^b$, phenyl and heteroaryl; wherein $C_{1-6}$alkyl, $C_{2-6}$alkenyl, $C_{3-6}$cycloalkyl, $R^a$, $R^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

AR is a fused phenyl or 4-7 membered aromatic or partially aromatic heterocyclic ring; wherein AR is optionally substituted by oxo, $C_{1-4}$alkyl optionally substituted by hydroxyl, amino, halo, or thio; $C_{1-4}$alkoxy; —S—$C_{1-4}$alkyl; halogen; —OH; —CN; —COOH; —CONHR'; wherein the two hydroxyl moieties are ortho to each other; and the carbons of the phenyl ring may be independently, for each occurrence, optionally replaced by one or two nitrogens.

d)

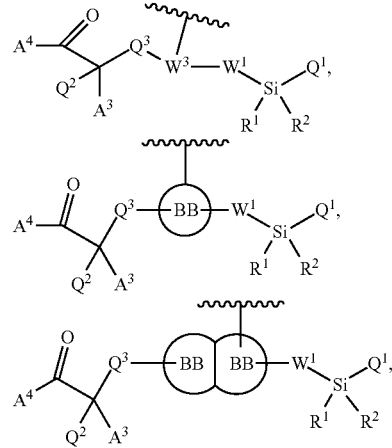 [Group C16]

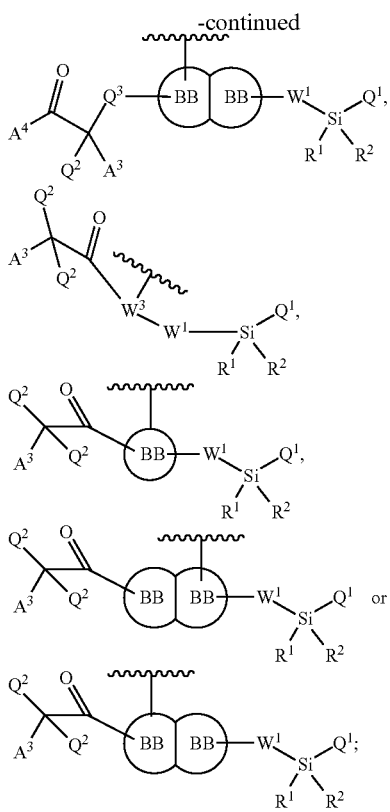

wherein

W³, independently for each occurrence, is selected from the group consisting of N and CR$^{W3}$ R$^{W3}$, independently for each occurrence, is selected from the group consisting of hydrogen, C$_{1-4}$alkyl, —O—C$_{1-4}$alkyl, C$_{2-6}$alkenyl, C$_{2-6}$alkynyl, C$_{3-6}$cycloalkyl, phenyl and heteroaryl; wherein C$_{1-4}$alkyl, C$_{2-6}$alkenyl, C$_{2-6}$alkynyl, C$_{3-6}$cycloalkyl, phenyl and heteroaryl are optionally substituted independently, for each occurrence, with one, two, three or more substituents selected from the group consisting of halogen, hydroxyl and cyano;

Q³ is selected from the group consisting of a bond, —C$_{1-4}$alkyl-, —C$_{2-6}$alkenyl-, —C$_{1-6}$cycloalkyl-, a 5-6 membered heterocyclic ring, and phenyl;

Q², independently for each occurrence, is selected from the group consisting of H, C$_{1-4}$alkyl, C$_{2-6}$alkenyl, C$_{1-6}$cycloalkyl, a 5-6 membered heterocyclic ring, phenyl, substituted or unsubstituted aliphatic, substituted or unsubstituted heteroaliphatic, substituted or unsubstituted aryl, and substituted or unsubstituted heteroaryl;

A³, independently for each occurrence, is selected from the group consisting of NH$_2$, —SH, and —OH;

A⁴, independently for each occurrence, is selected from the group consisting of —NH$_2$, —NH—NH$_2$; —NHOH, —NH—OR", —SH, and —OH;

R" is selected from the group consisting of H and C$_{1-4}$alkyl;

W¹, independently for each occurrence, is (a) absent; or (b) selected from the group consisting of —C$_{1-4}$alkyl-, —O—C$_{1-4}$alkyl-, —C$_{1-4}$alkyl-C(O)—, —C(O)—C$_{1-4}$alkyl-, —N(R$^a$)—C$_{1-4}$alkyl-, —C$_{1-4}$alkyl-O—C(O)—, —C(O)—O—C$_{1-4}$alkyl-, —NR$^a$—C(O)—, —C$_{2-6}$alkenyl-, —C$_{2-6}$alkynyl-, —C$_{3-6}$cycloalkyl-, -phenyl-, -heteroaryl-, and heterocyclic; wherein C$_{1-4}$alkyl, C$_{2-6}$alkenyl, C$_{2-6}$alkynyl, C$_{3-6}$cycloalkyl, R', phenyl, heterocyclic, and heteroaryl are optionally substituted independently, for each occurrence, with one, two, three or more substituents selected from the group consisting of C$_{1-4}$alkyl, C$_{2-6}$alkenyl, C$_{2-6}$alkynyl, C$_{1-4}$alkoxy, —C(O)C$_{1-6}$alkyl, —C(O)—O—C$_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, C$_{1-6}$alkyl, phenyl, heteroaryl, and amino;

R' is independently selected, for each occurrence, from the group consisting of hydrogen, substituted or unsubstituted aliphatic, and substituted or unsubstituted heteroaliphatic;

Q¹ is independently selected, for each occurrence, from the group consisting of —NHR', —N(R')$_2$, —NR$^a$R$^b$, —O—Si(R')$_3$, —O—SiR$^a$R$^b$R', —SH, —OH, —O—C$_{1-6}$alkyl, —S—C$_{1-6}$alkyl, —O-aryl, —S-aryl, heteroaryl, —O-heteroaryl, —S-heteroaryl, halogen and —O—C$_{1-6}$alkyl-NR$^a$R$^b$;

R$^a$ and R$^b$ are independently selected, for each occurrence, from the group consisting of hydrogen and C$_{1-4}$alkyl; wherein C$_{1-4}$alkyl may be optionally substituted by one or more substituents selected from the group consisting of halogen, cyano, oxo and hydroxyl; or R$^a$ and R$^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl;

R¹ and R² are selected independently, for each occurrence, from the group consisting of —OH, C$_{1-6}$alkyl, —O—C$_{1-6}$alkyl, C$_{2-6}$alkenyl, C$_{3-6}$cycloalkyl, —C$_{1-6}$alkyl-NR$^a$R$^b$, phenyl and heteroaryl; wherein C$_{1-6}$alkyl, C$_{2-6}$alkenyl, C$_{3-6}$cycloalkyl, R$^a$, R$^b$, phenyl and heteroaryl, independently selected, for each occurrence, may be optionally substituted by one or more substituents selected from the group consisting of halogen, cyano, hydroxyl, amino, C$_{1-6}$alkyl, heteroaryl, and phenyl; or R¹ and R², together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

BB, independently for each occurrence, is a 5- or 6-membered cycloalkyl, heterocyclic, aryl, or heteroaryl moiety, wherein the cycloalkyl, heterocyclic, aryl, or heteroaryl moiety is optionally substituted with one, two, three or more groups represented by R$^{BB}$; wherein R¹, independently for each occurrence, may be optionally bonded to BB;

each R$^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —C$_{1-4}$alkyl, —O—C$_{1-4}$alkyl, —N(R$^a$)—C$_{1-4}$alkyl, —C(O)C$_{1-4}$alkyl, —C(O)—O—C$_{1-4}$alkyl, —C(O)—NR$^a$R$^b$, —C$_{2-6}$alkenyl, —C$_{2-6}$alkynyl, —C$_{3-6}$cycloalkyl), heterocyclic, phenyl, phenoxy, heteroaryl, —C$_{1-4}$alkylene-phenyl, —C$_{1-4}$alkylene-heteroaryl, —C$_{1-4}$alkylene-heterocyclyl, —C$_{2-6}$alkenylene-phenyl, —C$_{2-6}$alkenylene-heteroaryl, —C$_{2-6}$alkenylene-heterocyclyl, —C$_{2-6}$alkynyl-phenyl, —C$_{2-6}$alkynyl-heteroaryl, —C$_{2-6}$alkynyl-heterocyclyl; wherein C$_{1-4}$alkyl, C$_{2-6}$alkenyl, C$_{2-6}$alkynyl, C$_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—NR$^a$R$^b$, halogen, cyano, hydroxyl, cycloalkyl, heterocyclic, phenyl, or heteroaryl, and R$^a$ and R$^b$ are defined herein; or two R$^{BB}$ together with the atoms to which they are attached form a fused 5- or 6-membered cycloalkyl or heterocyclic bicyclic ring system.

In a certain embodiment, the second monomer may be represented by:

$$X^2-Y^2-Z^2 \qquad \text{(Formula II)},$$

and pharmaceutically acceptable salts, stereoisomers, metabolites and hydrates thereof, wherein $X^2$ is a second ligand moiety capable of binding to and modulating a second target biomolecule;

$Y^2$ is absent or is a connector moiety covalently bound to $X^2$ and $Z^2$;

$Z^2$ comprises one, two, three or more silyl moieties.

In another embodiment, $Z^2$ may further comprise a boronic acid or oxaborale moiety.

In certain embodiments, $Z^1$ and $Z^2$ may be independently selected, for each occurrence, from the group consisting of:

a)

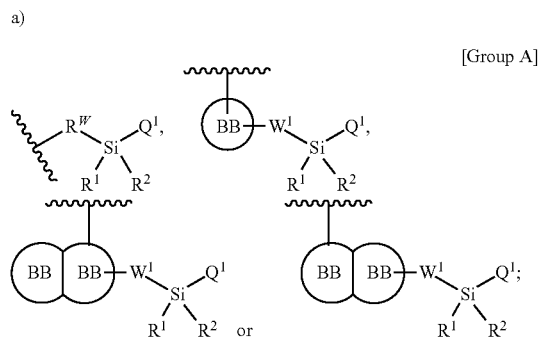

[Group A]

wherein

R$^W$ is selected from the group consisting of a bond, —$C_{1-4}$alkyl-, —O—$C_{1-4}$alkyl-, —N(R$^a$)—$C_{1-4}$alkyl-, —$C_{1-4}$ alkyl-C(O)—, —C(O)$C_{1-4}$alkyl-, —$C_{1-4}$alkyl-O—C(O)—, —C(O)—O—$C_{1-4}$alkyl-, —NR$^a$—C(O)—, —$C_{2-6}$alkenyl-, —$C_{2-6}$alkynyl-, —$C_{3-6}$cycloalkyl-, -phenyl-, -heteroaryl-, and -heterocyclic-; wherein $C_{1-4}$alkyl, R$^a$, R$^b$, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$ alkyl, —C(O)—NR$^a$R$^b$, halogen, cyano, hydroxyl, cycloalkyl, heterocyclic, phenyl, heteroaryl, R$^a$ and R$^b$, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

W$^1$, independently for each occurrence, is (a) absent; or (b) selected from the group consisting of —$C_{1-4}$alkyl-, —O—$C_{1-4}$alkyl-, —$C_{1-4}$alkyl-C(O)—, —C(O)—$C_{1-4}$alkyl-, —N(R$^a$)—$C_{1-4}$alkyl-, —$C_{1-4}$alkyl-O—C(O)—, —C(O)—O—$C_{1-4}$alkyl-, —NR$^a$—C(O)—, —$C_{2-6}$alkenyl-, —$C_{2-6}$alkynyl-, —$C_{3-6}$cycloalkyl-, -phenyl-, -heteroaryl-, and heterocyclic; wherein $C_{1-4}$alkyl, $C_{2-6}$alkenyl, $C_{2-6}$alkynyl, $C_{3-6}$cycloalkyl, R', phenyl, heterocyclic, and heteroaryl are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

R' may be independently selected, for each occurrence, from the group consisting of hydrogen, substituted or unsubstituted aliphatic, and substituted or unsubstituted heteroaliphatic;

Q$^1$ may be independently selected, for each occurrence, from the group consisting of —NHR', —N(R')$_2$, —NR$^a$R$^b$, —O—Si(R')$_3$, —O—SiR$^a$R$^b$R', —SH, —OH, —O—$C_{1-6}$ alkyl, —S—$C_{1-6}$alkyl, —O-aryl, —S-aryl, heteroaryl, —O-heteroaryl, —S-heteroaryl, halogen and —O—$C_{1-6}$alkyl-NR$^a$R$^b$;

R$^a$ and R$^b$ may be independently selected, for each occurrence, from the group consisting of hydrogen, $C_{1-4}$alkyl, —O—$C_{1-4}$alkyl and —NH—$C_{1-4}$alkyl; wherein $C_{1-4}$alkyl may be optionally substituted by one or more substituents selected from the group consisting of halogen, cyano, oxo and hydroxyl; or R$^a$ and R$^b$, together with the nitrogen to which they are attached, may form a 4-7 membered heterocyclic ring, which may have one or more additional heteroatoms selected from O, S, or N; wherein the 4-7 membered heterocyclic ring may be optionally substituted by one or more substituents selected from the group consisting of halogen, cyano, oxo, amino and hydroxyl;

R$^1$ and R$^2$ are selected independently, for each occurrence, from the group consisting of —OH, $C_{1-6}$alkyl, —O—$C_{1-6}$ alkyl, $C_{2-6}$alkenyl, $C_{3-6}$cycloalkyl, —$C_{1-6}$alkyl-NR$^a$R$^b$, phenyl and heteroaryl; wherein $C_{1-6}$alkyl, $C_{2-6}$alkenyl, $C_{3-6}$cycloalkyl, R$^a$, R$^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or R$^1$ and R$^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

BB, independently for each occurrence, may be a 4-7-membered cycloalkyl, heterocyclic, aryl, or heteroaryl moiety, wherein the cycloalkyl, heterocyclic, aryl, or heteroaryl moiety is optionally substituted with one, two, three or more groups represented by R$^{BB}$; wherein R$^1$, independently for each occurrence, may be optionally bonded to BB;

each R$^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —$C_{1-4}$alkyl, —O—$C_{1-4}$alkyl, —N(R$^a$)—$C_{1-4}$alkyl, —C(O)$C_{1-4}$alkyl, —C(O)—O—$C_{1-4}$ alkyl, —C(O)—NR$^a$R$^b$, —$C_{2-6}$alkenyl, —$C_{2-6}$alkynyl, —$C_{3-6}$cycloalkyl), heterocyclic, phenyl, phenoxy, heteroaryl, —$C_{1-4}$alkylene-phenyl, —$C_{1-4}$alkylene-heteroaryl, —$C_{1-4}$alkylene-heterocyclyl, —$C_{2-6}$alkenylene-phenyl, —$C_{2-6}$alkenylene-heteroaryl, —$C_{2-6}$alkenylene-heterocyclyl, —$C_{2-6}$alkynyl-phenyl, —$C_{2-6}$alkynyl-heteroaryl, —$C_{2-6}$alkynyl-heterocyclyl; wherein $C_{1-4}$alkyl, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—NR$^a$R$^b$ halogen, cyano, hydroxyl, cycloalkyl, heterocyclic, phenyl, or heteroaryl, and R$^a$ and R$^b$ are defined herein; or two R$^{BB}$ together with the atoms to which they are attached form a fused 5- or 6-membered cycloalkyl or heterocyclic bicyclic ring system; and b)

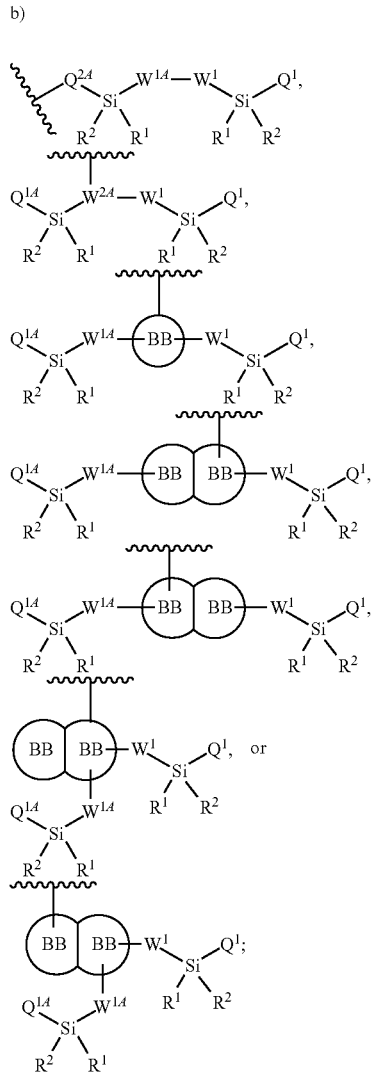

[Group B]

wherein $Q^{2A}$ may be selected from the group consisting of a bond, —O—$C_{1-6}$alkyl-, —N(R')—$C_{1-6}$alkyl-, and —S—$C_{1-6}$alkyl-;

$W^1$, independently for each occurrence, is (a) absent; or (b) selected from the group consisting of —$C_{1-4}$alkyl-, —O—$C_{1-4}$alkyl-, —N(R$^a$)—$C_{1-4}$alkyl-, —$C_{1-4}$alkyl-C(O)—, —C(O)$C_{1-4}$alkyl-, —$C_{1-4}$alkyl-O—C(O)—, —C(O)—O—$C_{1-4}$alkyl-, —NR'—C(O)—, —$C_{2-6}$alkenyl-, —$C_{2-6}$alkynyl-, —$C_{3-6}$cycloalkyl-, -phenyl-, and -heteroaryl-; wherein $C_{1-4}$alkyl, $C_{2-6}$alkenyl, $C_{2-6}$alkynyl, $C_{3-6}$cycloalkyl, R', R$^a$ phenyl and heteroaryl may be optionally substituted independently, for each occurrence, with one, two, three or more substituents selected from the group consisting of $C_{1-4}$alkyl, $C_{1-4}$alkoxy, —C(O)$C_{1-6}$alkyl, —C(O)—O—$C_{1-4}$alkyl, halogen, hydroxyl, nitro, carbamate, carbonate and cyano;

$W^{1A}$, independently for each occurrence, is (a) absent; or (b) selected from the group consisting of —$C_{1-4}$alkyl-, —$C_{1-4}$alkyl-O—, —$C_{1-4}$alkyl-N(R$^a$)—, —$C_{1-4}$alkyl-C(O)—, —C(O)$C_{1-4}$alkyl-, —$C_{1-4}$alkyl-O—C(O)—, —C(O)—O—$C_{1-4}$alkyl-, —C(O)—NR'—, —$C_{2-6}$alkenyl-, —$C_{2-6}$alkynyl-, —$C_{3-6}$cycloalkyl-, -phenyl-, and -heteroaryl-; wherein $C_{1-4}$alkyl, $C_{2-6}$alkenyl, $C_{2-6}$alkynyl, $C_{3-6}$cycloalkyl, R', R$^a$ phenyl and heteroaryl may be optionally substituted independently, for each occurrence, with one, two, three or more substituents selected from the group consisting of $C_{1-4}$alkyl, $C_{1-4}$alkoxy, —C(O)$C_{1-6}$alkyl, —C(O)—O—$C_{1-4}$alkyl, halogen, hydroxyl, nitro, carbamate, carbonate and cyano;

R' may be independently selected, for each occurrence, from the group consisting of hydrogen, substituted or unsubstituted aliphatic, and substituted or unsubstituted heteroaliphatic;

$Q^1$ and $Q^{1A}$ may be independently selected, for each occurrence, from the group consisting of —NHR', —N(R')$_2$, —NR$^a$R$^b$, —O—Si(R')$_3$, —O—SiR$^a$R$^b$R', —SH, —OH, —O—$C_{1-6}$alkyl, —S—$C_{1-6}$alkyl, —O-aryl, —S-aryl, heteroaryl, —O-heteroaryl, —S-heteroaryl, halogen and —O—$C_{1-6}$alkyl-NR$^a$R$^b$;

R$^a$ and R$^b$ may be independently selected, for each occurrence, from the group consisting of hydrogen and $C_{1-4}$alkyl; wherein $C_{1-4}$alkyl may be optionally substituted by one or more substituents selected from the group consisting of halogen, cyano, oxo and hydroxyl; or R$^a$ and R$^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl;

$R^1$ and $R^2$ are selected independently, for each occurrence, from the group consisting of —OH, $C_{1-6}$alkyl, —O—$C_{1-6}$alkyl, $C_{2-6}$alkenyl, $C_{3-6}$cycloalkyl, —$C_{1-6}$alkyl-NR$^a$R$^b$, phenyl and heteroaryl; wherein $C_{1-6}$alkyl, $C_{2-6}$alkenyl, $C_{3-6}$cycloalkyl, R$^a$, R$^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

$W^{2A}$ may be CR$^{W2A}$.

R$^{W2A}$ may be selected from the group consisting of hydrogen, $C_{1-4}$alkyl, —O—$C_{1-4}$alkyl, $C_{2-6}$alkenyl, $C_{2-6}$alkynyl, $C_{3-6}$cycloalkyl, phenyl and heteroaryl; wherein $C_{1-4}$alkyl, $C_{2-6}$alkenyl, $C_{2-6}$alkynyl, $C_{3-6}$cycloalkyl, phenyl and heteroaryl may be optionally substituted independently, for each occurrence, with one, two, three or more substituents selected from the group consisting of halogen, hydroxyl and cyano;

BB, independently for each occurrence, may be a 4-7-membered cycloalkyl, heterocyclic, aryl, or heteroaryl moiety; wherein the cycloalkyl, heterocyclic, aryl, or heteroaryl moiety may be optionally substituted with one, two, three or more groups represented by R$^{BB}$; wherein $R^1$, independently for each occurrence, may be optionally bonded to BB;

each R$^{BB}$ is independently selected, for each occurrence, from the group consisting of hydrogen, halogen, nitro, cyano, hydroxyl, amino, thio, —COOH, —CONHR', substituted or unsubstituted aliphatic, substituted or unsubstituted heteroaliphatic (e.g., —C$_{1-4}$alkyl, —O—C$_{1-4}$alkyl, —N(R$^a$)—C$_{1-4}$alkyl, —C(O)C$_{1-4}$alkyl, —C(O)—O—C$_{1-4}$alkyl, —C(O)—NR$^a$R$^b$, —C$_{2-6}$alkenyl, —C$_{2-6}$alkynyl, —C$_{3-6}$cycloalkyl), heterocyclic, phenyl, phenoxy, heteroaryl, —C$_{1-4}$alkylene-phenyl, —C$_{1-4}$alkylene-heteroaryl, —C$_{1-4}$alkylene-heterocyclyl, —C$_{2-6}$alkenylene-phenyl, —C$_{2-6}$alkenylene-heteroaryl, —C$_{2-6}$alkenylene-heterocyclyl, —C$_{2-6}$alkynyl-phenyl, —C$_{2-6}$alkynyl-heteroaryl, —C$_{2-6}$alkynyl-heterocyclyl; wherein C$_{1-4}$alkyl, C$_{2-6}$alkenyl, C$_{2-6}$alkynyl, C$_{3-6}$cycloalkyl, phenyl and heteroaryl may be optionally substituted by one, two, three or more substituents selected from the group consisting of C$_{1-4}$alkyl, C$_{1-4}$alkoxy, —C(O)C$_{1-4}$alkyl, —C(O)—O—C$_{1-4}$alkyl, —C(O)—NR$^a$R$^b$, halogen, cyano, hydroxyl, cycloalkyl, heterocyclic, phenyl, or heteroaryl, and R$^a$ and R$^b$ are defined herein; or two R$^{BB}$ together with the atoms to which they are attached form a fused 5- or 6-membered cycloalkyl or heterocyclic bicyclic ring system.

In some embodiments, $Z^3$, $Z^2$, and $Z^1$ may be independently selected, for each occurrence, from Group A; wherein $W^1$ independently, for each occurrence, may be absent or selected from the group consisting C$_{1-4}$alkyl or phenyl; wherein BB may be selected independently, for each occurrence, from phenyl or heteroaryl; and wherein R$^1$ and R$^2$ may be independently selected, for each occurrence, from methyl or —OH; and wherein Q$^1$ may be —OH. For example, R$^2$ and Q$^1$ may be —OH.

In other embodiments, $Z^3$, $Z^2$, and $Z^1$ may be independently selected, for each occurrence, from the group consisting of:

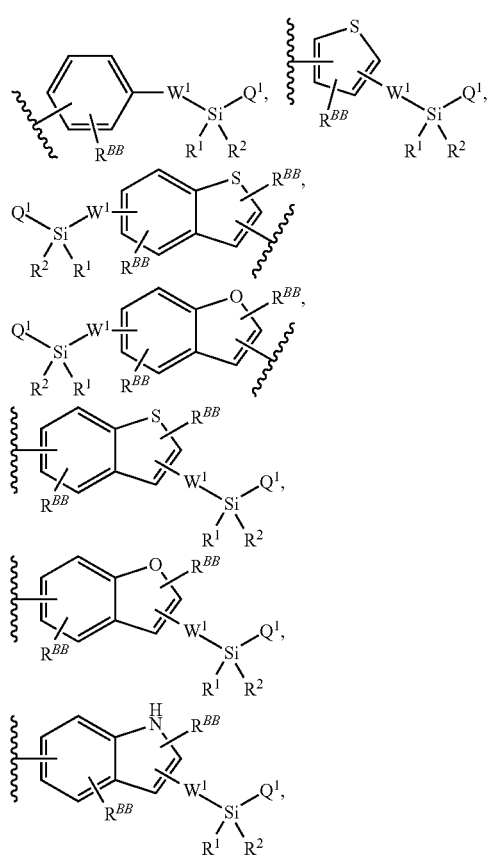

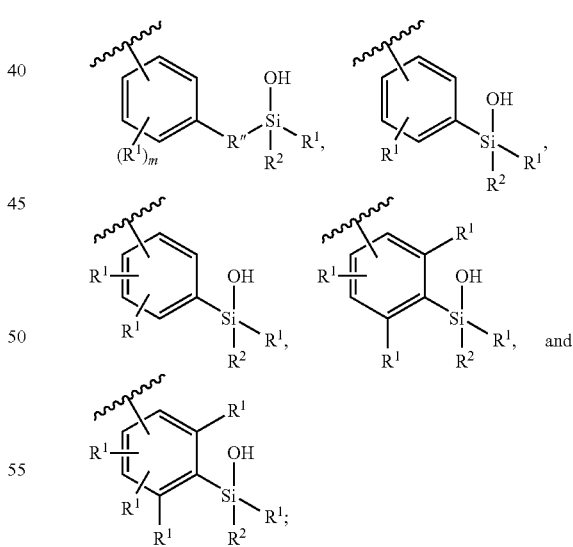

wherein
R$^{BB}$ is independently selected, for each occurrence, from the group consisting of hydrogen, halogen, nitro, cyano, hydroxyl, amino, thio, —COOH, —CONHR', substituted or unsubstituted aliphatic, and substituted or unsubstituted heteroaliphatic;

W$^1$, independently selected for each occurrence, is (a) absent or (b) —C$_{1-4}$ alkyl-;

Q$^1$ is independently selected for each occurrence from the group consisting of —NHR', —N(R')$_2$, —NR$^a$R$^b$, —O—Si(R')$_3$, —O—SiR$^a$R$^b$R', —SH, —OH, —O—C$_{1-6}$alkyl, —S—C$_{1-6}$alkyl, —O-aryl, —S-aryl, heteroaryl, —O-heteroaryl, —S-heteroaryl, halogen and —O—C$_{1-6}$alkyl-NR$^a$R$^b$;

R$^1$ and R$^2$, independently selected, for each occurrence, may be C$_{1-6}$alkyl.

In certain embodiments, $Z^3$ $Z^2$, and $Z^1$ may be independently selected, for each occurrence, from the group consisting of:

wherein
R$^1$ and R$^2$ are selected independently, for each occurrence, from the group consisting of —OH, C$_{1-6}$alkyl, —O—C$_{1-6}$alkyl, C$_{2-6}$alkenyl, C$_{3-6}$cycloalkyl, —C$_{1-6}$alkyl-NR$^a$R$^b$, phenyl and heteroaryl; wherein C$_{1-6}$alkyl, C$_{2-6}$alkenyl, C$_{3-6}$cycloalkyl, R$^a$, R$^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

$R^a$ and $R^b$ are independently selected, for each occurrence, from the group consisting of hydrogen and $C_{1-4}$alkyl; wherein $C_{1-4}$alkyl may be optionally substituted by one or more substituents selected from the group consisting of halogen, cyano, oxo and hydroxyl; or $R^a$ and $R^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl; and m is 0, 1, 2, 3 or 4.

In another embodiment, $Z^3$, $Z^2$, and $Z^1$ may be independently selected, for each occurrence, from the group consisting of:

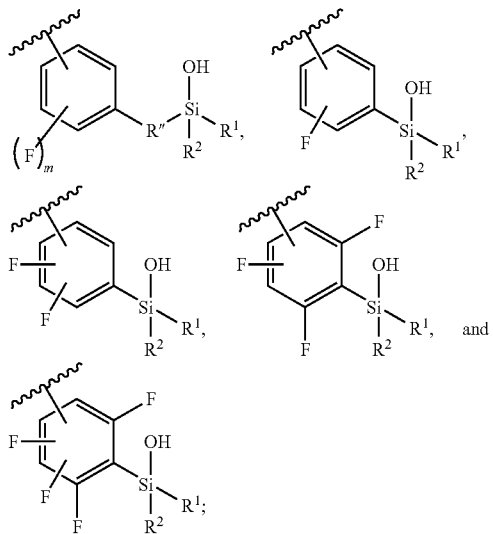

wherein $R^1$ and $R^2$, independently selected, for each occurrence, from the group consisting of $C_{1-6}$alkyl and $C_{1-6}$alkoxy;

m is 0, 1, 2, 3 or 4;

R" is selected from the group consisting of —$C_{1-2}$alkyl-, —O—$C_{1-2}$alkyl-, and —NH(C=O)$C_{1-2}$alkyl; wherein $C_{1-2}$alkyl is optionally substituted independently, for each occurrence, with one, two, three or more fluorines.

In some embodiments, $Z^3$, $Z^2$, and $Z^1$ may be independently selected, for each occurrence, from Group B; wherein $W^1$ and $W^{1A}$ independently, for each occurrence, may be absent or $C_{1-4}$alkyl; and wherein BB may be selected independently, for each occurrence, from phenyl or heteroaryl. For example, $W^1$ may be —$C_{1-4}$alkyl- and $W^{1A}$ may be absent. Alternatively, $W^1$ and $W^{1A}$ may be —$C_{1-4}$alkyl-. In some embodiment, $W^1$ and $W^{1A}$ may be absent. For example BB may be selected from the group consisting of

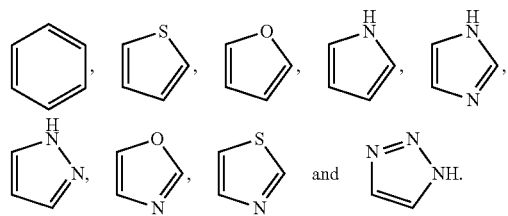

In a certain embodiment, $Z^3$, $Z^2$, and Z may be independently selected, for each occurrence, from the group consisting of:

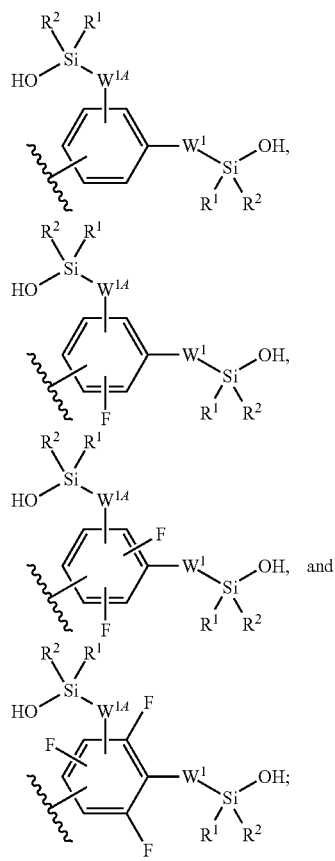

wherein $W^1$ and $W^{1A}$, independently selected, for each occurrence, are (a) absent or (b) —$C_{1-4}$alkyl-;

$R^1$ and $R^2$ are selected independently, for each occurrence, from the group consisting of —OH, $C_{1-6}$alkyl, —O—$C_{1-6}$alkyl, $C_{2-6}$alkenyl, $C_{3-6}$cycloalkyl, —$C_{1-6}$alkyl-$NR^aR^b$, phenyl and heteroaryl; wherein $C_{1-6}$alkyl, $C_{2-6}$alkenyl, $C_{3-6}$cycloalkyl, $R^a$, $R^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

$R^a$ and $R^b$ are independently selected, for each occurrence, from the group consisting of hydrogen and $C_{1-4}$alkyl; wherein $C_{1-4}$alkyl may be optionally substituted by one or more substituents selected from the group consisting of halogen, cyano, oxo and hydroxyl; or $R^a$ and $R^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl; and m is 0, 1, 2, 3 or 4.

In another embodiment, $Z^3$, $Z^2$, and $Z^1$ may be independently selected, for each occurrence, from the group consisting of:

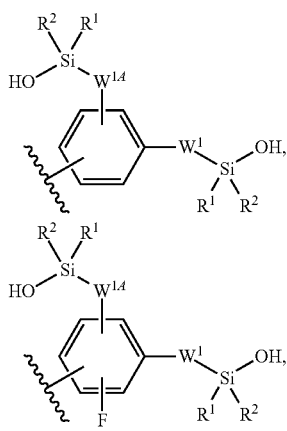

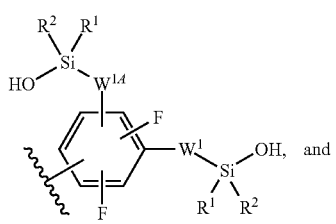

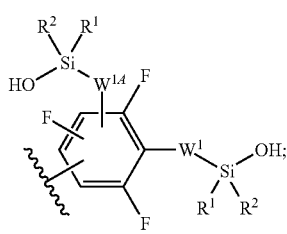

wherein $W^1$ and $W^{1A}$, independently selected, for each occurrence, are (a) absent or (b) —$C_{1-4}$alkyl-;

$R^1$ and $R^2$, independently selected, for each occurrence, are selected from the group consisting of $C_{1-6}$alkyl and —O—$C_{1-6}$alkyl.

In certain embodiments, $Z^2$ may be independently selected, for each occurrence, from the group consisting of:

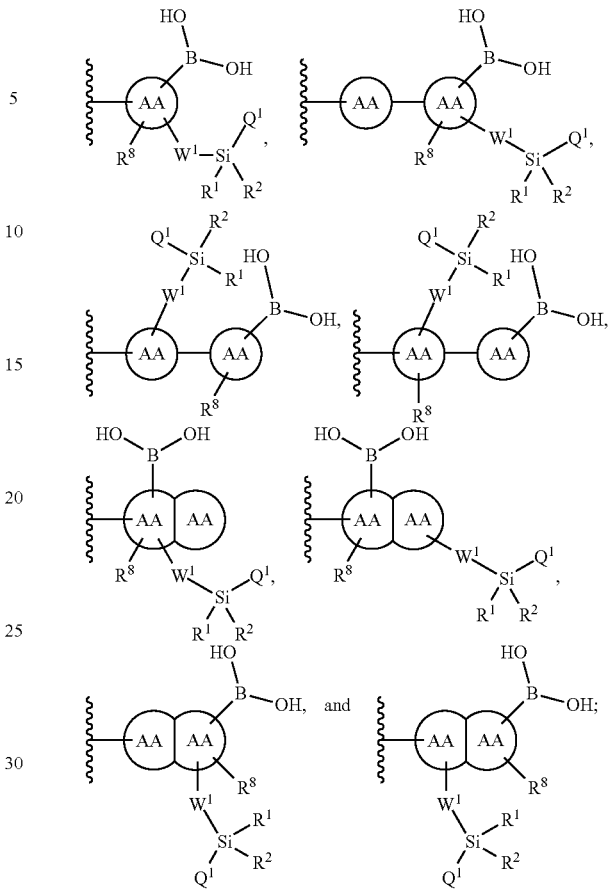

wherein $W^1$, independently for each occurrence, is (a) absent; or (b) selected from the group consisting of —$C_{1-4}$alkyl-, —O—$C_{1-4}$alkyl-, —$C_{1-4}$alkyl-C(O)—, —C(O)—$C_{1-4}$alkyl-, —N($R^a$)—$C_{1-4}$alkyl-, —$C_{1-4}$alkyl-O—C(O)—, —C(O)—O—$C_{1-4}$alkyl-, —$NR^a$—C(O)—, —$C_{2-6}$alkenyl-, —$C_{2-6}$alkynyl-, —$C_{3-6}$cycloalkyl-, -phenyl-, -heteroaryl-, and heterocyclic; wherein $C_{1-4}$alkyl, $C_{2-6}$alkenyl, $C_{2-6}$alkynyl, $C_{3-6}$cycloalkyl, R', phenyl, heterocyclic, and heteroaryl are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

R' is independently selected, for each occurrence, from the group consisting of hydrogen, substituted or unsubstituted aliphatic, and substituted or unsubstituted heteroaliphatic;

$Q^1$ is independently selected, for each occurrence, from the group consisting of —NHR', —N(R')$_2$, —$NR^aR^b$, —O—Si(R')$_3$, —O—Si$R^aR^b$R', —SH, —OH, —O—$C_{1-6}$alkyl, —S—$C_{1-6}$alkyl, —O-aryl, —S-aryl, heteroaryl, —O-heteroaryl, —S-heteroaryl, halogen and —O—$C_{1-6}$alkyl-$NR^aR^b$;

$R^a$ and $R^b$ are independently selected, for each occurrence, from the group consisting of hydrogen and $C_{1-4}$alkyl;

wherein $C_{1-4}$alkyl may be optionally substituted by one or more substituents selected from the group consisting of halogen, cyano, oxo and hydroxyl; or $R^a$ and $R^b$, together with the nitrogen to which they are attached, may form a 4-7 membered heterocyclic ring, which may have an additional heteroatom selected from O, S, or N; wherein the 4-7 membered heterocyclic ring may be optionally substituted by one or more substituents selected from the group consisting of halogen, cyano, oxo and hydroxyl;

$R^1$ and $R^2$ are selected independently, for each occurrence, from the group consisting of —OH, $C_{1-6}$alkyl, —O—$C_{1-6}$alkyl, $C_{2-6}$alkenyl, $C_{3-6}$cycloalkyl, —$C_{1-6}$alkyl-$NR^aR^b$, phenyl and heteroaryl; wherein $C_{1-6}$alkyl, $C_{2-6}$alkenyl, $C_{3-6}$cycloalkyl, $R^a$, $R^b$, phenyl and heteroaryl, independently selected, for each occurrence, may be optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 5-8 membered heterocyclic ring, which may have one or more additional heteroatoms selected from O, S, or N; wherein the 5-8 membered heterocyclic ring may be optionally substituted by one or more substituents selected from the group consisting of halogen, cyano, oxo, amino and hydroxyl;

$R^8$, independently for each occurrence, is selected from the group consisting of H, halogen, oxo and $C_{1-4}$alkyl; wherein $C_{1-4}$alkyl is optionally substituted by one or more substituents selected from the group consisting of hydroxyl, amino, halo, thio. $C_{2-4}$alkenyl, $C_{1-4}$alkoxy, —S—$C_{1-4}$alkyl, —CN, —COOH and —C(O)—NHR";

AA, independently for each occurrence, is a 5-7 membered heterocyclic ring having one, two, or three heteroatoms, or phenyl; wherein AA is optionally substituted by one, two, or three substituents selected from the group consisting of halo and $C_{1-4}$alkyl; wherein $C_{1-4}$alkyl is optionally substituted by one or more substituents selected from the group consisting of hydroxyl, amino, halo, thio. $C_{2-4}$alkenyl, $C_{1-4}$alkoxy, —S—$C_{1-4}$alkyl, —CN, —COOH and —C(O)—NHR", or two substituents together with the atoms to which they are attached form a fused 5- or 6-membered cycloalkyl or heterocyclic bicyclic ring system; and R" is selected independently, for each occurrence, from the group consisting of H and $C_{1-4}$alkyl.

In some cases, the first monomer may form a biologically useful multimer when in contact with one, two, three or more second monomers in vivo. For example, the multimer may be a biologically useful dimer when the first monomer is in contact with the second monomer. Alternatively, the multimer may be a biologically useful trimer when the first monomer is in contact with two second monomers. In other instances, the multimer may be a biologically useful cyclic tetramer when the first monomer is in contact with three second monomers.

As discussed above, the ligand moiety may be a pharmacophore and the target biomolecule may be a protein target. In some cases, the first target biomolecule and the second target biomolecule may be the same. In other cases, the first target biomolecule and the second target biomolecule may be different. For example, the first target biomolecule may be a ribosome. In another embodiment, the first target biomolecule may be a tryptase. Alternatively, the second target biomolecule may be a ribosome. In another embodiment, the second target biomolecule may be a tryptase.

In other cases, $X^1$ may be a non-peptidyl ligand moiety. In some instances, $X^2$ may be a non-peptidyl ligand moiety. In one embodiment, $X^1$ and $X^2$ may be the same. In another embodiment, $X^1$ and $X^2$ may be the different.

In some embodiments, the effects of the multimer formed from the monomers may be greater than the sum of the effects of the individual monomers. For example, the ratio of the smaller of the apparent $IC_{50}$ of the first monomer or the second monomer to the apparent $IC_{50}$ of the multimer may be at least 3.0, 10.0 or 30.0.

In certain embodiments, the first monomer and the second monomer may reversibly associate to form the multimer.

As discussed above, a monomer may be capable of reacting with one or more other monomers to form a multimer in an aqueous composition, e.g. in vivo. In some embodiments, a first monomer may react with a second monomer to form a dimer. In other embodiments, a first monomer may react with two second monomers to form a trimer. In still other embodiments, a first monomer may react with three second monomers to form a cyclic tetramer. In some embodiments, each of the monomers that form a multimer may be essentially the same. In some embodiments, each of the monomers that form a multimer may be substantially different. In certain embodiments, at least some of the monomers that form a multimer may be essentially the same or may be substantially different.

In some embodiments, the linker element of a first monomer and the linker element of a second monomer may be substantially different. In other embodiments, the connector element of a first monomer and the connector element of a second monomer may be substantially different. In still other embodiments, the ligand moiety (e.g., pharmacophore) of a first monomer and the ligand moiety (e.g. pharmacophore) of the second monomer may be substantially different.

In some cases, formation of a multimer from a plurality of monomers may be irreversible. In some embodiments, formation of a multimer from a plurality of monomers may be reversible. For example, in some embodiments, the multimer may have an oligomer or dimer dissociation constant between 10 mM and 1 nM, in some embodiments between 1 mM and 100 nM, in some embodiments between 1 mM and 1 μM, and in some embodiments between 500 mM and 1 μM. In certain embodiments, the multimer may have a dissociation constant of less than 10 mM, in some embodiments less than 1 mM, in some embodiments less than 500 μM, in some embodiments less than 100 μM, in some embodiments less than 50 μM, in some embodiments less than 1 μM, in some embodiments less than 100 nM, and in some embodiments less than 1 nM.

While the affinity of the multimer for its target biomolecule(s) often cannot be measured directly due to the dynamic reversible equilibrium with its monomers in an aqueous or biological milieu, it may be possible to extract an apparent multimer-target dissociation constant from a series of experimental determinations. Exploring the effects of a matrix of monomer concentrations, monomer ratios, along with changes in concentration(s) in the target biomolecule(s), coupled with determinations of multimer-monomer dissociation constants, and in some cases additional binding competition, kinetic and biophysical methods, one can extract an estimate of the affinity of the multimeric assembly for its target(s). Through such approaches, one can demonstrate that in some embodiments, the affinity of the multimer for the target biomolecule(s) are less than 1 μM, in some embodiments less than 1 nM, in some embodiments less than 1 pM, in some embodiments less than 1 fM, and in some embodiments less than 1 aM, and in some embodiments less than 1 zM.

Multimers

Without wishing to be bound by any theory, it is believed that molecular self-assembly may be directed through non-covalent interactions, e.g., hydrogen bonding, metal coordination, hydrophobic forces, van der Waals forces, pi-pi interactions, electrostatic, and/or electromagnetic interactions.

Without wishing to be bound by any theory, pi-pi and pi-cation interactions can be used to drive multimerization. In addition, van der Waals and electromagnetic forces are other interactions that can help to drive multimerization. Alternatively, acid/base pairs and donor-acceptor pairs, e.g., amide and/or sulfonamide pairs, can be employed to help direct self-assembly. In other cases, use of hydrophobic interactions can be used for multimerization targeting a membrane-bound protein. Additionally, metal coordination might be used when the target itself incorporates the metal, but could also be used in other scenarios.

In some embodiments, a first monomer and a second monomer may form a dimer in aqueous solution. For example, in some instances, the first monomer may form a biologically useful dimer with a second monomer in vivo.

In another embodiment, a therapeutic multimer compound may form from the multimerization in an aqueous media of a first monomer $X^3-Y^3-Z^3$ with a second monomer $X^3-Y^3-Z^3$.

In certain embodiments, a therapeutic multimer compound may form from the multimerization in an aqueous media of the first monomer represented by:

$$X^1-Y^1-Z^1 \quad \text{(Formula I),}$$

and pharmaceutically acceptable salts, stereoisomers, metabolites and hydrates thereof, and the second monomer represented by:

$$X^2-Y^2-Z^2 \quad \text{(Formula II),}$$

and pharmaceutically acceptable salts, stereoisomers, metabolites and hydrates thereof.

For example, $X^1$ is a first ligand moiety capable of binding to and modulating a first target biomolecule; $Y^1$ is absent or is a connector moiety covalently bound to $X^1$ and $Z^1$; $Z^1$ is independently selected from the groups discussed above; $X^2$ is a second ligand moiety capable of binding to and modulating a second target biomolecule; $Y^2$ is absent or is a connector moiety covalently bound to $X^2$ and $Z^2$; $Z^2$ is is independently selected from the groups discussed above.

In some embodiments, $X^1$ and $X^2$ may be the same. In other cases, $X^1$ and $X^2$ may be different.

Disiloxanes

Without wishing to be bound by any theory, the estimated half-life for hydrolysis of the disiloxane depicted here:

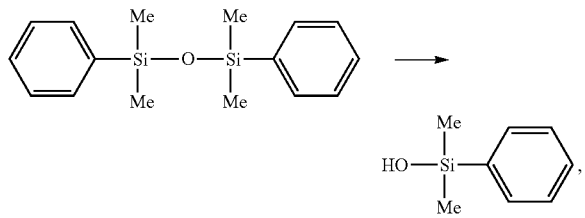

is 15 days based at pH5 in 90% DMSO/10% water at room temperature based upon NMR experiments. Based on the effect of alkyl group size on silyl ether hydrolysis, the half-life of hydrolysis of the corresponding diphenyltetraethyldisiloxane is expected to be more than ten fold longer.

Thus in certain aqueous situations, the hydrolysis of the dimeric disiloxane to monomeric silanol may be essentially irreversible on the timescale relevant for the biological functions they are modulating.

In another embodiment, the stability of a disiloxane linkage to attack on silicon may be influenced by steric hindrance. Alkyl groups on silicon of increasing size (e.g. Me<Et<iPr<tBu) can promote disiloxane stability once formed, while at the same time reducing the probability and rate of dimerization of the silanol when two monomers are not held in close proximity.

An alternative approach to increasing steric hindrance about silicon is depicted here:

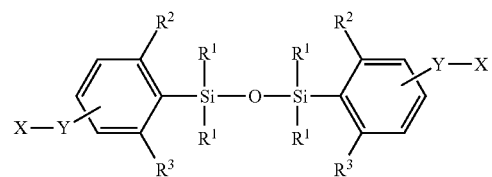

Increasing steric hindrance about silicon may relate to homo- or hetero-dimeric designs where Y and X are the connector and ligand/pharmacophore moieties, respectively. Alternatively, $-Y-X$ could be connected through the respective R-groups. Importantly, the nature of these groups can also influence the stability of the disiloxy dimer and the rate of dimerization to allow one to tune the properties.

In some instances, the incorporation of the silicon in a ring system allows for steric hindrance by flanking substituents rather than directly upon Si. Examples of two disiloxanes are depicted here:

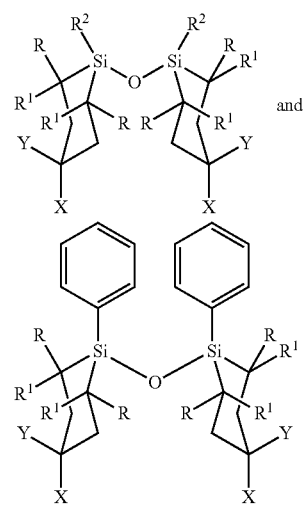

In these examples, selectivity and complementarity can be further increased in designs such as those below where the individual $R^2$ component in a heterodimeric pairing may be electron-rich and electron-poor aromatic or heteroaromatic rings, such that the result quadrupole interactions stabilize the alignment and association of monomers, and promote the dimerization of hindered silanols to the disiloxane (e.g. where $R^3$ substituents are electron withdrawing, producing a group like $C_6F_5$, while $R^4$ may be electron donating or H for a simple phenyl). In a similar manner, other donor-acceptor interactions such as cation (e.g. aminium)/aromatic systems may be employed to promote association, alignment and dimerization.

Connectors

In some embodiments, a monomer may comprise a connector that joins the ligand moiety with the linker element. In some instances, such connectors do not have significant binding or other affinity to an intended target. However, in certain embodiments, a connector may contribute to the affinity of a ligand moiety to a target.

In some embodiments, a connector element may be used to connect the linker element to the ligand moiety. In some instances, the connector element may be used to adjust spacing between the linker element and the ligand moiety. In some cases, the connector element may be used to adjust the orientation of the linker element and the ligand moiety. In certain embodiments, the spacing and/or orientation the linker element relative to the ligand moiety can affect the binding affinity of the ligand moiety (e.g., a pharmacophore) to a target. In some cases, connectors with restricted degrees of freedom are preferred to reduce the entropic losses incurred upon the binding of a multimer to its target biomolecule. In some embodiments, connectors with restricted degrees of freedom are preferred to promote cellular permeability of the monomer.

In some embodiments, the connector element may be used for modular assembly of monomers. For example, in some instances, a connector element may comprise a functional group formed from reaction of a first and second molecule. In some cases, a series of ligand moieties may be provided, where each ligand moiety comprises a common functional group that can participate in a reaction with a compatible functional group on a linker element. In some embodiments, the connector element may comprise a spacer having a first functional group that forms a bond with a ligand moiety and a second functional group that forms a bond with a linker element.

Contemplated connectors may be any acceptable (e.g. pharmaceutically and/or chemically acceptable) bivalent linker that, for example, does not interfere with multimerization of the disclosed monomers. For instance, such linkers may be substituted or unsubstituted $C_1$-$C_{10}$ alkylene, substituted or unsubstituted cycloalkylene, substituted or unsubstituted aryl, substituted or unsubstituted heteroaryl, acyl, sulfone, sulfonamide, phosphate, ester, carbonate, carbamate, or amide. Contemplated connectors may include polymeric connectors, such a polyethylene glycol or other pharmaceutically acceptable polymers. For example, contemplated connectors may be a covalent bond or a bivalent $C_{1-10}$ saturated or unsaturated, straight or branched, hydrocarbon chain, wherein one, two, or three or four methylene units of bivalent $C_{1-10}$ are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, phenyl, or a mono or bicyclic heterocycle ring. In some embodiments, a connector may be from about 7 atoms to about 13 atoms in length, or about 8 atoms to about 12 atoms, or about 9 atoms to about 11 atoms in length. For purposes of counting connector length when a ring is present in the connector group, the ring is counted as three atoms from one end to the other. In another embodiment, a connecter group is from about 6 Å to about 15 Å in length.

Methods

In some embodiments, a method of administering a pharmaceutically effective amount of a multimeric compound to a patient in need thereof is provided. In some cases, the method comprises administering to the patient thereof an amount of the first monomer and an amount of the second monomer in amounts effective such that the pharmaceutically effective amount of the resulting multimer is formed in vivo. For example, the multimer may be a dimer. Alternatively, the multimer may be a trimer.

In some embodiments, a first monomer and a second monomer may be administered substantially sequentially. In other embodiments, the first monomer and the second monomer are administered substantially simultaneously. In some embodiments the monomers may be administered, sequentially or simultaneously, by different routes of administration. In still further embodiments, a first monomer and a second monomer may be administered after forming a multimer.

In some instances, a method of modulating two or more target biomolecule domains substantially simultaneously is provided. The method comprises contacting an aqueous composition comprising said biomolecular target domain with a first monomer represented by:

$$X^1—Y^1—Z^1 \quad \text{(Formula I)},$$

and pharmaceutically acceptable salts, stereoisomers, metabolites and hydrates thereof, wherein $X^1$ is a first ligand moiety capable of binding to and modulating a first target biomolecule domain; and a second monomer represented by:

$$X^2—Y^2—Z^2 \quad \text{(Formula II)},$$

and pharmaceutically acceptable salts, stereoisomers, metabolites and hydrates thereof, wherein $X^2$ is a ligand moiety capable of binding to and modulating a second target biomolecule domain;

wherein upon contact with the aqueous composition, said first monomer and said second monomer forms a multimer that binds to the first target biomolecule domain and the second target biomolecule domain.

In certain embodiments, a method of treating a disease associated with two or more target biomolecules in a patient in need thereof is provided. The method comprises administering to said patient a first monomer represented by:

$$X^1—Y^1—Z^1 \quad \text{(Formula I)},$$

and pharmaceutically acceptable salts, stereoisomers, metabolites and hydrates thereof, wherein $X^1$ is a first ligand moiety capable of binding to and modulating a first target biomolecule domain; and administering to said patient a second monomer represented by:

$$X^2—Y^2—Z^2 \quad \text{(Formula II)},$$

wherein $X^2$ is a second ligand moiety capable of binding to and modulating a second target biomolecule domain, wherein upon administration, said first monomer and said second monomer forms a multimer in vivo that binds to the first target biomolecule domain and the second target biomolecule domain.

In some embodiments, the target biomolecule may be a protein. Alternatively, the target biomolecule may be a protein domain. In other embodiments, the target biomolecule may be nucleic acid. In some cases, the ligand moiety (e.g., ligand moiety) may be a pharmacophore.

In some embodiments, a multimer may be used to inhibit or facilitate protein-protein interactions. For example, in some cases, a multimer may be capable of activating or inactivating a signaling pathway. Without wishing to be bound by any theory, a multimer may bind to a target protein and affect the conformation of the target protein such that the target protein is more biologically active as compared to when the multimer does not bind the target protein. In some embodiments monomers may be chosen such that a multimer formed from the monomers binds to at least two regions of a target molecule.

In certain embodiments, the compounds may be selected from the group consisting of: (4-(3-(aminomethyl)phenyl) piperidin-1-yl)(4-((hydroxydimethylsilyl)methoxy)-phenyl) methanone; N-(4-(4-(3-(aminomethyl)phenyl)-piperidine-1-carbonyl)-2-chlorophenyl)-2-(hydroxydimethylsilyl) acetamide; N-(3-(4-(3-(aminomethyl)phenyl)piperidine-1-carbonyl)-phenyl)-2-(hydroxydimethylsilyl)acetamide; (4-(3-(aminomethyl)phenyl)piperidin-1-yl)(3-chloro-4-((hydroxydimethylsilyl)methoxy)-phenyl)methanone; (4-(3-(aminomethyl)phenyl)-piperidin-1-yl)(3-((hydroxydimethylsilyl)-methoxy)phenyl)methanone; (4-(3-(aminomethyl)-phenyl)piperidin-1-yl)(3-chloro-5-((hydroxydimethylsilyl)methoxy)phenyl)methanone; N-(4-(4-(3-(aminomethyl)phenyl)-piperidine-1-carbonyl) phenyl)-2-(hydroxydimethylsilyl)acetamide; and pharmaceutically acceptable salts, stereoisomers, metabolites and hydrates thereof.

Without wishing to be bound by any theory, protein-protein and protein-nucleic acid recognition often work through protein interaction domains, such as the SH2, SH3, and PDZ domains. Currently, there are over 75 such motifs reported in the literature (Hunter, et al., *Cell* 100:113-127 (2000); Pawson et al., *Genes & Development* 14:1027-1047 (2000)). For example, SH2 domains are miniature receptors for protein regions containing a phosphorylated tyrosine. SH2 domains may be found in proteins that act as, or play a role in, for example, adaptors, scaffolds, kinases, phosphatases, ras signalling, transcription, ubiquitination, cytoskeletal regulation, signal regulation, and phospholipid second messenger signaling. As another non-limiting example, SH3 domains bind peptide loops with the motif RXXK or PXXP. Many proteins have both SH2 and SH3 domains, which act as "receptors" to bind one or more protein partners. Coferons may be designed to inhibit binding of a phosphotyrosine protein to its cognate SH2 domain. Alternatively, monomers and multimers may be designed so one ligand binds one motif (i.e. SH2), and a second ligand moiety binds a second motif (i.e. SH3), either on the same or different proteins.

Many large proteins or macromolecular complexes (e.g., ribosomes) have multiple binding sites with known drug inhibitors. In some embodiments, linker elements may be used to bring together two pharmacophores on the same target to: (i) bind the target with higher affinity; (ii) exhibit a stronger inhibition than either pharmacophore alone; (iii) exhibit greater activation than either pharmacophore alone; or (iv) create a binding entity covering a larger surface area of the target, making it harder for the organism/cell/virus to develop resistance to the drug via point mutations.

In some embodiments, a multimer may target a tryptase. For example, a multimer may be used to treat conditions activated by a trypase, such as mast cell mediated inflammatory conditions (e.g. asthma). Asthma is frequently characterized by progressive development of hyper-responsiveness of the trachea and bronchi to both immunospecific allergens and generalized chemical or physical stimuli, which lead to the onset of chronic inflammation. Leukocytes containing IgE receptors, notably mast cells and basophils, are present in the epithelium and underlying smooth muscle tissues of bronchi. These leukocytes initially become activated by the binding of specific inhaled antigens to the IgE receptors and then release a number of chemical mediators. For example, degranulation of mast cells leads to the release of proteoglycans, peroxidase, arylsulfatase B, chymase, and tryptase, which results in bronchiole constriction.

Human mast cell β-tryptase-II is a tetrameric serine protease that is concentrated in mast cell secretory granules. The enzyme is involved in IgE-induced mast cell degranulation in an allergic response and is potentially a target for the treatment of allergic asthma, rhinitis, conjunctivitis and dermatitis. Tryptase has also been implicated in the progression of renal, pulmonary, hepatic, testicular fibrosis, chronic obstructive pulmonary disease (COPD) and inflammatory conditions such as ulcerative colitis, inflammatory bowel disease, rheumatoid arthritis, and various other mast cell-related diseases. In some embodiments, multimers may be used to treat such diseases.

Tryptase is stored in the mast cell secretory granules and is the major protease of human mast cells. Tryptase has been implicated in a variety of biological processes, including degradation of vasodilatory and bronchodilatory neuropeptides and modulation of bronchial responsiveness to histamine. As a result, tryptase inhibitors may be useful as anti-inflammatory agents for treatment of inflammatory disease and may also be useful in treating or preventing allergic rhinitis, inflammatory bowel disease, psoriasis, ocular or vernal or ulcerative conjunctivitis, dermatological conditions (e.g., psoriasis, eczema, or atopic dermatitis), arthritis (e.g., rheumatoid arthritis, osteoarthritis, hematoid arthritis, traumatic arthritis, rubella arthritis, psoriatic arthritis, or gouty arthritis), rheumatoid spondylitis, interstitial lung disease, chronic obstructive pulmonary disease, and diseases of joint cartilage destruction.

In addition, tryptase has been shown to be a potent mitogen for fibroblasts, suggesting its involvement in the pulmonary fibrosis in asthma and interstitial lung diseases. Therefore, in some embodiments, tryptase inhibitors may be useful in treating or preventing fibrotic conditions, for example, fibrosis, sceleroderma, pulmonary fibrosis, liver cirrhosis, myocardial fibrosis, neurofibromas, hepatic fibrosis, renal fibrosis, testicular, and hypertrophic scars.

Additionally, tryptase inhibitors may be useful in treating or preventing myocardial infarction, stroke, angina and other consequences of atherosclerotic plaque rupture.

Tryptase has also been discovered to activate prostromelysin that in turn activates collagenase, thereby initiating the destruction of cartilage and periodontal connective tissue, respectively. In some embodiments, tryptase inhibitors may be useful in the treatment or prevention of arthritis, periodontal disease, diabetic retinopathy, a condition relating to atherosclerotic plaque rupture, anaphylatis ulcerative colitis, and tumour growth. Also, tryptase inhibitors may be useful in the treatment of anaphylaxis, multiple sclerosis, peptic ulcers, and syncytial viral infections.

A variety of antibiotics elicit their antibacterial activity by binding to the bacterial ribosome and inhibiting protein synthesis. Many of these antibiotics bind the peptidyl transferase center of the ribosome (P site). In some embodiments, a multimer may bind to two or more sites on the ribosome. For example, a first pharmacophore of a multimer may bind to the peptidyl transferase center of the ribosome (i.e., the P site) and a second multimer may bind to site adjacent to the P site. As a non-limiting, illustrative example, Linezolid, an oxazolidinone antibiotic, is believed to bind adjacent to the binding site for Sparsomycin. The close juxtaposition of the linezolid binding site with the sparosmycin binding site presents a possible scenario for developing monomers based on linezolid and sparsomycin that can dimerize on binding to the ribosome, thereby creating a high affinity and high specificity inhibitor of bacterial protein synthesis.

Other non-limiting examples of target protein families are provided in Table 1 below. Also provided in Table 1 are endogenous ligands, agonists, and antagonists that bind to the protein families. Examples of detection assays are also provided in Table 1, which may be used in a screening assay to detect activation and/or inhibition of the target protein.

Provided in Table 2 are non-limiting examples of domains that can bind a ligand, proteins that contain the domains, known inhibitors, and $K_D$ values of binding partners (i.e., ligands). Examples of detection assays are also provided in Table 2, which may be used in a screening assay to find ligands for the domains.

TABLE 1

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| G-PROTEIN COUPLED RECEPTORS | $\beta_2$ adrenergic receptors | epinephrine, norepinephrine | albuterol, salbutamol, terbutaline, salmeterol | propranolol, butoxamine | HitHunter, PathHunter (DiscoverX), cAMP assay, Intracellular calcium flux, TANGO, GeneBlazer, ELISA, binding assays |
| G-PROTEIN COUPLED RECEPTORS | Muscarinic receptors | Acetylcholine | Acetylcholine, Pilocarpine | Scopolamine, atropine, ipratropium, caproctamine | HitHunter, PathHunter (DiscoverX), cAMP assay, Intracellular calcium flux, TANGO, GeneBlazer, ELISA, binding assays |
| G-PROTEIN COUPLED RECEPTORS | H1 histamine receptor | histamine | Histamine | diphenhydramine, doxylamine, pyrilamine, brompheniramine, chlorpheniramine, Loratadine, Fexofenadine, Cetirizine, Desloratadine | HitHunter, PathHunter (DiscoverX), cAMP assay, Intracellular calcium flux, TANGO, GeneBlazer, ELISA, binding assays |
| NUCLEAR RECEPTORS | Estrogen receptor | Estriol, estrone, estradiol | 17-beta-estradiol, Chlorotrianisene, Dienestrol, Fosfestrol, Diethylstilbestrol, Zeranol | Tamoxifen, ICI 164,384, Keoxifene, Mepitiostane | Hit-hunter (Discoverx), reporter assays, TANGO, GeneBlazer, ELISA, ligand binding assays, |
| VOLTAGE GATED ION CHANNELS | voltage-gated sodium channels | | veratridine, aconitine | tetrodotoxin, saxitoxin, | Intracellular ion flux assays |
| VOLTAGE GATED ION CHANNELS | voltage-gated calcium channels | | BAY K 8644, CGP 28392 | ω-conotoxin, ω-agatoxins, dihydropyridine, nifedipine | Intracellular ion flux assays |
| LIGAND GATED ION CHANNELS | kainate receptor | glutamate | kainic acid, domoic acid, LY339434, ATPA, iodowillardiine, (2S,4R)-4-methylglutamic acid | CNQX, LY293558, LY294486 | HitHunter, PathHunter (DiscoverX), cAMP assay, Intracellular ion flux, TANGO, GeneBlazer, ELISA, ligand binding assays, |
| RECEPTOR TYROSINE KINASES | epidermal growth factor receptor (EGFR) | epidermal growth factor | EGF, TGFa, amphiregulin, betacellulin, epiregulin, neuregulins | PD153035, anti-EGFR antibody C225, aeroplysinin-1, AG18, AG82, AG99, AG112, AG213, AG490, AG494, AG527, AG555, AG556 | reporter assays, kinase assays, CO-IP, BRET, FRET, TANGO, GeneBlazer, HitHunter, PathHunter (DiscoverX), ELISA |
| GROWTH FACTORS | Vascular endothelial growth factor | VEGFR | | Ranibizumab, bevacizumab, sunitinib, sorafenib, axitinib, pazopanib, Naphthamides | Hit-hunter (Discoverx), reporter assays, TANGO, GeneBlazer, ELISA, ligand binding assays, |
| PROTEASES | Caspase | granzyme B; caspase | Granzyme B, caspase | Z-VAD(OMe)-FMK, Z-VAD-CHO | caspase assays, apoptosis assays, mitochondrial Dy, CO-IP, BRET, FRET, TANGO, GeneBlazer, HitHunter, PathHunter (DiscoverX), ELISA |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| PHOSPHATASES | PP1 | phosphoserine/threonine residues | | calyculin A, nodularin, tautomycin | protein tyrosine phosphatase assay, CO-IP, BRET, FRET, TANGO, GeneBlazer, HitHunter, PathHunter (DiscoverX), ELISA |
| PROTEIN KINASES | ERR | MEK | | AG126, apigenin, Ste-MPKKKPTPTQL NP-NH2 (SEQ ID NO: 1) H-GYGRKKRRQR RR-G-MPKKKPTPIQL NP-NH2 (SEQ ID NO: 2) PD98059, U0126, | kinase assay, CO-IP, BRET, FRET, reporter assays, TANGO, GeneBlazer, HitHunter, PathHunter (DiscoverX) |
| MISC ENZYMES | Adenylate cyclase | G proteins, calcium | *bordetella pertussis*, cholera toxin, forskolin | NKY80, 2',3'-Dideoxyadenosine, 2',5'-Dideoxyadenosine, SQ22536, MDL-12330A | BRET, FRET, calcium flux assays, cAMP assays, TANGO, GeneBlazer, HitHunter, PathHunter (DiscoverX) |
| MISC ENZYMES | Acetylcholine sterase | | | Caproctamine, Metrifonate, Physostigmine, Galantamine, Dyflos, Neostigmine | Acetylcholinesterase Assay, Amplex Red, Ellman method, HPLC |
| BIOACTIVE LIPIDS | Ceramide | sphingomyelin | TNF¦¦Fas ligand, 1,25 dihydroxy vitamin D, ñinterferon | fumonisin B | TLC lipid charring, diacylglycerol kinase labeling in vitro |
| CYTOKINES | IL2 | IL2R | BAY 50-4798, P1-30, SP4206 | daclizumab, basiliximab, SP4206 | TANGO, GeneBlazer, HitHunter, PathHunter (DiscoverX), IL2 dependent mouse CTLL cell line, ELISA |
| MISC PROTEINS | BCLXL | BAD | | BH3I-1, A-371191, ABT-737 | TANGO, GeneBlazer, HitHunter, PathHunter (DiscoverX), CO-IP, BRET, FRET, ELISA |
| MISC PROTEINS | p53 | MDM2, JNK1-3, ERK1-2, p38 MAPK, ATR, ATM, Chk1, Chk2, DNA-PK, CAK | PRIMA-1, MIRA-1, RITA, | Pifithrin-α | caspase assays, apoptosis assays, mitochondrial Dy, CO-IP, BRET, FRET, TANGO, GeneBlazer, HitHunter, PathHunter (DiscoverX), ELISA |
| MISC PROTEINS | Tubulin | tubulin | | ALB109564, ABT-751, D24851, D64131, benomyl, estramustine, LY290181 | kinase assay, CO-IP, BRET, FRET, reporter assays, TANGO, GeneBlazer, δ-arrestin(DiscoverX |
| MISC PROTEINS | □-amyloid | | | L 1,10-phenanthroline derivatives, KLVFF (SEQ ID NO: 3), LVFFA (SEQ ID NO: 4), Memoquin, SLF-CR | Stagnant Amyloid Fibril Formation Assay, amyloid fibrillization assay |
| MISC PROTEINS | thymidylate synthase | | | raltitrexed, pemetrexed, nolatrexed, ZD9331, GS7904L, | caspase assays, apoptosis assays, mitochondrial Dy, CO-IP, BRET, FRET, TANGO, GeneBlazer, |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| UBIQUITIN LIGASES | MDM2 | p53 | | fluorouracil trans-4-Iodo, 4'-boranyl-chalcone, Nutlins, MI-219, MI-63, RITA, HLI98 | HitHunter, PathHunter (DiscoverX), ELISA TANGO, GeneBlazer, HitHunter, PathHunter (DiscoverX), CO-IP, BRET, FRET, ELISA, reporter assay |
| VIRAL REGULATORS | HPV E2 | HPV E1 | | indandiones, podophyllotoxin | E2 displacement assay, TANGO, GeneBlazer, HitHunter, PathHunter (DiscoverX), CO-IP, BRET, FRET, ELISA, reporter assay |
| BACTERIAL CELL DIVISION PROTEINS | ZipA | FtsZ | | substituted 3-(2-indolyl)piperidines, 2-phenyl indoles | TANGO, GeneBlazer, HitHunter, PathHunter DiscoverX), CO-IP, BRET, FRET, ELISA, reporter assay, polarization competition assay, |
| CYTOKINES | TNF | TNFR | | infliximab, adalimumab, etanercept | TANGO, GeneBlazer, HitHunter, PathHunter (DiscoverX), CO-IP, BRET, FRET, ELISA, |
| SCAFFOLD PROTEINS | JIP1 | JNK | | BI-78D3, TIJIP | TANGO, GeneBlazer, HitHunter, PathHunter (DiscoverX), CO-IP, BRET, FRET, ELISA, kinase assay |
| DNA REPAIR | PARP | | | INO-1001, AG014699, BS-201, AZD2281, BS-401 | TANGO, GeneBlazer, HitHunter, PathHunter (DiscoverX), CO-IP, BRET, FRET, ELISA, |
| RIBOSOMES | Antibiotics | ribosomes | | tetracyclins, macrolides, lincosamides, streptogramins | cell death assay, |
| HISTONE DEACETYLASES | HDAC1 | | | suberoylanilide hydroxamic acid, trichostatin A, LBH589 | TANGO, GeneBlazer, HitHunter, PathHunter (DiscoverX), CO-IP, BRET, FRET, ELISA, |
| APOPTOSIS REGULATORS | XIAP | SMAC/DIABLO, caspase 3, caspase 7, caspase 9 | | SM102-SM130 | CO-IP, BRET, FRET, reporter assays, TANGO, GeneBlazer, HitHunter, PathHunter (DiscoverX), cell death assays |
| CHAPERONE PROTEINS | Hsp90 | Cdc37, survivin | | Celastrol, shepherdin | CO-IP, BRET, FRET, reporter assays, TANGO, GeneBlazer, HitHunter, PathHunter (DiscoverX), |
| SERINE/THREONINE PROTEIN KINASES | mTOR | Raptor, mLST8/GβL | | Rapamycin, caffeine, farnesylthiosalicylic acid, curcumin, temsirolimus, everolimus | kinase assay, CO-IP, BRET, FRET, reporter assays, TANGO, GeneBlazer, HitHunter, PathHunter (DiscoverX) |
| SERINE/THREONINE-PROTEIN KINASES | B-raf & B-raf V600E | K-ras | | PLX4720 | kinase assay, CO-IP, BRET, FRET, reporter assays, TANGO, GeneBlazer, HitHunter, PathHunter (DiscoverX), |
| CYCLIN DEPENDENT KINASES | CDK2 | Cyclin A, cyclin E | | Variolin, Meriolin | kinase assay, CO-IP, BRET, FRET, reporter assays, TANGO, GeneBlazer, HitHunter, PathHunter (DiscoverX), |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| GROWTH FACTOR RECEPTORS | IGF-1R | IGFII | | PQIP | CO-IP, BRET, FRET, reporter assays, TANGO, GeneBlazer, HitHunter, PathHunter (DiscoverX), |
| PROTEASOME | 20S | 19S | | Bortezomib, salinosporamide A, | CO-IP, BRET, FRET, cell viability |

TABLE 2

Examples of Protein Domains

| DOMAIN | PARTNER | EXAMPLE OF PROTEIN CONTAINING DOMAIN | EXAMPLES OF KNOWN INHIBITORS | EXAMPLES OF DETECTION ASSAYS | APPROXIMATE $K_D$ OF BINDING PARTNERS |
|---|---|---|---|---|---|
| SH2 | Phospho-tyrosine residues | Grb2 | Fmoc-Glu-Tyr-Aib-Asn-NH2 (SEQ ID NO: 5): Ac-SpYVNVQ-NH2 (SEQ ID NO: 6), macrocycles, STATTIC | Surface plasmon resonance (SPR) technology, | 0.2-11 μM |
| FHA | Phospho-threonine and phospho-tyrosine residues | KIF13B | | | 1-100 μM |
| 14-3-3 | Phospho-serine residues | 14-3-3 | R18 | | 7 nM-20 μM |
| WW | ligands containing PpxY, Proline-rich sequences | Pin1 | Zn(II) Dipicolylamine-based artificial receptors | | 6 μM-190 μM |
| WD40 | | Apaf-1 | | | 1 μM |
| MH2 | phospho-serine residues | SMAD2 | | | 240 nM |
| BROMO | acetylated lysine residues | CBP | | | 1 μM-4 mM |
| UBA | mono-, di-, tri-, and tetra-ubiquitin | IIIIR23A | | | 6 μM-2.35 mM |
| PTB | Phospho-tyrosine residues, Asn-Pro-X-Tyr motifs | IRS-1 | LSNPTX-NH2 (SEQ ID NO: 7), LYASSNPAX-NH2 (SEQ ID NO: 8) | PTB domain binding assays | 160 nM-10 μM |
| SH3 | Proline-rich peptides with consensus Pro-X-X-Pro, | Grb2 | Peptidimer-c, VPPPVPPRRR (SEQ ID NO: 9), (VPPPVPPRRR) (SEQ ID NO: 9))2K) | | 1-500 μM |
| EVH1 | FPxΦP motifs, PPxxF motifs | ActA | | | 10-50 μM |
| GYF | proline-rich sequences, | CDBP2 | | | 10-160 μM |
| VHS | | TOM1 | | | 11-50 μM |
| PDZ | PDZ, Val-COOH | MNT1 | | | 1-500 μM |
| PUF | RNA | PUM1 | NSC668036, FJ9 | | 10-100 nM |
| TUBBY | DNA, phosphotidylinositol | TULP1 | | | |
| SAM | | CNK | | | 71 nM-1 μM |
| DD | DD | FADD | | | |
| CARD | CARD | Apaf-1 | | | 1.4 μM |
| PyD | PyD | Pyrin | | | 4 μM |
| PB1 | PB1 | Bem1 | | | 4-500 nM |
| BRCT | BRCT | BRCA1 | | | 113 nM-6 μM |
| PH | phosphatidylinositol-4,5-bisphosphate, PI-3, 4-P2 or PI-3,4,5-P3 | AKT1 | NSC 348900, perifosine, SH5, SH23, SH24, SH25, ml14, ml15, ml16 | | 1.76 nM-350 μM |

TABLE 2-continued

Examples of Protein Domains

| DOMAIN | PARTNER | EXAMPLE OF PROTEIN CONTAINING DOMAIN | EXAMPLES OF KNOWN INHIBITORS | EXAMPLES OF DETECTION ASSAYS | APPROXIMATE $K_D$ OF BINDING PARTNERS |
|---|---|---|---|---|---|
| FYVE | Phosphatidylinositol 3-phosphate, zinc | SARA | | | 50 nM-140 µM |
| C1 | phorbol esters, diacylglycerol | PKC isoforms | | | 0.58-800 nM |
| FERM | PI(3)P, PI(4)P, PI(5)P, IP3, | PTLP1 | | | 200 nM-30 µM |
| C2 | Calcium, acidic phospholipids | Nedd4 | | | 250 nM-94 µM |
| PX | PI(3,4)P2, PI(3)P, PI(3,5)P2, PI(4)P, PI(5)P, PI(3,4,5)P3, PI(4,5)P2 | CISK | | | 1.8 nM-50 µM |
| ENTH | PtdIns(4,5)P2, PtdIns(1,4,5)P3, PI(3,4)P2; PI(3,5)P2 | Epsin1 | | | 98 nM-1 µM |

A pharmacophore is typically an arrangement of the substituents of a moiety that confers biochemical or pharmacological effects. In some embodiments, identification of a pharmacophore may be facilitated by knowing the structure of the ligand in association with a target biomolecule. In some cases, pharmacophores may be moieties derived from molecules previously known to bind to target biomolecules (e.g., proteins), fragments identified, for example, through NMR or crystallographic screening efforts, molecules that have been discovered to bind to target proteins after performing high-throughput screening of natural products libraries, previously synthesized commercial or non-commercial combinatorial compound libraries, or molecules that are discovered to bind to target proteins by screening of newly synthesized combinatorial libraries. Since most preexisting combinatorial libraries are limited in the structural space and diversity that they encompass, newly synthesized combinatorial libraries may include molecules that are based on a variety of scaffolds.

Additionally pharmacophores may be derived from traditional approaches such as fragment based drug design and structure based drug design. Those skilled in the art will recognize that any pharmacophore including pre-existing pharmacophores such as approved drugs are amenable to be designed as monomers through the incorporation of the appropriate linker elements and connector elements. For example, previously approved drugs that have poor efficacy due to a low affinity for a first macromolecular target may be utilized as a pharmacophore component of a first monomer which when combined with a pharmacophore of a second monomer that also binds the first macromolecular target or a second macromolecular target that interacts with the first macromolecular target results in enhanced binding and, in some cases, higher efficacy. Likewise, previously approved drugs that have low efficacy as a result of size, molecular weight or other physicochemical attributes that reduce the cellular uptake of the drug may be amenable to being converted into one or more monomers that bear the appropriate pharmacophoric elements, such that each monomer has physicochemical attributes that allow for increased cellular uptake.

In some embodiments, a ligand moiety (e.g., a pharmacophore) may have a molecular weight between 50 Da and 2000 Da, in some embodiments between 50 Da and 1500 Da, in some embodiments, between 50 Da and 1000 Da, and in some embodiments, between 50 Da and 500 Da. In certain embodiments, a ligand moiety may have a molecular weight of less than 2000 Da, in some embodiments, less than 1000 Da, and in some embodiments less than 500 Da.

In certain embodiments, the compound utilized by one or more of the foregoing methods is one of the generic, subgeneric, or specific compounds described herein.

Disclosed compositions may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound may be administered orally, subcutaneously, topically, parenterally, by inhalation spray or rectally in dosage unit formulations containing conventional non-toxic pharmaceutically acceptable carriers, adjuvants, and vehicles. Parenteral administration may include subcutaneous injections, intravenous or intramuscular injections, or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a partial or total alleviation of symptoms, is achieved.

In another aspect, pharmaceutical compositions comprising monomers, dimers, and/or multimers as disclosed herein formulated together with a pharmaceutically acceptable carrier provided. In particular, the present disclosure provides pharmaceutical compositions comprising monomers, dimers, and/or multimers as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid, or liquid form, which contains one or more of the compounds, as an active ingredient, in admixture with an organic or inorganic carrier or excipient suitable for external, enteral, or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include nonionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, enteral pharmaceutical formulations including a disclosed pharmaceutical composition comprising monomers, dimers, and/or multimers, an enteric material; and a pharmaceutically acceptable carrier or excipient thereof are provided. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleat, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that may be used.

Advantageously, kits are provided containing one or more compositions each including the same or different monomers. Such kits include a suitable dosage form such as those described above and instructions describing the method of using such dosage form to treat a disease or condition. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include additional active agents, or administering additional active agents.

Also contemplated herein are methods and compositions that include additional active agents, or administering additional active agents.

Certain terms employed in the specification, examples, and appended claims are collected here. These definitions should be read in light of the entirety of the disclosure and understood as by a person of skill in the art. Unless defined otherwise, all technical and scientific terms used herein have the same meaning as commonly understood by a person of ordinary skill in the art.

Definitions

In some embodiments, the compounds, as described herein, may be substituted with any number of substituents or functional moieties. In general, the term "substituted" whether preceded by the term "optionally" or not, and substituents contained in formulas, refer to the replacement of hydrogen radicals in a given structure with the radical of a specified substituent.

In some instances, when more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. In some embodiments, heteroatoms such as nitrogen may have hydrogen substituents and/or any permissible substituents of organic compounds described herein which satisfy the valencies of the heteroatoms. Non-limiting examples of substituents include acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —SCN; —SR$_x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$_x$, —C(O)R$_x$; —CO$_2$(R$_x$); —C(O)N(R$_x$)$_2$; —OC(O)R$_x$; —OCO$_2$R$_x$; —OC(O)N(R$_x$)$_2$; —N(R$_x$)$_2$; —SOR$_x$; —S(O)$_2$R$_x$; —NR$_x$C(O)R$_x$; or —C(R$_x$)$_3$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Furthermore, the compounds described herein are not intended to be limited in any manner by the permissible substituents of organic compounds. In some embodiments, combinations of substituents and variables described herein may be preferably those that result in the formation of stable compounds. The term "stable," as used herein, refers to compounds which possess stability sufficient to allow manufacture and which maintain the integrity of the compound for a sufficient period of time to be detected and preferably for a sufficient period of time to be useful for the purposes detailed herein.

The term "acyl," as used herein, refers to a moiety that includes a carbonyl group. In some embodiments, an acyl group may have a general formula selected from —C(O)R$_x$; —CO$_2$(R$_x$); —C(O)N(R$_x$)$_2$; —OC(O)R$_x$; —OCO$_2$R$_x$; and —OC(O)N(R$_x$)$_2$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —SCN; —SR$_x$; —CF$_3$; —CH$_2$CF$_3$; —CHCl$_{1-2}$; —CH$_2$OH; —CH$_2$CH$_2$OH; —CH$_2$NH$_2$; —CH$_2$SO$_2$CH$_3$; —OR$_x$, —C(O)R$_x$; —CO$_2$(R$_x$); —C(O)N(R$_x$)$_2$; —OC(O)R$_x$; —OCO$_2$R$_x$; —OC(O)N(R$_x$)$_2$; —N(R$_x$)$_2$; —SOR$_x$; —S(O)$_2$R$_x$; —NR$_x$C(O)R$_x$; or —C(R$_x$)$_3$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

In general, the terms "aryl" and "heteroaryl," as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments, aryl refers to a mono- or bicyclic carbocyclic ring system having one or two aromatic rings including, but not limited to, phenyl, naphthyl, tetrahydronaphthyl, indanyl, indenyl, and the like. In certain embodiments, the term heteroaryl, as used herein, refers to a cyclic aromatic radical having from five to ten ring atoms of which one ring atom is selected from the group consisting of S, O, and N; zero, one, or two ring atoms are additional heteroatoms independently selected from the group consisting of S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$ R$_x$; —NR$_x$(CO)R$_x$, wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heterocyclic," as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from the group consisting of oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from the group consisting of O, S, and N (wherein the nitrogen and sulfur heteroatoms may be optionally oxidized), including, but not limited to, a bi- or tri-cyclic group, comprising fused six-membered rings having between one and three heteroatoms independently selected from the group consisting of the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_{2-6}$alkenyl, and $C_{3-4}$alkenyl, respectively. Exemplary alkenyl groups include, but are not limited to, vinyl, allyl, butenyl, pentenyl, etc.

The term "alkenyloxy" used herein refers to a straight or branched alkenyl group attached to an oxygen (alkenyl-O). Exemplary alkenoxy groups include, but are not limited to, groups with an alkenyl group of 3-6 carbon atoms referred to herein as $C_{3-6}$alkenyloxy. Exemplary "alkenyloxy" groups include, but are not limited to allyloxy, butenyloxy, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as $C_{1-6}$alkoxy, and $C_2$-$C_6$alkoxy, respectively. Exemplary alkoxy groups include, but are not limited to methoxy, ethoxy, isopropoxy, etc.

The term "alkoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, for example, such as a straight or branched group of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "carboxylic acid" as used herein refers to a group of formula —CO$_2$H.

The term "cyano" as used herein refers to the radical —CN.

The term "cycloalkoxy" as used herein refers to a cycloalkyl group attached to an oxygen (cycloalkyl-O—).

The term "cycloalkyl" as used herein refers to a mono-cyclic saturated or partially unsaturated hydrocarbon group of for example 3-6, or 4-6 carbons, referred to herein, e.g., as $C_{3-6}$cycloalkyl or $C_{4-6}$cycloalkyl and derived from a cycloalkane. Exemplary cycloalkyl groups include, but are not limited to, cyclohexyl, cyclohexenyl, cyclopentyl, cyclobutyl or, cyclopropyl.

The terms "halo" or "halogen" as used herein refer to F, Cl, Br, or I.

The term "heterocyclylalkoxy" as used herein refers to a heterocyclyl-alkyl-O— group.

The term "heterocyclyloxyalkyl" refers to a heterocyclyl-O-alkyl- group.

The term "heterocyclyloxy" refers to a heterocyclyl-O— group.

The term "heteroaryloxy" refers to a heteroaryl-O— group.

The terms "hydroxy" and "hydroxyl" as used herein refers to the radical —OH.

The term "oxo" as used herein refers to the radical =O.

The term "connector" as used herein to refers to an atom or a collection of atoms optionally used to link interconnecting moieties, such as a disclosed linker and a pharmacophore. Contemplated connectors are generally hydrolytically stable.

"Treating" includes any effect, e.g., lessening, reducing, modulating, or eliminating, that results in the improvement of the condition, disease, disorder and the like.

"Pharmaceutically or pharmacologically acceptable" include molecular entities and compositions that do not produce an adverse, allergic, or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated is desirably a mammal in which treatment of obesity, or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal, or human that is being sought by the researcher, veterinarian, medical doctor, or other clinician. The compounds are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. Various stereoisomers of these compounds and mixtures thereof are encompassed by this disclosure. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomers and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds. The symbol $=\!=\!=$ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. Various stereoisomers of these compounds and mixtures thereof are encompassed by this disclosure.

Individual enantiomers and diasteriomers of the compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like. In one embodiment, the compound is amorphous. In one embodiment, the compound is a polymorph. In another embodiment, the compound is in a crystalline form.

Also embraced are isotopically labeled compounds which are identical to those recited herein, except that one or more atoms are replaced by an atom having an atomic mass or mass number different from the atomic mass or mass number usually found in nature. Examples of isotopes that can be incorporated into the compounds include isotopes of hydrogen, carbon, nitrogen, oxygen, phosphorus, sulfur, fluorine and chlorine, such as $^{2}H$, $^{3}H$, $^{13}C$ $^{14}C$, $^{15}N$, $^{18}O$, $^{17}O$, $^{31}P$, $^{32}P$, $^{35}S$, $^{18}F$, $^{10}B$, and $^{36}Cl$, respectively. For example, a compound may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds can generally be prepared by following procedures analogous to those disclosed in the Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood, or liver). Prodrugs are well known in the art (for example, see Rautio, Kumpulainen, et al, Nature Reviews Drug Discovery 2008, 7, 255). For example, if a compound or a pharmaceutically acceptable salt, hydrate, or solvate of the compound contains a carboxylic acid functional group, a prodrug can comprise an ester formed by the replacement of the hydrogen atom of the acid group with a group such as $(C_{1-8})$alkyl, $(C_{2-12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_{1}$-$C_{2})$alkylamino$(C_{2}$-$C_{3})$alkyl (such as β-dimethylaminoethyl), carbamoyl-$(C_{1}$-$C_{2})$alkyl, N,N-di$(C_{1}$-$C_{2})$alkylcarbamoyl-$(C_{1}$-$C_{2})$alkyl and piperidino-, pyrrolidino- or morpholino$(C_{2}$-$C_{3})$alkyl.

Similarly, if a compound contains an alcohol functional group, a prodrug can be formed by the replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl $(C_{1-6})$alkoxycarbonyloxymethyl, N—$(C_{1-6})$alkoxycarbonylaminomethyl, succinoyl, $(C_{1-6})$alkanoyl, α-amino$(C_{1-4})$alkanoyl, arylacyl and α-aminoacyl, or α-aminoacyl-α-aminoacyl, where each α-aminoacyl group is independently selected from the naturally occurring L-amino acids, P(O)(OH)$_{2}$, —P(O)(O$(C_{1}$-$C_{6})$alkyl)$_{2}$ or glycosyl (the radical resulting from the removal of a hydroxyl group of the hemiacetal form of a carbohydrate).

If a compound incorporates an amine functional group, a prodrug can be formed, for example, by creation of an amide or carbamate, an N-acyloxyakyl derivative, an (oxodioxolenyl)methyl derivative, an N-Mannich base, imine, or enamine. In addition, a secondary amine can be metabolically cleaved to generate a bioactive primary amine, or a tertiary amine can be metabolically cleaved to generate a bioactive primary or secondary amine. For examples, see Simplicio, et al., *Molecules* 2008, 13, 519 and references therein.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as active ingredients.

For ease of reading, intermediates are provided in Table 3. At least some of the compounds identified as "Intermediates" herein are contemplated as compounds of the invention. Example compounds are provided in Table 4.

TABLE 3

INTERMEDIATES INDEX

| Sr. No. | Structure | Compound Name | Cmpd. Code |
|---|---|---|---|
| Tryptase targets Method-D | | | |
| 1. | 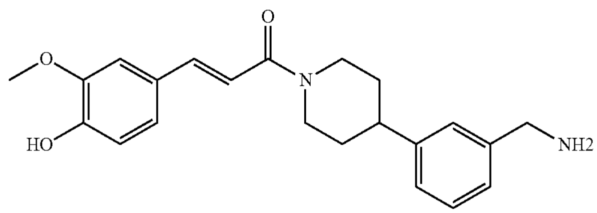 [SMILES: COc1cc(/C=C/C(=O)N2CCC(c3cccc(CN)c3)CC2)ccc1O] | (E)-1-(4-(3-(aminomethyl)phenyl)piperidin-1-yl)-3-(4-hydroxy-3-methoxyphenyl)prop-2-en-1-one | T-24 mono methoxy |
| 2. | 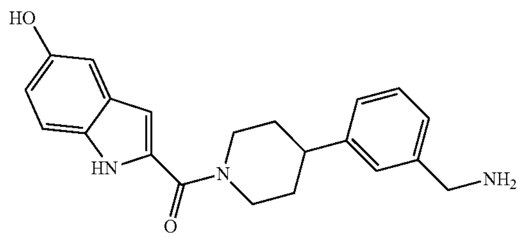 [SMILES: NCc1cccc(C2CCN(C(=O)c3cc4cc(O)ccc4[nH]3)CC2)c1] | (4-(3-(aminomethyl)phenyl)piperidin-1-yl)(5-hydroxy-1H-indol-2-yl)methanone | Target-31a |
| 3. | 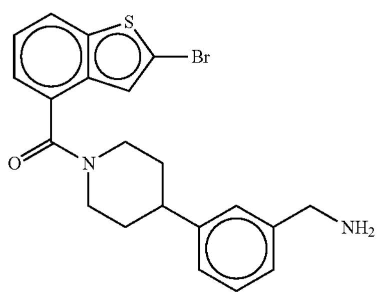 | (4-(3-(aminomethyl)phenyl)piperidin-1-yl)(2-bromobenzo[b]thiophen-4-yl)methanone | Target-37a |
| 4. | 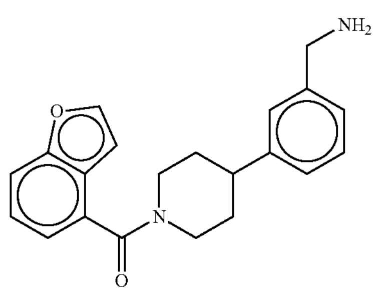 | (4-(3-(aminomethyl)phenyl)piperidin-1-yl)(benzofuran-4-yl)methanone | Target-38H |
| 5. | 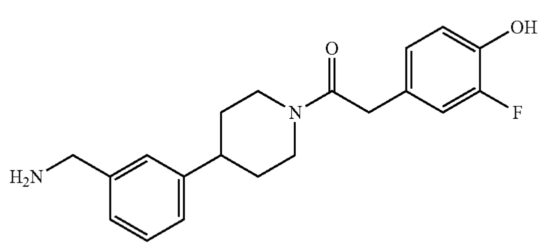 [SMILES: NCc1cccc(C2CCN(C(=O)Cc3ccc(O)c(F)c3)CC2)c1] | 1-(4-(3-(aminomethyl)phenyl)piperidin-1-yl)-2-(3-fluoro-4-hydroxyphenyl)ethanone | Target-54a |
| 6. | 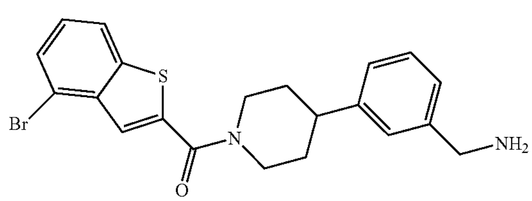 [SMILES: NCc1cccc(C2CCN(C(=O)c3cc4c(Br)cccc4s3)CC2)c1] | (4-(3-(aminomethyl)phenyl)piperidin-1-yl)(4-bromobenzo[b]thiophen-2-yl)methanone | Target-56a |

TABLE 4

EXAMPLES OF HOMODIMERS

| Sr. No. | Cmpd. Code | Structure |
|---|---|---|
| 7. | Formed form Target-46 | 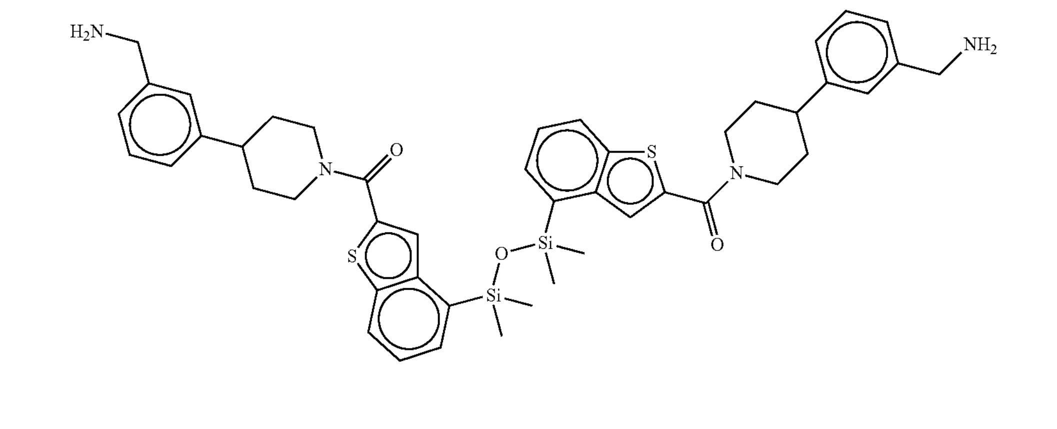 |
| 8. | Formed form Target-47 | 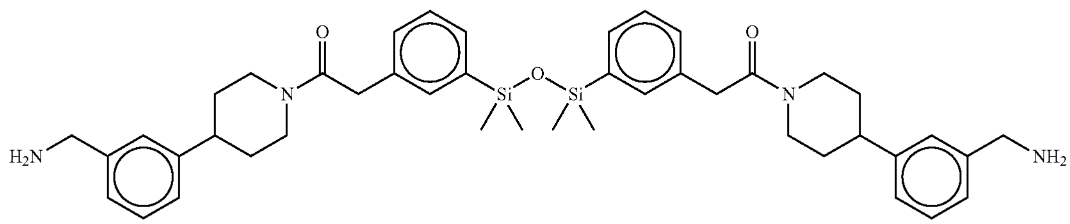 |
| 9. | Formed form Target-48 | 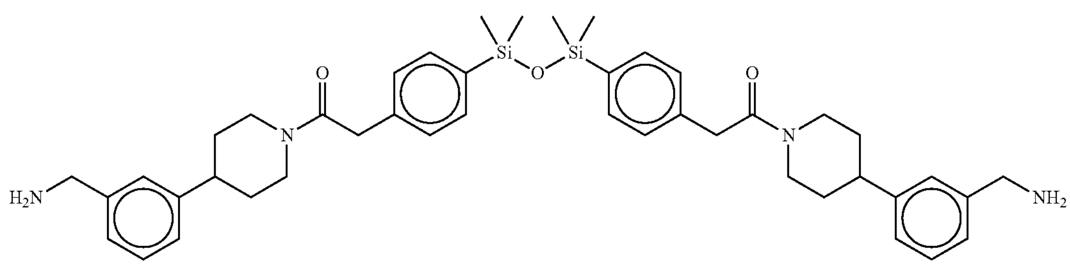 |
| 10. | Formed form Target-47-Vinyl | 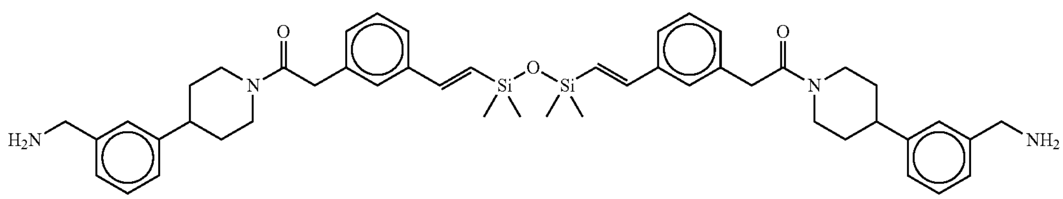 |

Example 1

Evaluation of Inhibition of Tryptase Activity by Multimers

Stock solutions of recombinant human tryptase, beta, from lung (Promega: catalog number G5631, or Enzo Life Sciences: catalog number BML-SE418) were made at 30 μM, in solution with 50 μM heparin sulfate and 500 mM NaCl. Multimer tryptase inhibitor stock solutions were made at 50 mM in DMSO. Drug plates were made at 5× the final concentration in assay buffer (50 mM HEPES, 150 mM NaCl, 100 μM EDTA, pH 7.4, 0.02% Tween-20). A final concentration of 1 nM tryptase was used. When required, drugs were diluted in assay buffer immediately before use in 10-fold serial dilutions. After the indicated incubation time, the multimer-tryptase solution at 5× concentration, was diluted into assay buffer containing a final concentration of 200 μM N-tert-butoxycarbonyl-Gln-Ala-Arg-AMC HBr [AMC=7-amino-4-methylcoumarin] (Boc-Gln-Ala-Arg-AMC; Enzo Life Sciences: catalog number BML-P237) to a final volume of 50 μl in black opaque round bottom 96 well plates (Corning, catalog number 3792). The release of fluorescent AMC was immediately measured every 60 seconds over 30-60 minutes at an excitation wavelength of 367 nm, monitoring emission at 468 nm on a Spectramax M5 (Molecular Devices) microplate reader. The Softmax Pro (Molecular Devices) and Graphpad prism software were used to determine $V_{max}$, and concentration-response curve $IC_{50}$s, respectively.

Example 2

Evaluation of Inhibition of Ribosomal Protein Synthesis by Multimers

Monomers with the potential to form heterodimers were evaluated in an in vitro Transcription and Translation assay (TnT assay) using the commercially available *E. coli* S30 Extract System for Circular DNA kit (Promega Catalog #L1020) according to the manufacturers instructions with minor modifications. Monomers were tested independently to determine individual $IC_{50}$ values. Pairs of monomers with the potential to form heterodimers were assayed at concentrations that ranged about their individual $IC_{25}$ values. Each reaction uses 2 μl (250 ng/μl) of the pBESTluc™ DNA based circular luciferase plasmid (Promega Catalog #L492A), with 4 μl of complete amino acid mix (Promega Catalog #L4461), 13 of S30 Premix Without Amino Acids (Promega Catalog #L512A), 5 μl of S30 Extract (Promega Catalog #L464A), monomers at the appropriate concentration, and nuclease free water in a total volume of 35 al. Assays were carried out in Costar 96 well white round bottom plates. Assay plates were setup with a master mix consisting of S30 extract and water, followed by the addition of compound, with the final addition of a master mix consisting of the plasmid, amino acid mix, and the S30 Premix. Plates were incubated at 37° C. for one hour followed by addition of 35 μl of the Bright-Glo Luciferase Reagent (Promega Catalog #E2620). After removal of 35 μl of the reaction mixture, the luminescence was recorded immediately in the Spectramax M5 plate reader (Molecular Devices). The data was plotted to generate dose-response curves using GraphPad Prism.

As indicated below, $IC_{50}$ ranges are provided for various exemplary monomers. For the names of the monomers, the prefix "Target," as used elsewhere in the Examples, has been shortened to "T." For example, "Target-14" has been shortened to "T14." "A" refers to an $IC_{50}$ range of 0.1 nM to 1 μM, "B" refers to an $IC_{50}$ range of 1 μM to 10 μM, and "C" refers to an $IC_{50}$ range of 10 μM to 65 μM.

Results

Group A: T52; T148; T120F; T52SPIRO; T129SPIRO; T46; T129; T138; T129Smethyl;
T130; T49; T137; T47; T11SILYL.
Group B: T149; T47vinyl; T122; T48.
Group C: T152NMethyl; T35 Silyl; T32Silyl; T152; T61Silyl.

Example 3

Synthesis of Dimethyl (Aryl) Silanols

Method G

Desired halo aryl carboxylic acids were first coupled with tert-butyl 3-(piperidin-4-yl) benzylcarbamate and coupled product was reacted with 1,2-diethoxy-1,1,2,2-tetramethyl-disilane to get ethoxydimethyl(Aryl)silanes, which upon treatment with acetic adid and subsequent treatment with TFA resulted in the title compounds. These compounds as well as their N-Boc precursors were found to be in the form of mixture of monomer and dimer in HPLC/LCMS analysis.

Vinylic analogue of this compound was synthesized by reaction of Boc De-protected B-47 with dimethyl ethoxy vinyl silane in presence of Pd (II) acetate & Tri (O-tolyl) phosphine in DMF using sodium acetate as a base (Scheme-2).

SCHEME 1. Method G

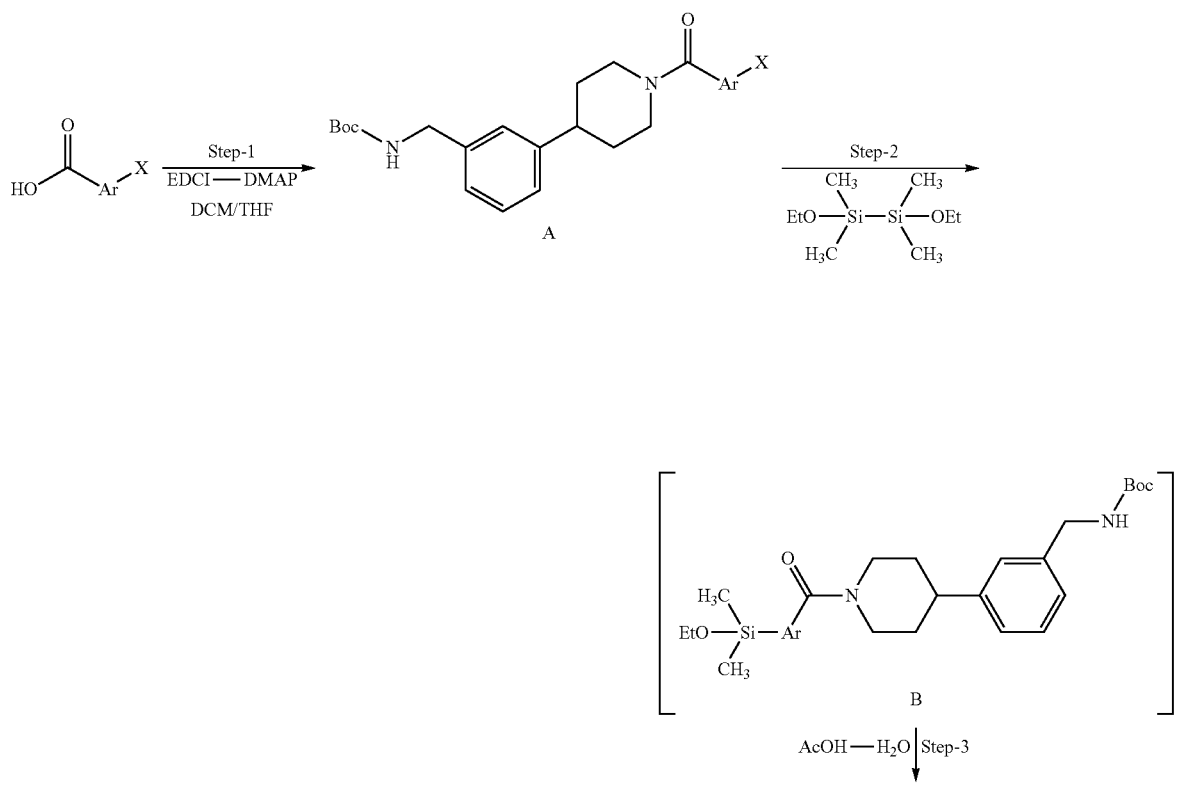

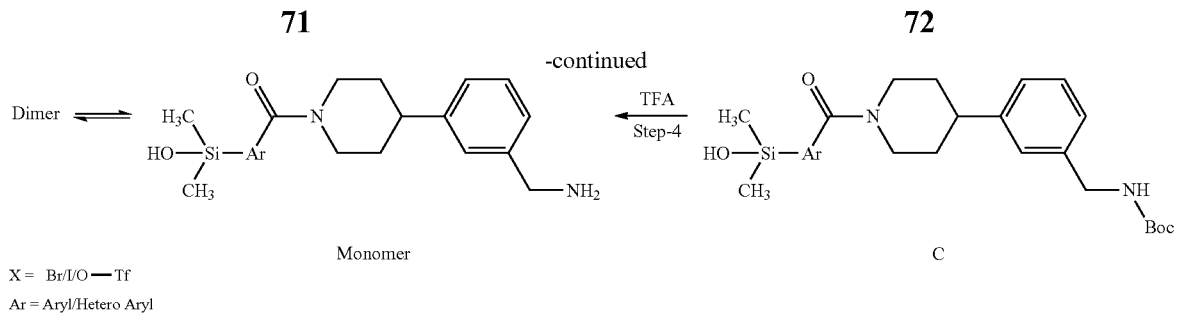

X = Br/I/O—Tf
Ar = Aryl/Hetero Aryl

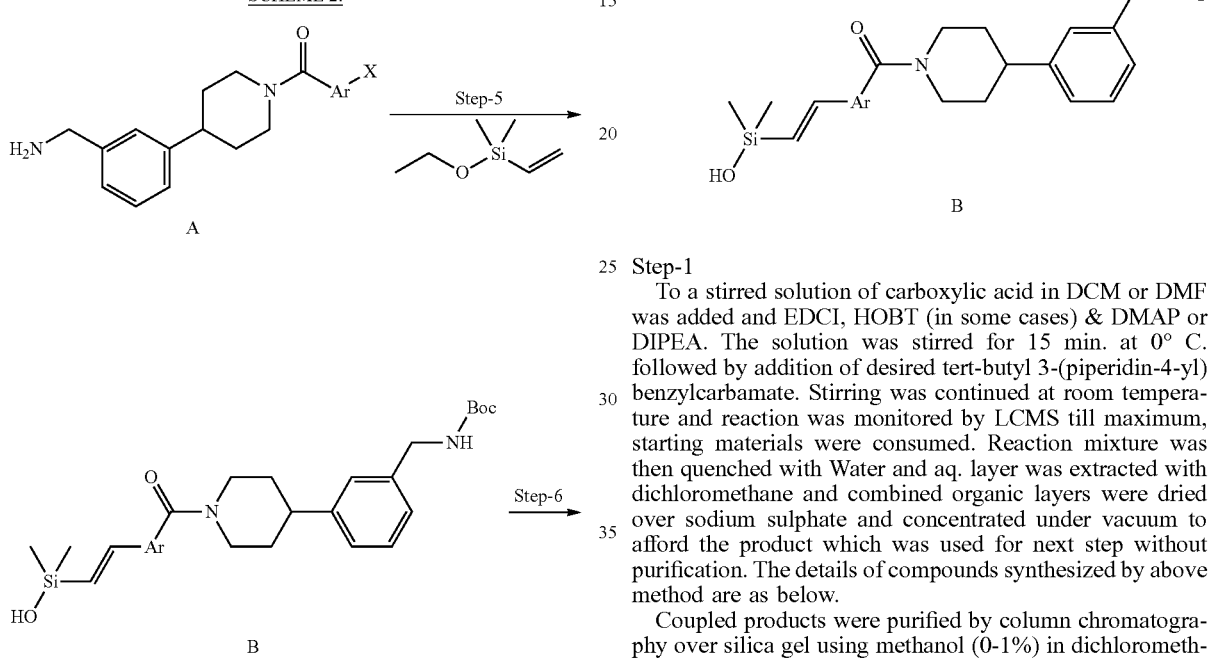

Step-1

To a stirred solution of carboxylic acid in DCM or DMF was added and EDCI, HOBT (in some cases) & DMAP or DIPEA. The solution was stirred for 15 min. at 0° C. followed by addition of desired tert-butyl 3-(piperidin-4-yl) benzylcarbamate. Stirring was continued at room temperature and reaction was monitored by LCMS till maximum, starting materials were consumed. Reaction mixture was then quenched with Water and aq. layer was extracted with dichloromethane and combined organic layers were dried over sodium sulphate and concentrated under vacuum to afford the product which was used for next step without purification. The details of compounds synthesized by above method are as below.

Coupled products were purified by column chromatography over silica gel using methanol (0-1%) in dichloromethane. Details of the compounds synthesized are as below.

TABLE 6

REACTION CONDITIONS & ANALYTICAL DATA

| Comp. No. | Structure | Brief Reaction conditions | Analytical data |
|---|---|---|---|
| B-46 | 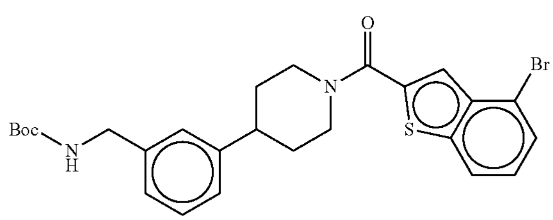 | tert-butyl 3-(piperidin-4-yl) benzyl carbamate (1 eq.), EDCI (1.5 eq.), DMAP(1.1 eq) HOBT (1.1 eq)DCM, RT, 2 h, Yield:- 51.53% | Mol. Wt:- 529.49 M.I. Peak observed:- 531.30 HPLC purity:- 92.16% |
| B-47 | 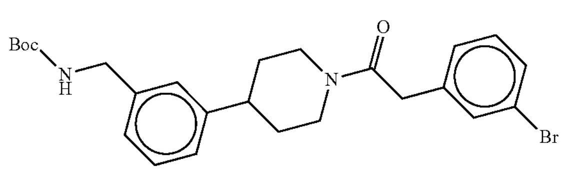 | Same as above Yield:- 60.78% | Mol. Wt:- 487.43 M.I. Peak observed:- 509.35 (M + Na), HPLC purity:- 91.37% |

TABLE 6-continued

REACTION CONDITIONS & ANALYTICAL DATA

| Comp. No. | Structure | Brief Reaction conditions | Analytical data |
|---|---|---|---|
| B-48 | 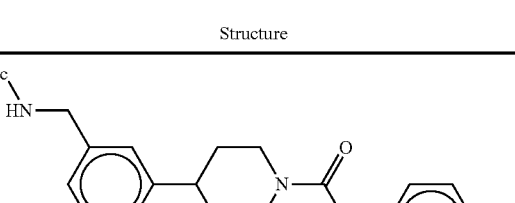 | Same as above Yield:- 88.20% | Mol. Wt:- 487.43 M.I. Peak observed:- 489.25 HPLC purity:- 97.88% |
| B-49 | 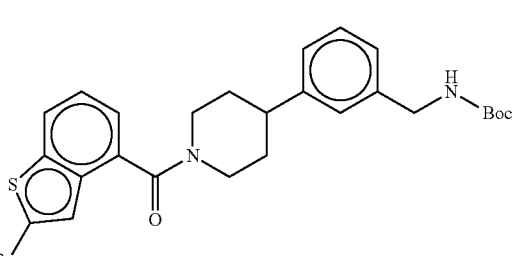 | Same as above Yield:-% 50% | Mol. Wt:- 529.49 M.I. Peak observed:- 553.05(M + Na) |

Step-2 & 3

Stirred suspension of Coupled products from step-1 was degassed with argon and N-methyl pyrrolidine, palladium chloride, di-isopropylethylamine & 1,2,diethoxy-1,1,2,2, tetramethyl silane was added to it. Reaction mass was heated to ~60° C. and reaction monitored by LCMS till maximum starting material was consumed. There after acetonitrile, 1N aq. acetic acid and 2-(dimethyl-amino)-ethane thiol hydrochloride was added and reaction mass stirred for 2 hrs at room temperature. Reaction mass was then diluted with water, extracted with ethyl acetate and ethyl acetate extracts were concentrated in vacuum after drying over sodium sulfate to get the crude products which were partly purified by column chromatography (Purity ~50% by HPLC) and used for next step.

TABLE 7

REACTION CONDITIONS & ANALYTICAL DATA

| Comp. No. | Structure | Brief Reaction conditions | Analytical data |
|---|---|---|---|
| C-46 | 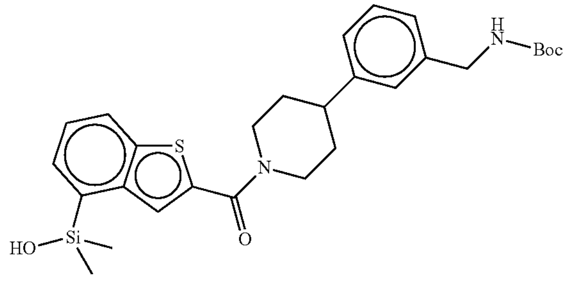 | Step-2 NMP (10 vol), PdCl2(0.1 eq), DTBP BP(0.2 eq), DIPEA(6 eq), 1,2,diethoxy-1,1,2,2, tetramethyl silane (3 eq), 60° C. 18 hrs, Step-3 Acetonitrile (10 vol) 1N aq. acetic acid (20 Vol), 2-(Dimethyl amino) ethane thiol hydrochloride (0.25 eq.) RT, 2 hrs, Yield:- 33% (Crude) | Mol. Wt:- 1031.48 (Dimer) 524.22(monomer) M.I. Peak observed- De-Boc Dimer -831.10 |
| C-47 | 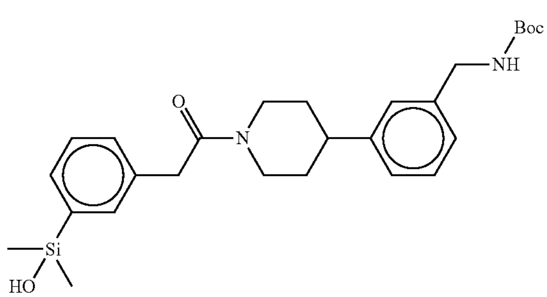 | Same as above Yield:- 41% | Mol. Wt:- 947.36 (Dimer) 482.36 (monomer) M.I. Peak observed- Monomer:- 483.45 De-Boc Dimer:- 747.40 |

TABLE 7-continued

REACTION CONDITIONS & ANALYTICAL DATA

| Comp. No. | Structure | Brief Reaction conditions | Analytical data |
|---|---|---|---|
| C-48 | 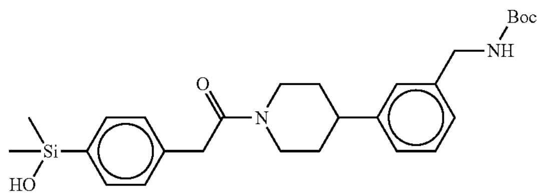 | Same as above Yield:- 30% | Mol. Wt:- 947.36(Dimer) 482.36 (monomer) M.I. Peak observed- De-Boc Dimer-747.25 |
| C-49 | 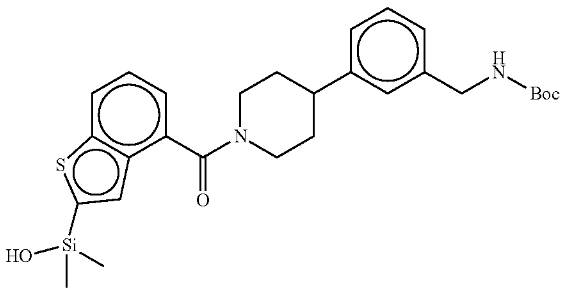 | Same as above Yield:- 30% | Mol. Wt:- 1031.48(Dimer) 524.75 (monomer) M.I. Peak observed- De-Boc monomer 425.1 De-Boc Dimer-831.3 |

Step-4

Products from step-3 were stirred with trifluoroacetic acid in dichoromethane at room temperature and reactions were monitored by TLC & LCMS till maximum, starting materials were consumed. Reaction mass was concentrated in vacuum to remove excess trifluoro acetic acid and dichlorimethane. Crude products obtained were purified by reverse phase preparative HPLC. The pure fraction of mobile phase was lyophilized to get the products as TFA salts.

TFA salts were converted to hydrochloride salts by stirring with 2N HCl for 30 min under nitrogen atmosphere followed by lyophilization.

Compounds were found to be mixture of monomer & dimer as per HPLC as well as NMR data, in all the cases.

TABLE 8

REACTION CONDITIONS & ANALYTICAL DATA

| Comp. No. | Structure | Brief Reaction conditions | Analytical data |
|---|---|---|---|
| Target-46 | 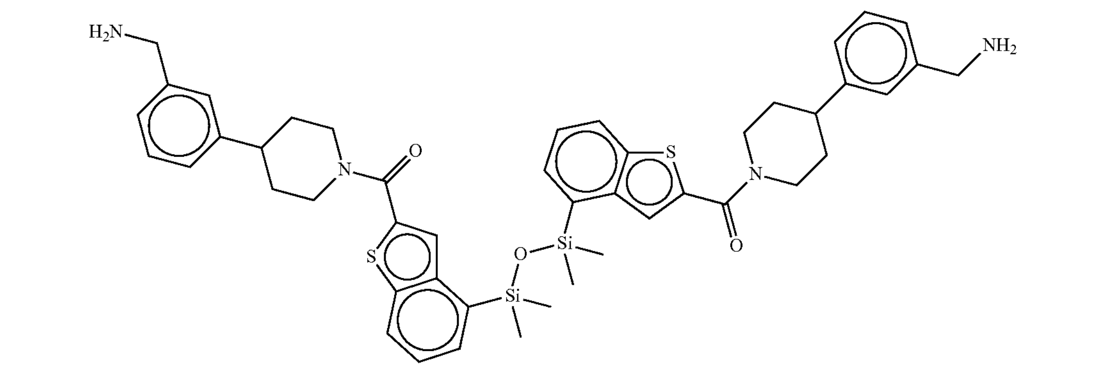 | DCM, TFA(3.3 Vol), RT, 3 Hrs. Preparative HPLC. Isolated as TFA salt. Yield:- 12% | Mol. Wt:- 831.25Dimer 424.63-Monomer M.I. Peak observed (LSMS):- 446.90(Monomer + Na) 831.20(Dimer) HPLC Purity:- 36.15% monomer, 63.84% dimer ¹H NMR CD3OD:- 3.4(d, 6H), 1.60-1.96 (m, 4H), 2.80-2.99(m, 4H), 4.09-4.11 (d, 2H), 4.59(s, 1H), 7.25-7.45 (m, 4H), 7.59-7.69(m, 2H), 7.96-7.99(m, 2H). |
| Target-47 | 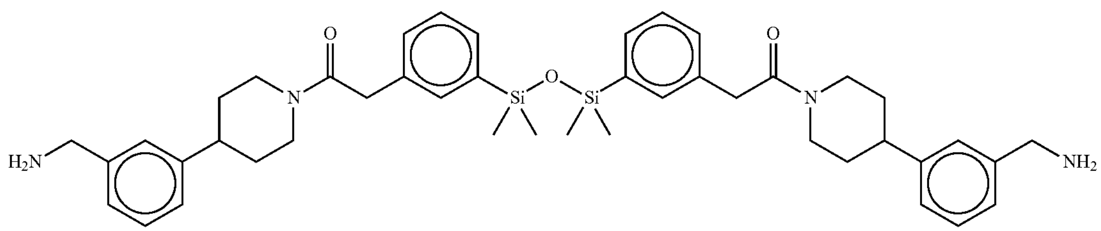 | Same as above. Preparative HPLC. Isolated as TFA salt. Yield:- 10% | Mol. Wt:- 382.57 (monomer) Dimer-747.13 M.I. Peak observed: 383.45 HPLC Purity:- 91.53 monomer, 6.4% dimer ¹H NMR ACN-d3:D2O:- 0.27(s, 12H), 1.18-1.30(m, 2H), 1.43-1.50(m, 2H), 1.67-1.70(d, 2H), 1.78-1.81(d, 2H), 1.92-1.96 (m, 2H), 3.71(s, 2H), 3.81-3.83 (m, 2H), 3.94-4.02(m, 6H), 4.57(t, 2H), 7.14-7.53(m, 17H). |
| Target-48 | 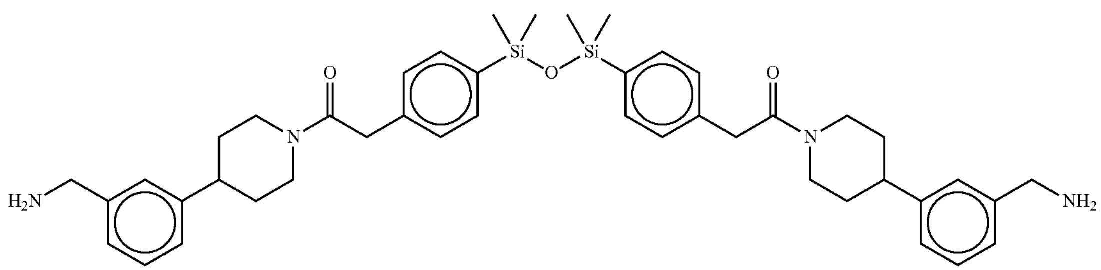 | Same as above. Isolated as TFA salt. Yield:- 11% | Mol. Wt:- 382.57 (monomer) 747.13 (Dimer) M.I. Peak observed: Monomer-383.05, Dimer-747.20 HPLC Purity:- Monomer-31.10%, Dimer- 67.89% ¹H NMR ACN:-0.289(s, 6H), 1.270-1.321(m, 2H), 1.423-1.507 (m, 2H), 1.679-1.708(d, 2H, J = 11.6 Hz), 1.760-1.791 (d, 1H, J = 12.4 Hz), 2.621 (t, 1H), 3.118-3.085(m, 1H), 3.785-3.652 (m, 2H), 3.952 (s, 2H), 4.593-4.022 (d, 1H), 7.142-7.318 (m, 5H), 7.488-7.409 (d, 1H), 7.504-7.540 (d, 1H), |

TABLE 8-continued
REACTION CONDITIONS & ANALYTICAL DATA
| Comp. No. | Structure | Brief Reaction conditions | Analytical data |
|---|---|---|---|
| Target-49 | 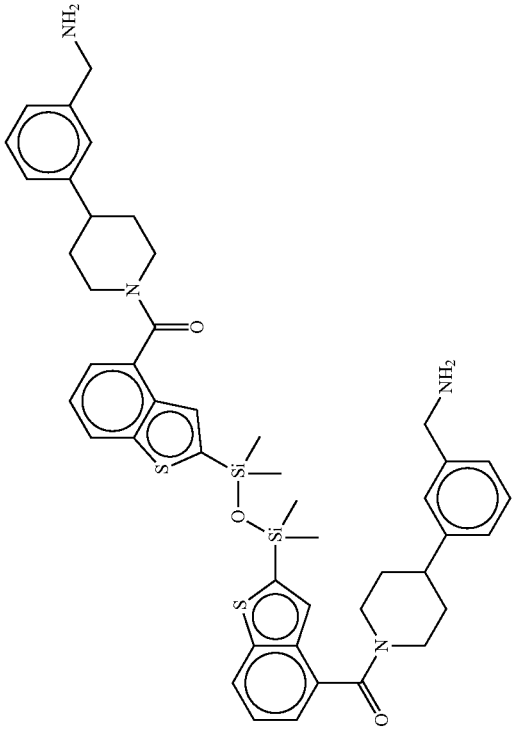 | Same as above. Isolated as TFA salt. Yield:- 25% | Mol. Wt:- 425.63 (monomer) 831.25 (Dimer) M.I. Peak observed: Monomer-424.95 Dimer- 831.25 HPLC Purity:- Monomer-24.56 Dimer-73.69 $^1$H NMR ACN:- 0.42-0.46(d, 6H), 1.45-1.72(m, 4H), 2.75-2.99(m, 3H), 3.42-3.44(m, 1H), 4.00-4.06(d, 2H), 4.76-4.79(m, 1H), 7.22-7.56(m, 7H), 7.97-8.02(m, 1H), 7.861(s, 3H). |

Step-5 & 6

Compound B-47 was deprotected using TFA in DCM as per method described earlier and deprotected product was heated with dimethylvinylethoxysilane Pd(II)acetate, tri(O-tolyl)phosphine in dimethyl formamide-Water (2:1) using sodium acetate as base. Reaction was monitored by LCMS. After consumption of starting, reaction mass was cooled to room temp., quenched with water, extracted with ethyl acetate and ethyl acetate extract was concentrated in vacuum after drying over sodium sulfate to get the crude product which was purified by reverse phase preparative HPLC. Product was isolated as TFA salt.

TABLE 9

| | REACTION CONDITIONS & ANALYTICAL DATA | |
|---|---|---|
| Target-47-Vinyl | 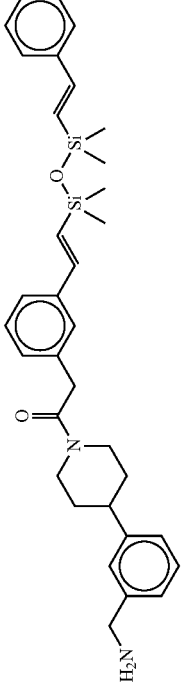 | 1): B-47, DCM, TFA(3.3 Vol), RT, 3 Hrs, 80% 2): Dimethylvinylethoxy silane (4 eq.), Pd(II)acetate (30% bywt), Tri(O-tolyl) phosphine (15% by wt) DMf(10 Vol), sodium acetate(5 eq), 80° C. 2 hrs. Prep HPLC. Isolated as TFA salt. 10%. | Mol. Wt:- 408.61monomer Dimer-799.20 M.I. Peak observed :- 431.05(monomer Na+), 800(Dimer) HPLC Purity:- 96.44% $^1$H NMR DMSO-d6:- 0.242(s, 6H), 1.386-1.465(m, 2H), 1.715-1.777 (t, 2H), 2.605-2.668(t, 1H), 2.735-2.764 (t, 1H), 3.064-3.125(t, 1H), 3.692-3.680 (m, 2H), 3.995-4.008 (d, 2H, J = 5.2 Hz), 4.063-4.096 (d, 1H, J = 13.2 Hz), 4.545-4.575 (1H, d, J = 12 Hz), 6.459-6.508 (d, 1H, J = 19.6 Hz), 6.941-6.989 (d, 1H, J = 19.2 Hz), 7.166-7.380 (m, 8H), 8.149(bs, 3H) |

Example 4

Synthesis of Tryptase Inhibitors with Silanols Functionality

Seventeen final targets with Silanol functionality were synthesized. These compounds were synthesized by three different approaches as given below.

Approach-1:—

Desired halo aryl carboxylic acids were first coupled with protected 4-(3-Aminomethyl phenyl) piperidine or 5-Aminomethyl Spiro [benzofuran-3,4'-piperidine]. Coupled product was reacted with 1,2-diethoxy-1,1,2,2-tetramethyldisilane to get ethoxydimethyl(Aryl)silanes, which upon treatment with acetic acid and subsequent deprotection afforded in the title compounds. 11 compounds were synthesized from Approach-1.

General Synthetic Scheme:

Approach-2:—

Desired halo aryl carboxylic acids were esterified and converted to silanols as mentioned above and subsequently hydrolyzed to carboxylic acid with dimethyl silanols functionality as mixture of monomer and dimer which was coupled with appropriate Core shown in the Synthetic Scheme Followed by deprotection. Most of the silanols were isolated as mixture of monomer and dimer.

The details of intermediates (A) sourced/synthesised as per literature methods/synthesised by developed adapted methods are given below. 4 compounds were synthesized from Approach-2

General Synthetic Scheme:

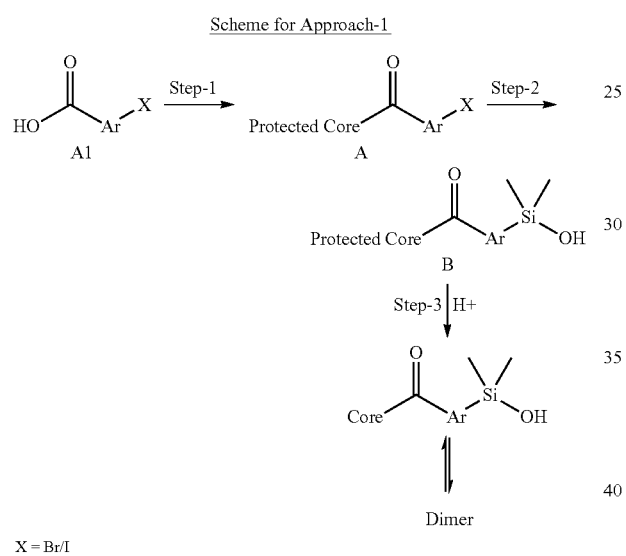

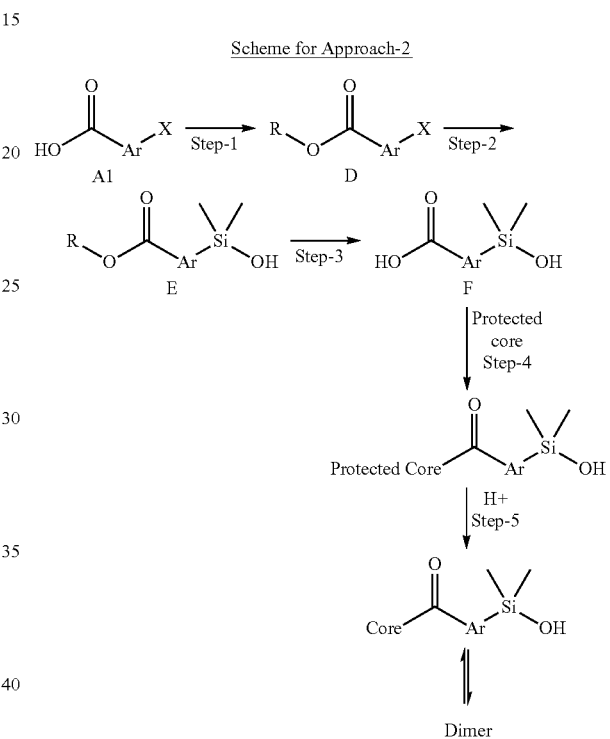

X = Br/I
Protected Cores

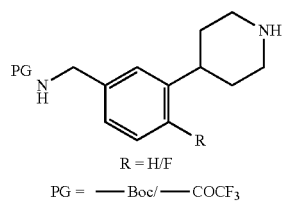

R = H/F
PG = ——Boc/——COCF₃

Or

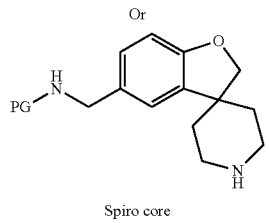

Spiro core

Core-1
R = H, PG = Boc
Core-2
R = F, PG = ——COCF3
Core-3
R = H, PG = ——COCF3
Core-4: -Spiro core X = Br/I
Protected Cores

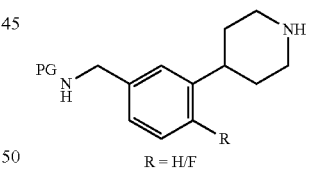

R = H/F
PG = ——Boc/——COCF₃

Or

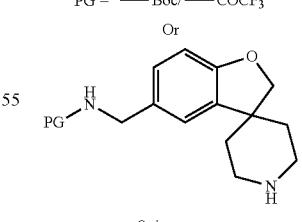

Spiro core

Core-1
R = H, PG = Boc
Core-2
R = F, PG = ——COCF3
Core-3
R = H, PG = ——COCF3
Core-4: -Spiro core Approach-3:—

Suitably substituted dimethyl (aryloxymethyl) silanols were synthesized by alkylation of Aryl hydroxyl carboxylates and subsequent hydrolysis of ester and coupled with the desired protected core. Deprotection on the amino methyl functionality afforded corresponding carboxylic acids with O-silanol. 2 compounds were synthesized from Approach-3.

General Synthetic Scheme:

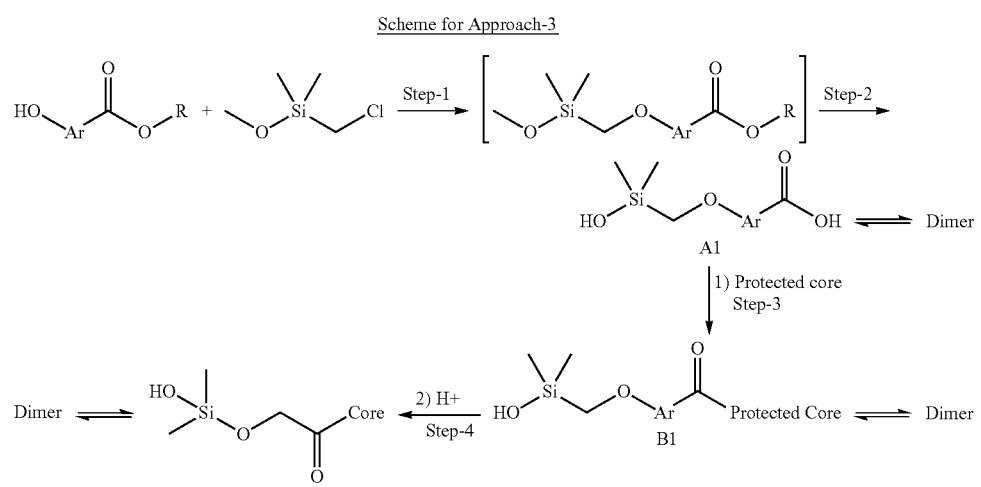

| Comp. No. | Structure |
|---|---|
| A1-35 | 3'-bromo-[1,1'-biphenyl]-3-carboxylic acid<br>Procured form commercial source |於

The details of intermediates (A) sourced/synthesised as per literature methods/synthesised by adapted methods are given below.

| Comp. No. | Structure |
|---|---|
| A1-11 | 7-bromo-1-naphthoic acid |
| A1-32 | 4-bromo-1H-indole-2-carboxylic acid<br>Procured form commercial source |
| A1-52 | 8-bromo-2-naphthoic acid<br>journal of chemical Society, 1926, U.S. Pat. No. 4,966,975 |
| A1-62 | 2'-bromo-[1,1'-biphenyl]-3-carboxylic acid<br>Angew. Chem, Int. Edn. 43(40), 5331-5335, 2004 |

| Comp. No. | Structure |
|---|---|
| A1-120F | 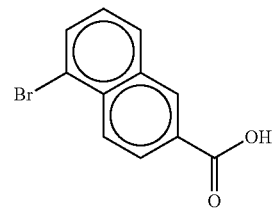<br>5-bromo-2-naphthoic acid<br>US 2008/58423 A1 |
| A1-122 | 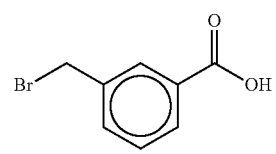<br>3-(bromomethyl)benzoic acid<br>WO2011/21209 A1, 2011 |
| A1-129 | 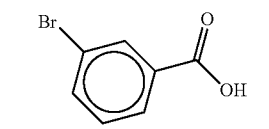<br>3-bromobenzoic acid<br>Procured form commercial source |
| A1-129 S-Me | 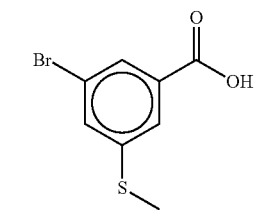<br>3-bromo-5-(methylthio)benzoic acid<br>WO2009/110985 A2, 2009; |
| A1-137 | 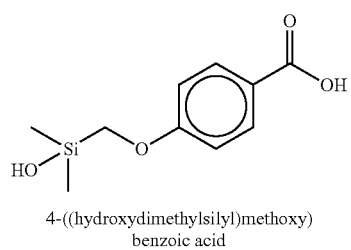<br>4-((hydroxydimethylsilyl)methoxy)benzoic acid |
| A1-138 | 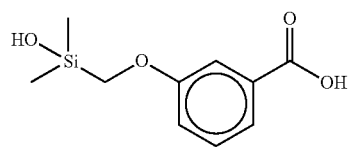<br>3-((hydroxydimethylsilyl)methoxy)benzoic acid |

| Comp. No. | Structure |
|---|---|
| A1-148 | 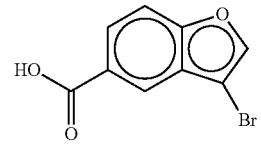<br>3-bromobenzofuran-5-carboxylic acid<br>1) US2003/232853; (2003)<br>2) *J. Med. Chem*, 38; (1995); 3094-3105<br>3) US2011/82098 |
| A1-149 | 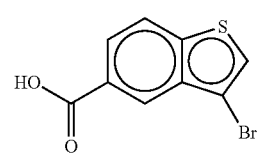<br>3-bromobenzo[b]thiophene-5-carboxylic acid<br>1) J. Med. Chem, 52; (2009); 6270-6286<br>2) US2006/52378; (2006)<br>3) BMCL, 9; (1999); p. 759-764<br>4) US5340833; (1994) |
| A1-152 | 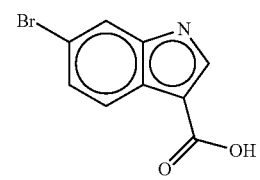<br>6-bromo-1H-indole-3-carboxylic acid<br>Procured form commercial source |

Synthesis of 4-((hydroxyl dimethyl silyl) methoxy) benzoic acid (A1-137)

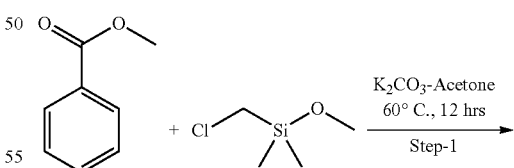

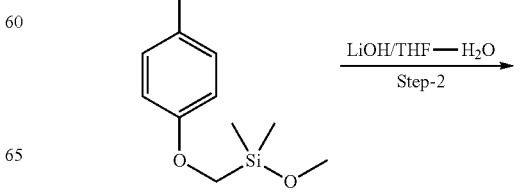

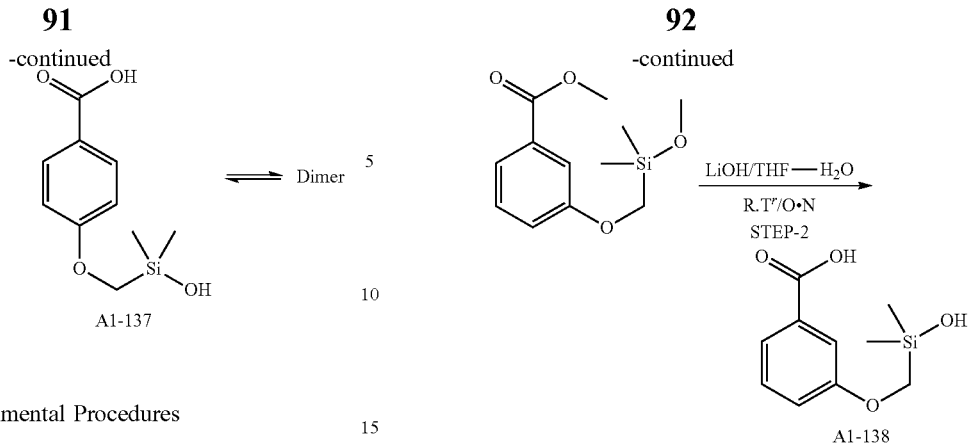

A1-137

Experimental Procedures

Step-1

A stirred solution of methyl-4-hydroxy benzoate (1 g, 6.58 mmol) and potassium carbonate (2.72 g, 19.7 mmol) in acetone (30 mL) stirred at room-temperature for 15 min. and charged with chloromethyl dimethyl methoxy silane (1.4 mL, 9.8 mmol) and heated to 60° C. for 72 hr. The solvent was concentrated in vacuo and the residue was diluted with water (20 mL) and extracted with ethyl acetate (3×25 mL). The combined organic layer was washed with brine (2×20 mL), dried over sodium sulfate, filtered, and concentrated in vacuo resulting in a crude product which was purified by column chromatography to get a colorless oil.

Yield: 770 mg, 46.10%
HPLC purity: 95.35%,
$^1$H NMR (400 MHz, CDCl$_3$): δ 0.24 (d, J=12 Hz, 6H), 2.74 (s, 3H), 3.60 (s, 2H), 3.88 (s, 3H), 6.96 (d, J=8.8 Hz, 2H), 7.98 (d, J=8.4 Hz, 2H).

Step-2

A stirred solution of step-1 product (770 mg, 3.0 mmol) in THF/water (1:1) (20 mL) was charged with lithium hydroxide (109 mg, 4.5 mmol) and stirred at room-temperature for 24 hrs. The solvent was concentrated in vacuo and residue was acidified to pH=2 using 1N KHSO$_4$ and was extracted with ethyl acetate (2×25 mL). The combined organic layer was washed with brine (2×20 mL), dried over sodium sulfate, filtered, and concentrated in vacuo to get a yellow solid (Qty-540 mg)

Yield: 540 mg, 78.83%.
Mol Wt: 226.30
MS (ES+): in/z=226.10 [MH$^+$], (ES−)=225.44 [MH$^−$]
$^1$H NMR (400 MHz, DMSO-d$_6$): δ 12.9 (bs, 1H), 7.49 (t, J=5.4 Hz, 2H), 7.39 (t, J=7.9 Hz, 1H), 7.21 (dd, J=8.0, 2.9 Hz, 1H), 3.62 (d, J=22.5 Hz, 2H), 0.18 (s, 6H).

Synthesis of 3-((hydroxyl dimethyl silyl) methoxy) benzoic acid (A1-138)

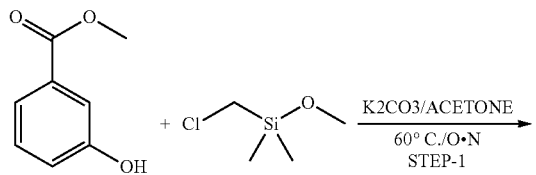

A1-138

Experimental Procedures

Step-1

A stirred solution of methyl-3-hydroxy benzoate (1 g, 6.578 mmol) in acetone (30 mL) and potassium carbonate (2.72 g, 19.7 mmol) was stirred at room-temperature for 15 min and then charged with chloromethyl dimethyl methoxy silane (1.4 mL, 9.8 mmol) and heated to 60° C. for 72 hrs. The solvent was concentrated in vacuo and diluted with water (20 mL) and extracted with ethyl acetate (3×25 mL). The combined organic layer was washed with brine (2×20 mL), dried over sodium sulfate, filtered, and concentrated in vacuo resulting in a crude product that was purified by column chromatography to get the colorless oil. (Qty-1.03 g), Yield: 1.03 g, 67%
HPLC purity: 99.25%,
$^1$H NMR (400 MHz, CDCl$_3$): δ 7.61 (d, J=3.4 Hz, 1H), 7.33 (t, J=8.0 Hz, 1H), 7.27-7.23 (m, 1H), 7.14 (d, J=8.0 Hz, 1H), 3.92 (s, 3H), 3.59 (s, 3H), 0.23 (d, J=11.5 Hz, 6H).

Step-2

A stirred solution of step-1 product (1.03 g, 4.5 mmol) in THF/water (1:1) (20 mL) was charged with lithium hydroxide (145 mg, 6.04 mmol) and stirred at room-temperature for 24 hr. The solvent was concentrated in vacuo and residue was acidified to pH=2 using 1N KHSO$_4$ and was extracted with ethyl acetate (2×25 mL). The combined organic layer was washed with brine (2×20 mL), dried over sodium sulfate, filtered, and concentrated in vacuo resulting in a yellow solid as crude product. (Qty-440 mg)

Yield: 440 mg, 48.83%
Mol Wt-226.30,
MS (ES−): m/z=225.18 [MH$^−$]

The detailed description of the amide intermediates and Final Targets synthesized by three different approaches is given below.

Approach-1

Step-1

Coupling of the aryl bromo carboxylic acids (A1) was carried out with appropriate protected core as shown in the synthetic scheme as per conditions mentioned in the table below.

| Comp. No. | Structure | Brief Reaction conditions | Analytical data |
|---|---|---|---|
| A-62 | 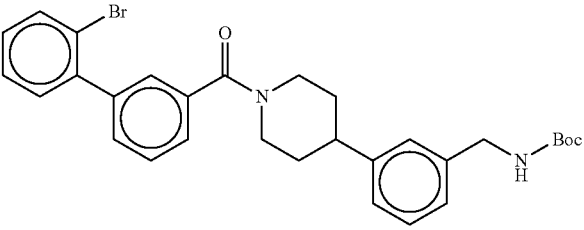<br>tert-butyl 3-(1-(2'-bromo-[1,1'-biphenyl]-3-carbonyl)piperidin-4-yl)benzylcarbamate | tert-butyl-3-(piperidin-4-yl) benzyl carbamate, (1.2 eq.), EDCI (1.5 eq.) DMAP (0.5 eq.), DCM (5 ml) R.T. 12 h; | Yield: 59%<br>Mol. Wt.: 549.5<br>MS (ES+): m/z = 549/551.4 [MH$^+$], |
| A-35 | 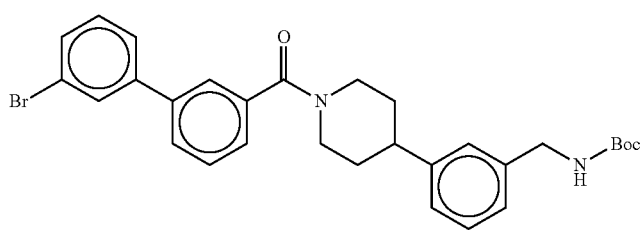<br>tert-butyl 3-(1-(3'-bromo-[1,1'-biphenyl]-3-carbonyl)piperidin-4-yl)benzylcarbamate | tert-butyl-3-(piperidin-4-yl) benzyl carbamate, (1.2 eq.), EDCI (1.5 eq.) DMAP (0.5 eq.), DCM R.T. 15 h; | Mol. Wt.: 549.5<br>MS (ES+): m/z = 549/551.3 [MH$^+$],<br>Yield:- 76% |
| A-152 | 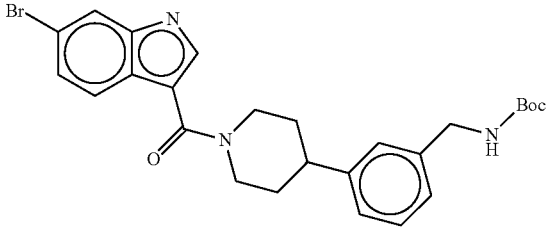<br>tert-butyl 3-(1-(6-bromo-1H-indole-3-carbonyl)piperidin-4-yl)benzylcarbamate | tert-butyl-3-(piperidin-4-yl) benzyl carbamate, (1 eq.), EDCI (1.5 eq.) HOBt (1.5 eq.), DIEA (2 eq.) DMF (15 vol) R.T. 15 h; | Mol. Wt.: 512.44<br>MS (ES+): m/z = 512/514.1 [MH$^+$]<br>Yield:- 55% |
| A-32 | 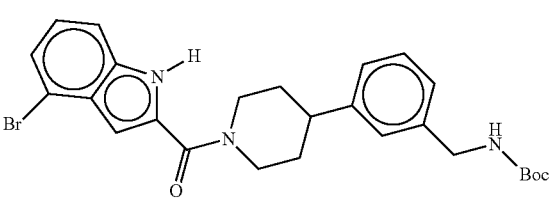<br>tert-butyl 3-(1-(4-bromo-1H-indole-2-carbonyl)piperidin-4-yl)benzylcarbamate | Tert-Butyl 3-(piperidin-4-yl) benzyl carbamate, (1 eq.), EDCI (1.5 eq.) HOBt (1.5 eq.), DIEA (2 eq.) DMF (15 vol) R.T. 15 h; | Mol. Wt.: 512.44<br>MS (ES+): m/z = 512/514.4 [MH$^+$]<br>Yield;- 62% |
| A-152 N-Methyl | 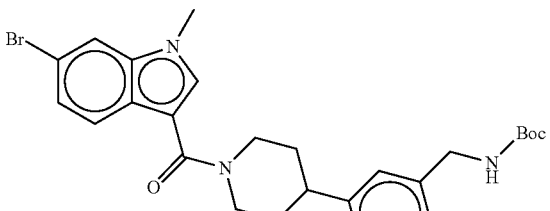<br>tert-butyl 3-(1-(6-bromo-1-methyl-1H-indole-3-carbonyl)piperidin-4-yl)benzylcarbamate | Synthesized by reacting A-152 with methyl iodide (3 eq.) and potassium carbonate (1.5 eq.) in DMF (50 vol) at R.T. for 2 hrs, Purified by column chromatography over silica gel after quenching with water and isolation by extraction with DCM.<br>Yield:- 97% | Mol. Wt.: 526.47<br>MS (ES+): m/z = 526/528.2 [MH$^+$]<br>Yield:- 97% |

-continued

| Comp. No. | Structure | Brief Reaction conditions | Analytical data |
|---|---|---|---|
| 129 S-Me | (4-(3-(aminomethyl)phenyl)piperidin-1-yl)(3-bromo-5-(methylthio)phenyl)methanone | tert-butyl-I3-(piperidin-4-yl) benzyl carbamate, (1 eq.), EDCI (1.5 eq.) HOBt (1.5 eq.), DIEA (2.5 eq.) DMF (15 vol) R.T. 15 h; | Mol. Wt.: 518.07 MS (ES+): m/z = 518/520.1 [MH$^+$] Yield:- 38% |
| A-11 | tert-butyl 3-(1-(7-bromo-1-naphthoyl) piperidin-4-yl)benzylcarbamate | | |
| A-148 | tert-butyl 3-(1-(3-bromobenzofuran-5-carbonyl) piperidin-4-yl)benzylcarbamate | tert-butyl-I-3-(piperidin-4-yl) benzyl carbamate, (1 eq.), EDCI (1.5 eq.) DMAP (1.2 eq.), DCM (25 vol) R.T. 15 h; | Yield:- 91%, Mol. Wt:-513.42 MS (ES+): m/z = 513/515.00 [MH$^+$] |
| A-149 | tert-butyl 3-(1-(3-bromobenzo[b]thiophene-5-carbonyl)piperidin-4-yl)benzylcarbamate | tert-butyl-3-(piperidin-4-yl)benzyl carbamate (1 eq.), EDCI.HCl (1.5 eq.), DMAP (1.2 eq.), DCM(20 vol), RT, 4 h, Purified by column chromatography | Yield:- 71%, Mol. Wt:- 529.49 MS (ES+): m/z = 529/531 [MH$^+$] |

| Comp. No. | Structure | Brief Reaction conditions | Analytical data |
|---|---|---|---|
| A-120F | N-(3-(1-(5-bromo-2-naphthoyl)piperidin-4-yl)-4-fluorobenzyl)-2,2,2-trifluoroacetamide | 2,2,2-trifluoro-N-(4-fluoro-3-(piperidin-4-yl)benzyl)acetamide (1.3 eq.), EDCl.HCl (1.5 eq.), DMAP (2 eq.), DCM(20 vol), RT, 4 h, | Yield:- 80%, Mol. Wt:- 537.34 MS (ES+): m/z = 536/538.20 [MH+] |
| A-129 | tert-butyl 3-(1-(3-bromobenzoyl)piperidin-4-yl)benzylcarbamate | tert-butyl3-(piperidin--4-yl) benzyl carbamate (1.3 eq.), 3-bromo benzoic acid, EDCl.HCl (1.5 eq.), DMAP (2 eq.), DCM(20 vol), RT, 4 h, | Yield:- 80%, Mol. Wt:- 473.40 MS (ES+): m/z = 495.95/497.95 [MH+ + Na] |

Step-2

Stirred suspension of coupled products from step-1 in N-methyl pyrrolidine was degassed with argon and, palladium chloride, di-isopropyl ethyl amine, and 1,2-diethoxy-1,1,2,2, tetra methyl silane were added to it. Reaction mixture was heated to ~60° C. and reaction monitored by LCMS till most of the starting material was consumed. There after acetonitrile, 1N aq. acetic acid and 2-(dimethyl amino) ethane thiol hydrochloride was added and reaction mixture stirred for 2 hr at room temperature. Reaction mixture was diluted with water, filtered through celite, extracted with ethyl acetate and the combined ethyl acetate extracts were dried over sodium sulfate, filtered, and concentrated in vacuo to get the crude products which were sufficiently pure to be used for silylation.

The details of the compounds are given below.

| Comp. No. | Structure | Brief Reaction conditions | Analytical data |
|---|---|---|---|
| B-62-Si | tert-butyl 3-(1-(2'-(hydroxydimethylsilyl)-[1,1'-biphenyl-3-carbonyl)piperidin-4-yl)benzylcarbamate | 1-2 diethoxy 1,1,2,2, tetra methyl disilane (3 eq.) PdPPh$_3$ (0.05 eq), potassium acetate (4 eq.), NMP (75 vol), 140° C., Microwave 10 min. Reaction mass quenched with water extracted with ethyl acetate and purified over neutral silica to get the product | Yield:- 7.5% Mol. Wt.: 544.28 MS (ES+): m/z = 567 [MH+ + Na] |
| B-35-Si | tert-butyl 3-(1-(3'-(hydroxydimethylsilyl)-[1,1'-biphenyl]-3-carbonyl)piperidin-4-yl)benzylcarbamate | 1-2 diethoxy 1,1,2,2, tetra methyl disilane (3 eq.) PdPPh$_3$ (0.05 eq), potassium acetate (4 eq.), NMP (75 vol), 140° C., Microwave 10 min. Reaction mass quenched with water extracted with ethyl acetate and purified over neutral silica to get the product | Yield:- 10% Mol. Wt.: 544.28 MS (ES+): m/z = 567 [MH+ + Na] |

-continued

| Comp. No. | Structure | Brief Reaction conditions | Analytical data |
|---|---|---|---|
| B-152 N-Methyl | tert-butyl 3-(1-(6-(hydroxydimethylsilyl)-1-methyl-1H-indole-3-carbonyl-piperidin-4-yl)benzylcarbamate | 1-methyl-2-pyrrolidinone (30 vol.), 2-(di-t-butylphosphino) biphenyl (0.1 eq.) and DIEA (3.0 eq.). PdCl$_2$ (0.05 eq.) 1,2-diethoxy-1,1,2,2-tetramethyl disilane (1.1 eq.) 60° C. 10 h. | White solid; Yield: 38% Mol. Wt.: 521.72 MS (ES+): m/z = 522 [MH$^+$] |
| B-152 | tert-butyl 3-(1-(6-(hydroxydimethylsilyl)-1H-indole-3-carbonyl-piperidin-4-yl)benzylcarbamate | 1-methyl-2-pyrrolidinone (30 vol.), 2-(di-t-butylphosphino) biphenyl (0.1 eq.) and DIEA (3.0 eq.). PdCl$_2$(0.05 eq.) 1,2-diethoxy-1,1,2,2-tetramethyl disilane (1.1 eq.) 60° C. h. | White solid; Yield: 33% Mol. Wt.: 507.70 MS (ES+): m/z = 508 [MH$^+$] |
| B-32 Si | tert-butyl 3-(1-(4-(hydroxydimethylsilyl)-1H-indole-2-carbonyl-piperidin-4-yl)benzylcarbamate | 1-methyl-2-pyrrolidinone (30 vol.), 2-(di-t-butylphosphino) biphenyl (0.1 eq.) and DIEA (3.0 eq.). PdCl$_2$(0.05 eq.) 1,2-diethoxy-1,1,2,2-tetramethyl disilane (1.1 eq.) 60° C. 10 h. | White solid; Yield: 26% Mol. Wt.: 507.70 MS (ES+): m/z = 508 [MH$^+$], 530 [MH$^+$ + Na] |
| B-129 S-Me | tert-butyl 3-(1-(3-(hydroxydimethylsilyl)-5-(methylthio)benzoyl) piperidin-4-yl)benzylcarbamate | 1-methyl-2-pyrrolidinone (30 vol.), 2-(di-t-butylphosphino) biphenyl (0.1 eq.) and DIEA (3.0 eq.). PdCl$_2$(0.05 eq.) 1,2-diethoxy-1,1,2,2-tetramethyl disilane (1.1 eq.) 60° C. 10 h. | White solid; Yield: (26%) Mol. Wt.: 514.75 MS (ES+): m/z = 515 [MH$^+$] |
| B-11 si | tert-butyl 3-(1-(7-(hydroxydimethylsilyl)-1-naphthoyl)piperidin-4-yl)benzylcarbamate | 1,2-diethoxy-1,1,2,2-tetarmethyl silane (3 eq.), PdCl2 (0.1 eq), DTBPBP (0.2 eq), DIPEA (6 eq), NMP, 50° C., 14 hrs. | Yield 81.6%. Mol. Wt: 518.72 MS (ES+): m/z = 519.05 [MH$^+$] |

-continued

| Comp. No. | Structure | Brief Reaction conditions | Analytical data |
|---|---|---|---|
| B-148 | tert-butyl 3-(1-(3-(hydroxydimethylsilyl)benzofuran-5-carbonyl-piperidin-4-yl)benzylcarbamate | 1,2-diethoxy-1,1-2,2-tetarmethyl silane (3 eq.), PdCl2 (0.1 eq), DTBPBP (0.2 eq), DIPEA (6 eq), NMP, 50° C., 14 hrs. | Yield 40%. Mol. Wt: 508.68 MS (ES+): m/z = 531.20 [MH$^+$ + Na] |
| B-149 | tert-butyl 3-(1-(3-(hydroxydimethylsilyl)benzo[b]thiophene-piperidin-4-yl)benzylcarbamate | 1,2-diethoxy-1,1-2,2-tetarmethyl silane (3 eq.), PdCl2 (0.1 eq), DTBPBP (0.2 eq), DIPEA (6 eq), NMP, 50° C., 14 hrs. | Yield 60.6%. Mol. Wt: 524.75 MS (ES+): m/z = 547.35 [MH$^+$ + Na] |
| B-120F | 2,2,2-trifluoro-N-(4-fluoro-3-(1-(5-(hydroxydimethylsilyl)-2-naphthoyl)piperidin-4-yl)benzyl)acetamide | 1,2-diethoxy-1,1-2,2-tetarmethyl silane (3 eq.), PdCl$_2$ (0.1 eq), DTBPBP (0.2 eq), DIPEA (6 eq), NMP, 50° C., 5 hrs. | Yield 55%. Mol. Wt: 436.39 MS (ES+): m/z = 437.10 [MH$^+$] |
| B-129 | tert-butyl 3-(1-(3-(hydroxydimethylsilyl)benzoyl)piperidin-4-yl)benzylcarbamate | 1,2-diethoxy-1,1-2,2-tetarmethylsilane(3 eq.), PdCl2(0.1 eq), DTBPBP(0.2 eq), DIPEA (6 eq), NMP, 50° C., 5 hrs. | Yield 25%. Mol. Wt: 468.66 MS (ES+): m/z = 369 [MH$^+$ − Boc], 719.30 [MH$^+$ − Boc] |

Step-3

Products of Step-2 were deprotected as per reaction conditions mentioned in the table below to get the silanols.

In most of the cases, Compounds were found to be mixture of monomer & dimer as per HPLC as well as NMR data. All reactions were done on 100-200 mg scale.

| Comp. No. | Structure | Brief Reaction conditions | Analytical data |
|---|---|---|---|
| 62-Si | (4-(3-(aminomethyl)phenyl)piperidin-1-yl) (2'-(hydroxydimethylsilyl)-[1,1'-biphenyl]-3-yl)methanone | $H_3PO_4$ (6 eq.). in dichloromethane. Stirring at room temp. for 12 hr. Quenched with water, purification by prep. TLC (15% Methanol in chloroform) | Yield: 75% Mol Wt: 444.6, MS (ES+): m/z = 467 [MH$^+$ + Na] HPLC purity: 80% (220 nm). $^1$H NMR (400 MHz, DMSO-$d_6$ in 0.03% TMS): δ 7.80-7.67 (m, 5H), 7.64-7.53 (m, 5H), 7.50-7.11 (m, 4H), 4.64 (s, 1H), 3.68 (d, J = 4.3 Hz, 2H), 2.79 (t, J = 15.7 Hz, 5H), 1.68-1.40 (m, 4H), 0.04--0.20 (m, 6H). |
| 35-Si | (4-(3-(aminomethyl)phenyl)piperidin-1-yl) (3'-(hydroxydimethylsilyl)-[1,1'-biphenyl]-3-yl)methanone | $H_3PO_4$ (6 eq.). in dichloromethane. Stirring at room temp. for 12 hr. DCM was decanted, Neutralization with 50% NaOH to pH ~ 8 extractions and purification by prep. TLC (15% Methanol in chloroform | Yield: 50%). MS (ES+): m/z = 467[MH$^+$ + Na] HPLC: (254 nm) 90.66% $^1$H NMR (400 MHz, CD$_3$CN): δ 7.57 (s, 1H), 7.44-7.05 (m, 8H), 6.99-6.77 (m, 4H), 5.13 (d, J = 5.4 Hz, 1H), 4.43 (s, 1H), 3.43 (d, J = 10.6 Hz, 2H), 2.92-2.76 (m, 2H), 2.51 (tq, = 9.7, 5.0 Hz, 3H), 1.66-1.55 (m, 2H), 1.48-1.31 (m, 2H), 0.12-0.03 (m, 6H) |
| 152 N-Methyl | (4-(3-(aminomethyl)phenyl)piperidin-1-yl) (6-(hydroxydimethylsilyl)-1-methyl-1H-indol-3-yl)methanone | $H_3PO_4$ (2.5 eq.). in dichloromethane. Stirring at room temp. for 1 hr. Conc. For removal of DCM, Neutralization with NaOH to pH ~ 8 extractions and purification by prep. TLC (15% Methanol in chloroform | White solid; Yield: 39% Mol. Wt.: 421.61 (monomer), MS (ES+): m/z = 422 [MH$^+$] (monomer), HPLC Purity: 89.59% $^1$H NMR (400 MHz, CD$_3$OD): 7.74-7.67 (m, 2H), 7.63 (s, 1H), 7.41 (d, J = 8.0 Hz, 1H), 7.35-7.29 (m, 2H), 7.26-7.19 (m, 2H), 4.64-4.48 (m, 2H), 3.90 (s, 5H), 3.25-3.10 (m, 2H), 2.96-2.84 (m, 1H), 1.84-1.70 (m, 2H), 1.66-1.54 (m, 1H), 0.40 (s, 6H) |
| 152 | (4-(3-(aminomethyl)phenyl)piperidin-1-yl) (6-(hydroxydimethylsilyl)-1H-indol-3-yl)methanone | $H_3PO_4$ (2.5 eq.). in dichloromethane. Stirring at room temp. for 1 hr. Conc. For removal of DCM, Neutralization with NaOH to pH ~ 8 extractions and purification by prep. TLC (15% Methanol in chloroform | White solid; Yield: 46% Mol. Wt.: 407.58 (monomer), 796.40 (dimer), MS (ES+): m/z = 408 [MH$^+$] (monomer), 819 [MH$^+$ + Na] (dimer), HPLC Purity: 95.92% $^1$H NMR (400 MHz, CD$_3$OD): 7.75-7.60 (m, 3H), 7.42-7.20 (m, 5H), 4.65-4.48 (m, 2H), 3.96 (s, 2H), 3.25-3.10 (m, 2H), 2.98-2.85 (m, 1H), 1.85-1.70 (m, 2H), 1.66-1.54 (m, 2H), 0.38 (s, 6H) |
| 32-Si | (4-(3-(aminomethyl)phenyl)piperidin-1-yl) (4-(hydroxydimethylsilyl)-1H-indol-2-yl)methanone | $H_3PO_4$ (2.5 eq.). in dichloromethane. Stirring at room temp. For 1 hr. Conc. For removal of DCM, Neutralization with NaOH to pH ~ 8 extractions and purification by prep. TLC (15% Methanol in chloroform | White solid; Yield: 18% Mol. Wt.: 407.58 (monomer), 796.40 (dimer), MS (ES+): m/z = 408 [MH$^+$] (monomer), 819 [MH$^+$ + Na] (dimer), HPLC Purity: 86.55% $^1$H NMR (400 MHz, CD$_3$OD): 7.49 (d, J = 8.0 Hz, 1H), 7.36-7.18 (m, 6H), 7.06 (s, 1H), 4.80-4.70 (m, 2H), 3.91 (m, 2H), 3.60-3.46 (m, 1H), 3.02-2.90 (m, 1H), 2.86-2.68 (m, 1H), 2.02-1.93 (m, 2H), 1.86-1.75 (m, 2H), 0.44 (m, 6H) |

| Comp. No. | Structure | Brief Reaction conditions | Analytical data |
|---|---|---|---|
| 129-S-Me | (4-(3-(aminomethyl)phenyl)piperidin-1-yl)(3-(hydroxydimethylsilyl)-5-(methylthio)phenyl)methanone | 1,4-dioxane (30 mL/g) conc. HCl (1 mL/g) at room temp. 3 hrs, The reaction mixture was Concentrated in vacuo and purified by preparative HPLC. | Yield: 16%, Mol. Wt.: 414.64 (monomer), 811.26 (dimer) MS (ES+): m/z = 415 [MH$^+$] (monomer), 811 [MH$^+$] (dimer) HPLC Purity: 82.95%, $^1$H NMR (400 MHz, CD$_3$OD), monomer:dimer (48:34): 7.50-7.16 (m, 7H), 4.82-4.70 (m, 1H), 4.10 (s, 2H), 3.94-3.70 (m, 1H), 3.04-2.85 (m, 2H), 2.51, 2.47 (2s, 6H, monomer + dimer), 2.05-1.54 (m, 4H), 0.38 (s, 3H) |
| 11-Si | (4-(3-(aminomethyl)phenyl)piperidin-1-yl)(7-(hydroxydimethylsilyl)naphthalen-1-yl)methanone | trifluroacetic acid (3, vol) DCM (50 vol), RT, 4 h. | Yield 40%. Mol. Wt:- 418.60 (Monomer) 819.19(Dimer) MS (ES+): m/z = 419.15 [MH$^+$] (monomer) 841.45 [MH$^+$ + Na] (dimer) $^1$H NMR (400 MHz, DMSO-d$_6$): δ 8.01 (q, J = 26.6, 20.3 Hz, 2H), 7.64 (d, J = 40.2 Hz, 3H), 7.48 (d, J = 21.6 Hz, 1H), 7.27 (t, J = 17.9 Hz, 4H), 4.76 (d, J = 78.2 Hz, 1H), 3.97 (d, J = 22.4 Hz, 2H), 3.35-2.76 (m, 4H), 1.78 (m, 4H), 1.22 (s, 1H), 0.13-0.08 (m, 6H) |
| 148 | (4-(3-(aminomethyl)phenyl)piperidin-1-yl)(3-(hydroxydimethylsilyl)benzofuran-5-yl)methanone | trifluroacetic acid (2.5, vol) DCM (50 vol), RT, 1 h. | Yield 22%. Mol. Wt: 408.57 (Monomer) 799.12 (Dimer) MS (ES+): m/z = 409.20 [MH$^+$] (monomer) 799.45 [MH$^+$] (dimer) $^1$H NMR (400 MHz, DMSO-d$_6$, D$_2$O): δ 8.00-7.92 (m, 1H), 7.69-7.60 (m, 2H) 7.42-7.23 (m, 4H), 4.00 (s, 2H), 2.93-2.71 (m, 4H), 2.81 (t, J = 59.7 Hz, 1H), 1.83-1.61 (m, 4H), 0.40 (s, 6H). |
| 149 | (4-(3-(aminomethyl)phenyl)piperidin-1-yl)(3-(hydroxydimethylsilyl)benzo[b]thiophen-5-yl)methanone | trifluroacetic acid (2.5, vol) DCM(50 vol), RT, 2 h. | Yield 4%. Mol. Wt: 424.63 (Monomer) 831.25(Dimer) MS (ES+): m/z = 425.15 [MH$^+$] (Monomer) 831.40 [MH$^+$] (dimer) $^1$H NMR (400 MHz, DMSO-d$_6$, D$_2$O): δ 7.94-7.86 (m, 1H), 7.28 (d, J = 9.2 Hz, 2H), 7.41-7.34 (m, 5H) 4.02-3.92 (m, 2H), 2.94-2.67 (m, 5H), 1.86-1.53 (m, 4H), 0.39 (s, 6H) |

-continued

| Comp. No. | Structure | Brief Reaction conditions | Analytical data |
|---|---|---|---|
| 120-F | 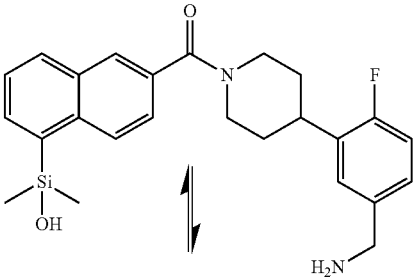<br>Dimer<br>(4-(5-(aminomethyl)-2-fluorophenyl)piperidin-1-yl)(5-(hydroxydimethylsilyl)naphthalen-2-yl)methanone | THF: MeOH, KOH, Room temperature, 2 hr | Yield 55%.<br>Mol. Wt: 436.59 (Monomer) 854.10(Dimer)<br>MS (ES+): m/z = 437.25 [MH$^+$] (Monomer)<br>855.15 [MH$^+$] (Dimer)<br>$^1$H NMR (400 MHz, DMSO-d$_6$) δ 8.21 (d, J = 9.7 Hz, 4H), 8.07-7.97 (m, 1H), 7.80 (t, J = 8.0 Hz, 1H), 7.56 (dt, J = 14.3, 6.6 Hz, 2H), 7.43 (d, J = 8.6 Hz, 1H), 7.35 (t, J = 6.6 Hz, 1H), 7.23 (t, J = 9.3 Hz, 1H), 4.69 (s, 1H), 4.02 (q, J = 5.9, 5.5 Hz, 2H), 3.31-3.09 (m, 4H), 2.96 (s, 1H), 1.77 (d, J = 70.6 Hz, 4H), 0.47 (d, J = 29.2 Hz, 6H) |
| 129 | 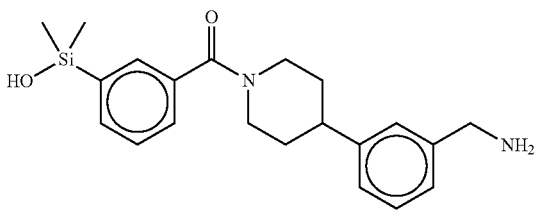<br>(4-(3-(aminomethyl)phenyl)piperidin-1-yl)(3-(hydroxydimethylsilyl)phenyl)methanone<br>Approach-1 | trifluroacetic acid (10, vol) DCM(20 vol), RT, 4 hr. | Yield:- 11.45%<br>Mol. Wt: 368.54<br>MS (ES+): m/z = 369 [MH$^+$] (monomer)<br>719.30 [MH$^+$](dimer)<br>HPLC Purity: (monomer) 47.85%, (dimer-) 49.42%<br>$^1$H NMR (400 MHz, CD$_3$CN, D$_2$O): δ 7.61 (t, J = 3.5 Hz, 2H), 7.56 (s, 1H), 7.41 (d, J = 5.2 Hz, 2H), 7.32 (q, J = 4.0, 3.2 Hz, 1H), 7.26 (dd, J = 14.9, 6.1 Hz, 2H), 4.68 (s, 1H), 4.04 (d, J = 9.9 Hz, 2H), 3.80-3.60 (m, 1H),, 2.87 (t, J = 13.1 Hz, 3H), 1.65 (dd, J = 44.9, 28.5 Hz, 4H), 0.32 (d, J = 6.8 Hz, 6H). |

Approach-2

Step-1

Bromo Esters were synthesized from the Bromo carboxylic acids (A1) detailed description given above as per conditions mentioned in the table. Details of the compounds synthesized are as below

| Comp. No. | Structure | Brief Reaction conditions | Analytical data |
|---|---|---|---|
| D-52 | 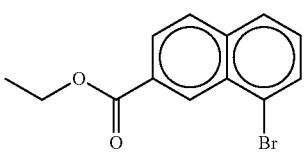<br>ethyl 8-bromo-2-naphthoate | thionyl chloride (1.2 eq), ethanol, 60° C., 5 hrs. | Yield 70.5%.<br>Mol. Wt:- 279.3<br>MS (ES+): m/z = 279/281.3 [MH+], |
| D-122 | 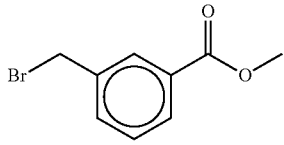<br>methyl 3-(bromomethyl)benzoate | WO2011/21209 A1, 2011 | |

| Comp. No. | Structure | Brief Reaction conditions | Analytical data |
|---|---|---|---|
| D-129-spiro | 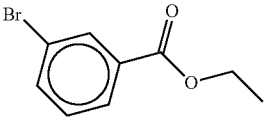<br>ethyl 3-bromobenzoate | thionyl chloride (1.2 eq), Methanol, 60° C., 5 hrs. | Yield 71.5%.<br>Mol. Wt:- 229.07<br>MS (ES+): m/z = 229/231.05 [MH⁺] |

Step-2

Stirred suspension of suitably substituted ester of aryl bromo carboxylic acid in N-methyl pyrrolidine was degassed with argon and charged with palladium chloride, diisopropyl ethyl amine & 1,2-diethoxy-1,1,2,2, tetra methyl silane. Reaction mixture was heated to ~60° C. and reaction monitored by LCMS till most of the starting material was consumed. Reaction mixture is then charged with acetonitrile, 1N aq. acetic acid and 2-(dimethyl amino) ethane thiol hydrochloride stirred for 2 hr at room temperature. Reaction mixture was then diluted with water, filtered through celite, extracted with ethyl acetate and ethyl acetate extracts were dried over sodium sulfate, filtered, and concentrated in vacuo to get the crude products which were sufficiently pure to be used for next step.

Required Bromo esters were synthesized by esterification of corresponding bromo acids by refluxing with alcohol and thionyl chloride. The details of bromo acids sourced/synthesised as per literature methods/synthesised by adapted methods are given below

| Comp. No. | Structure | Brief Reaction conditions | Analytical data |
|---|---|---|---|
| E-52 | 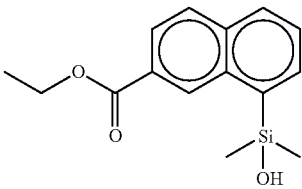<br>ethyl 8-(hydroxydimethylsilyl)-2-naphthoate | 1,2-diethoxy-1,1-2,2-tetarmethyl silane (3 eq.), PdCl2 (0.1 eq), DTBPBP (0.2 eq), DIPEA (6 eq), NMP, 50° C., 14 hrs. | Yield 44.5%.<br>Mol. Wt: 274.39<br>MS (ES+): m/z = 274.95 [MH⁺] |
| E-122 | 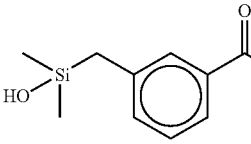<br>methyl 3-((hydroxydimethylsilyl)methyl)benzoate | 1-methyl-2-pyrrolidinone (30 vol.), 2-(di-t-butylphosphino) biphenyl (0.1 eq.) and DIEA (3.0 eq.). PdCl₂(0.05 eq.) 1,2-diethoxy-1,1,2,2-tetramethyl disilane (1.5 eq.) 60° C. 12 h. | Colorless oil,<br>Yield: 48%, Mol. Wt.: 224.33 (monomer), 430.64 (dimer)<br>MS (ES+): m/z = 431 [MH⁺] (dimer) |
| E-129-spiro | 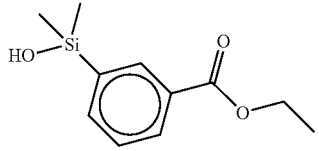<br>ethyl 3-(hydroxydimethylsilyl)benzoate | 1,2-diethoxy-1,1-2,2-tetarmethyl silane (3 eq.), PdCl2 (0.1 eq), DTBPBP (0.2 eq), DIPEA (6 eq), NMP, 50° C., 14 hrs. | Yield 71.5%<br>Mol. Wt:- 224.33<br>MS (ES+): m/z = 224.95 [MH⁺] |

Step-3

Silanol esters from step-5 were hydrolyzed as per conditions mentioned in the table below to get the aryl carboxy acids with silanols functionality in the form of mixture of monomer and dimer. Details of the compounds synthesized are as below

| Comp. No. | Structure | Brief Reaction conditions | Analytical data |
|---|---|---|---|
| F-52 | 8-(hydroxydimethylsilyl)-2-naphthoic acid | NaOH (6.00 eq.). In 1:1 mixture of THF: Water (25 vol). Stirring at 50° C. for 7 hrs. Conc. For removal of THF, Acidified with KHSO$_4$ to pH ~3 extraction and concentration of organic solvent. TLC(20% Ethyl acetate in n-Hexane) | Yield 80.5%. Mol. Wt: 246.33 Ionization not observed in LCMS, used as it is for next step, characterization done in next coupling step Monitored on TLC and stained in bromo cresol. |
| F-122 | 3-((hydroxydimethylsilyl)methyl) benzoic acid | LiOH (3.00 eq.). in 1:1 mixture of THF:Water(25 vol). Stirring at room temp. for 3 hrs. Conc. For removal of THF, acidified with 2N HCl to pH ~2 extraction and concentration of organic solvent. TLC (20% ethyl acetate in n-Hexane) | Off-white solid Yield: 65%, Monitored on TLC and stained in bromo cresol, Mass not seen in ESMS, . silyl ester was characterized, characterization done in next coupling step. |
| F-129-spiro | 3-(hydroxydimethylsilyl)benzoic acid | NaOH (6.00 eq.). In 1:1 mixture of THF: Water (25 vol). Stirring at 50° C. for 14 hrs. conc. For removal of THF, acidified with KHSO$_4$ to pH ~ 3 extractions and concentration of organic solvent. TLC (20% ethyl acetate in n-Hexane | Yield 93.5%. Mol. Wt:- 196.28 Ionization not observed in LCMS, used as it is for next step, characterization done in next coupling step Monitored on TLC and stained in bromo cresol.. |

Step-4

Coupling of the carboxylic acids was carried out with protected 4-(3-Aminomethyl phenyl) piperidine as per conditions mentioned in the table below.

| Comp. No. | Structure | Brief Reaction conditions | Analytical data |
|---|---|---|---|
| B-52-spiro | tert-butyl ((1'-(8-(hydroxydimethylsilyl)-2-naphthoyl)-2H-spiro[benzofuran-3,4'-piperidin]-5-yl)methyl)carbamate | tert-butyl ((2H-spiro[benzofuran-3,4'-piperidin]-5-yl)methyl)carbamate (1 eq.), EDCl.HCl (1.5 eq.), DMAP (1.2 eq.), DCM(20 vol), RT, 4 h, Purified by column chromatography | Yield 93%. Mol. Wt: 546.73 MS (ES+): m/z = 547.20 [MH$^+$] |

| Comp. No. | Structure | Brief Reaction conditions | Analytical data |
|---|---|---|---|
| B-52 | 2,2,2-trifluoro-N-(3-(1-(8-(hydroxydimethylsilyl)-2-naphthoyl)piperidin-4-yl)benzyl)acetamide | 2,2,2-trifluoro-N-(3-(piperidin-4-yl)benzyl)acetamide, (1 eq.), EDCI (1.5 eq.) DMAP (1.5 eq.), DIEA (2 eq.) DCM (25 vol) R.T. 1 h; | Yield 84% Mol. Wt: 514.61 MS(ES+): m/z = 537.10[MH$^+$ + Na] |
| B-122 | tert-butyl 3-(1-(3-((hydroxydimethylsilyl)methyl)benzoyl)piperidin-4-yl)benzylcarbamate | 4-(3-aminomethyl phenyl) piperidine, (1.2 eq.), EDCI (1.5 eq.) DMAP (0.5 eq.), DCM R.T. 3 h; | Colorless oil, Yield 23.25%, Mol. Wt.: 482.69(monomer), 947.36 (dimer). MS (ES+): m/z = 482 [MH$^+$+ Na](monomer), 947.6 [MH$^+$](dimer) |
| B-129-spiro | tert-butyl ((1'-(3-(hydroxydimethylsilyl)benzoyl)-2H-spiro[benzofuran-3,4'-piperidin]-5-yl)methyl)carbamate | tert-butyl-((2H-spiro[benzofuran-3, 4'-piperidin]-5-yl) methyl) carbamate, (1. eq.), EDCI (1.5 eq.) DMAP (1.2 eq.), DCM R.T. 3 h | Yield 66% Mol. Wt:- 496.67 MS (ES+): m/z = 497.3 [MH$^+$] |

Step-5

Products of Step-7 were deprotected as per reaction conditions mentioned in the table below to get the silanols. In most of the cases, compounds were found to be mixture of monomer & dimer as per HPLC as well as NMR data. All reactions were done on 100-200 mg scale.

| Comp. No. | Structure | Brief Reaction conditions | Analytical data |
|---|---|---|---|
| 52-Spiro | (5-(aminomethyl)-2H-spiro[benzofuran-3,4'-piperidin]-1'-yl)(8-(hydroxydimethylsilyl)naphthalen-2-yl)methanone | trifluoro acetic acid (3 vol.). dichloromethane. Stirring at room temp for 3 hr. Conc. for removal of DCM, and purification by prep HPLC. TLC (10% Methanol in chloroform. | Yield 30%. Mol. Wt: 446.60 (monomer) 875.2(dimer) MS (ES+): m/z = 447.2 [MH$^+$] (monomer) 875.55 [MH$^+$](dimer) $^1$H NMR (400 MHz, DMSO-d$_6$): δ 8.23 (s, 1H), 8.06 (d, J = 9.1 Hz, 4H), 7.80 (d, J = 6.9 Hz, 1H), 7.57 (t, J = 7.6 Hz, 2H), 7.36 (s, 1H), 7.22 (d, J = 8.1 Hz, 1H), 6.84 (d, J = 8.4 Hz, 1H), 4.46 (d, J = 50.2 Hz, 3H), 3.93 (q, J = 6.7, 6.2 Hz, 2H), 3.06 (s, 4H), 1.73 (s, 4H), 0.47 (d, J = 25.1 Hz, 6H). |

| Comp. No. | Structure | Brief Reaction conditions | Analytical data |
|---|---|---|---|
| 52 | (4-(3-(aminomethyl)phenyl)piperidin-1-yl)(8-(hydroxydimethylsilyl)naphthalen-2-yl)methanone | THF: MeOH, KOH, at 50° C. for 6 h, concentration followed by extraction with ethyl acetate, and purification by prep HPLC. TLC (10% Methanol in chloroform. | Yield 10.4%. Mol. Wt: 418.60 (monomer) 819.20(dimer) MS (ES+): m/z = 419.15 [MH+] (monomer) 819.30 [MH+](dimer) ¹H NMR (400 MHz, CD₃CN, D₂O0): δ 8.30 (s, 1H), 8.01 (d, J = 8.4 Hz, 1H), 7.83 (d, J = 8 Hz, 1H), 7.54 (m, 3H), 7.38-7.18 (m, 4H), 4.00 (s, 2H), 2.92-2.64 (m, 5H), 1.97-1.40 (m, 4H), 0.47 (d, J = 25.1 Hz, 6H). |
| 122 | (4-(3-(aminomethyl)phenyl)piperidin-1-yl) (3-((hydroxydimethylsilyl)methyl)phenyl)methanone | trifluoro acetic acid (6 eq.). in dichloromethane. Stirring at room temp. for 12 hr. conc. for removal of DCM, and purification by prep HPLC. TLC (10% Methanol in chloroform. | Colorless oil; Yield: 36% Mol. Wt.: 382.57 (monomer), 747.13 (dimer), MS (ES+): m/z = 383.15 [MH+] (monomer), 747.45 [MH+] (dimer), HPLC Purity: 99%(monomer + dimer) ¹H NMR (400 MHz, DMSO-d₆): δ 7.36-7.23 (m, 4H), 7.13-6.99 (m, 4H), 3.97 (d, J = 4.6 Hz, 2H), 3.12 (s, 2H), 2.91-2.72 (m, 3H), 2.08 (s, 2H), 1.69 (d, J = 113.7 Hz, 4H), −0.04−−0.10 (m, 6H). |
| 129-Spiro | (5-(aminomethyl)-2H-spiro[benzofuran-3,4′-piperidin]-1′-yl)(3-(hydroxydimethylsilyl)phenyl)methanone | trifluoro acetic acid (2.5 vol.). in dichloromethane. Stirring at room temp. for 3 hr. conc. for removal of DCM, and purification by prep HPLC. TLC (10% Methanol in chloroform. | Yield 15%. Mol. Wt:- 396.55 (Monomer), 775.09(dimer) MS (ES+): m/z = 419.15 [MH+ + Na] Monomer] 775.40 [MH+] (dimer) ¹H NMR (400 MHz, DMSO-d₆, D₂O): δ 7.64-7.32 (m, 5H), 7.20 (d, J = 8.4 Hz, 1H), 6.81 (d, J = 8.3 Hz, 1H), 4.42 (d, J = 44.6 Hz, 2H), 3.92 (d, J = 5.9 Hz, 2H), 3.28-2.90 (m, 4H), 1.74 (m, 4H), 0.29 (d, J = 22.5 Hz, 6H) |

Approach-3

Step-1 & 2:—

Alkylation of Aryl hydroxyl carboxylates and subsequent hydrolysis of aryl esters with dimethyl (aryloxymethyl) silanols functionality was carried out as per conditions mentioned in the table below. Carboxylic acids obtained after hydrolysis in the form of mixture

| Comp. No. | Structure | Brief Reaction conditions | Analytical data |
|---|---|---|---|
| A1-137 | 4-((hydroxydimethylsilyl)methoxy)benzoic acid | 1) 4-hydroxy ethyl benzoate(1 eq), silane (eq), Potassium carbonate (eq), Acetone, 24 hrs reflux, Product separated by column chromatography over silica gel 2) THF, Water LiOH, Crude product used for next step after usual work-up (Concentration, Acidification by KHSO₄ & extraction with ethyl acetate) | Colorless oil Yield: 46.10%, HPLC: 95.35%, (mol. wt: 254) ¹H NMR (400 MHz, CDCl₃): δ 0.24(d, J = 12 Hz, 6H), 2.74(s, 3H), 3.60(s, 2H), 3.88(s, 3H), 6.96(d, J = 8.8 Hz, 2H), 7.98(d, J = 8.4 Hz, 2H). 2)yellow color solid Yield: 78.83%, ESMS: (mol. wt: 226) MS (ES+): m/z = 226.10 [MH+] ES+-, (ES−)-225.44 [MH−] |

| Comp. No. | Structure | Brief Reaction conditions | Analytical data |
|---|---|---|---|
| A1-138 | 3-((hydroxydimethylsilyl)methoxy)benzoic acid | 1) 3-hydroxy ethyl benzoate(1 eq), silane (eq), Potassium carbonate (eq), Acetone, 24 hrs reflux, Product separated by column chromatography over silica gel 2) THF, Water LiOH, Crude product used for next step after usual work-up (Concentration, Acidification by $KHSO_4$ & extraction with ethyl acetate) | 1) colorless solid Yield: 61.67%, HPLC: 99.25% $^1$H NMR (400 MHz, $CDCl_3$): δ 7.61 (d, J = 3.4 Hz, 1H), 7.33 (t, J = 8.0 Hz, 1H), 7.27-7.23 (m, 1H), 7.14 (d, J = 8.0 Hz, 1H), 3.92 (s, 3H), 3.59 (s, 3H), 0.23 (d, J = 11.5 Hz, 6H). 2) colorless solid Yield: ~48.03% MS (ES+): m/z = 226.19 [MH$^+$] ES$^+$-, (ES$^-$)-225.18 [MH$^-$] (mol. wt: 226) |

Step-3

| Comp. No. | Structure | Brief Reaction conditions | Analytical data |
|---|---|---|---|
| B1-137 | tert-butyl 3-(1-(4-((hydroxydimethylsilyl)methoxy)benzoyl)piperidin-4-yl)benzylcarbamate | Coupling of carboxylic acid with Boc-protected 4-(3-aminomethyl phenyl) piperidine, (1.1 eq.), EDCI (1.5 eq.) DMAP (0.5 eq.), DCM R.T. 12 h; | Yield: 63.58% HPLC: 54.55% LCMS: (Mol Wt-monomer-470.28, Dimer-938.5), MS (ES+): m/z = 979.50 [MH$^+$ + ACN] |
| B1-138 | tert-butyl 3-(1-(3-((hydroxydimethylsilyl)methoxy)benzoyl)piperidin-4-yl)benzylcarbamate | Coupling of carboxylic acid with Boc-protected 4-(3-aminomethyl phenyl) piperidine, (1.1 eq.), EDCI (1.5 eq.) DMAP (0.5 eq.), DCM R.T. 12 h; | Yield: 69.36% HPLC: 28.52% LCMS: (Mol Wt-monomer-470.28, Dimer-938.5), MS (ES+): m/z = 979.50 [MH$^+$ + ACN] |

Step-4

Products of Step-11 were deprotected as per reaction conditions mentioned in the table below to get the silanols.

In most of the cases, Compounds were found to be mixture of monomer & dimer as per HPLC as well as NMR data. All reactions were done on 100-200 mg scale.

| Comp. No. | Structure | Brief Reaction conditions | Analytical data |
|---|---|---|---|
| 137 | (4-(3-(aminomethyl)phenyl)piperidin-1-yl)(4-((hydroxydimethylsilyl)methoxy)phenyl)methanone | trifluoro acetic acid (3 eq.). In dichloromethane. Stirring at room temp. For 12 hr. conc. for removal of DCM, and purification by prep HPLC. TLC (10% Methanol in chloroform. | Yield: 5.79% HPLC Purity: 89.63%, LCMS: (dimer): (Mol. Wt.; 778) MS (ES+): m/z = 779 [MH$^+$] $^1$H NMR (400 MHz, DMSO-d$_6$): δ 8.15 (s, 3H), 7.41-7.18 (m, 6H), 6.99 (d, J = 8.5 Hz, 2H), 4.02 (q, J = 5.6 Hz, 2H), 3.65 (s, 2H), 3.12-2.78 (m, 5H), 1.86-1.50 (m, 4H), 0.22 (s, 6H). |
| 138 | (4-(3-(aminomethyl)phenyl)piperidin-1-yl)(3-((hydroxydimethylsilyl)methoxy)phenyl)methanone | trifluoro acetic acid (3 eq.). In dichloromethane. Stirring at room temp. For 12 hr. conc. for removal of DCM, and purification by prep HPLC. TLC (10% Methanol in chloroform. | Yield: 4.80% HPLC Purity: 85.35%, LCMS: (dimer): Mol. Wt.; 778, MS (ES+): m/z = 779 [MH$^+$] $^1$H NMR (400 MHz, DMSO-d$_6$): δ 8.11 (s, 3H), 7.40-7.25 (m, 4H), 6.98 (dt, J = 28.5, 5.4 Hz, 3H), 4.62 (s, 1H), 4.02 (q, J = 5.8 Hz, 2H), 3.63 (d, J = 8.8 Hz, 2H), 3.14 (d, 3 = 16.3 Hz, 4H), 2.95-2.75 (m, 1H), 1.73 (d, J = 87.2 Hz, 4H), 0.20 (d, J = 6.4 Hz, 6H) |

Example 5

Diisopropylsilanol Synthesis

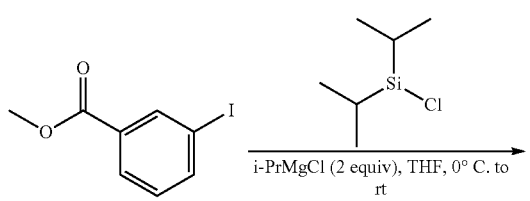

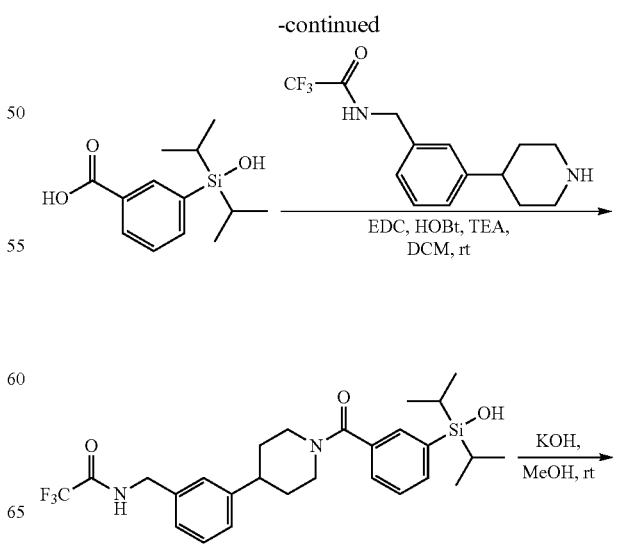

Synthesis of [4-[3-(aminomethyl)phenyl]-1-piperidyl]-[3-[hydroxy(diisopropyl)silyl]phenyl]methanone

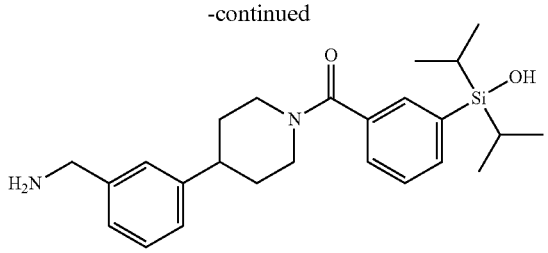

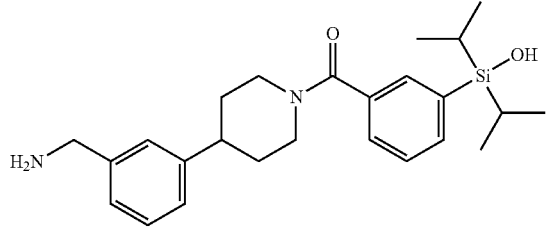 [SMILES: CC(C)[Si](O)(c1cccc(C(=O)N2CCC(c3cccc(CN)c3)CC2)c1)C(C)C]

A solution of 2,2,2-trifluoro-N-[[3-[1-[3-[hydroxy(diisopropyl)silyl]benzoyl]-4-piperidyl]phenyl]methyl]acetamide (0.014 g, 0.027 mmol) in MeOH (1 mL) was charged with 1M KOH (0.081 mL, 0.081 mmol) and stirred at rt for 16 h. The reaction mixture was partitioned between DCM and H₂O and separated. The aqueous was re-extracted with DCM (3×) and the combined organic fractions were dried over Na₂SO₄, filtered, and concentrated in vacuo resulting in a crude off-white foam solid. The crude was further purified by chromatography on silica gel [ISCO Combiflash, 4 g gold cartridge, eluting with 100% DCM→10% MeOH in DCM resulting in 1 mg of material.

Synthesis of 2,2,2-trifluoro-N-[[3-[1-[3-[hydroxy(diisopropyl)silyl]benzoyl]-4-piperidyl]phenyl]methyl]acetamide

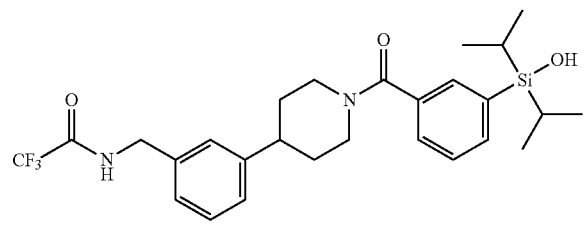 [SMILES: CC(C)[Si](O)(c1cccc(C(=O)N2CCC(c3cccc(CNC(=O)C(F)(F)F)c3)CC2)c1)C(C)C]

A solution of 3-[hydroxy(diisopropyl)silyl]benzoic acid (0.020 g, 0.0392 mmol), 2,2,2-trifluoro-N-[[3-(4-piperidyl)phenyl]methyl] acetamide (0.027 g, 0.0950 mmol), TEA (0.017 mL, 0.119 mmol) in DCM (1 mL) was charged with EDC (0.018 g, 0.0950 mmol) and HOBt (0.013 g, 0.0950 mmol) and stirred at rt under N₂ gas for 4 hr. The reaction mixture was partitioned between DCM and H₂O and separated. The aqueous was re-extracted with DCM (3×) and the combined organic fractions were washed with sat. NaHCO3 (1×), 10% HCl (1×), brine (1×), dried over Na₂SO₄, filtered, and concentrated in vacuo resulting in a crude oil which was purified by chromatography on silica gel [ISCO Combiflash, 4 g gold cartridge, eluting with 100% DCM→5% MeOH in DCM] resulting in 14 mg, 34% yield of the title compound as an off-white solid. ¹H NMR (300 MHz, CDCl₃): δ=7.57-7.63 (m, 2H), 7.38-7.48 (m, 2H), 7.33 (t, J=8.1 Hz, 1H), 7.13-7.21 (m, 3H), 6.86 (br.s., 1H), 4.85 (br. s., 1H), 4.50 (d, J=5.7 Hz, 2H), 3.85 (br. s., 1H), 2.71-3.20 (m, 2H), 1.50-2.05 (m, 6H), 1.13-1.30 (m, 2H), 1.04 (d, J=7.2 Hz, 6H), 0.954 (d, J=7.2 Hz, 6H).

Synthesis of 3-[hydroxy(diisopropyl)silyl]benzoic acid

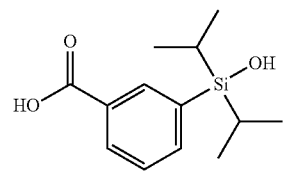 [SMILES: CC(C)[Si](O)(c1cccc(C(=O)O)c1)C(C)C]

A solution of methyl 3-diisopropylsilylbenzoate (25 mg, 0.099 mmol) in MeOH (500 μL) was charged with 1M NaOH (100 mL, 0.099 mmol) and stirred at rt for 16 hr. The reaction mixture was concentrated in vacuo to remove the MeOH and partitioned between pet. ether and H₂O and separated. The aqueous was acidified with 10% HCl and extracted with EtOAc (3×). The combined organic fractions were dried over Na₂SO₄, filtered and concentrated in vacuo resulting in 21 mg, 88% yield of the title compound as an off-white solid. ¹H NMR (300 MHz, CDCl₃): δ=8.32 (bs, 1H), 8.13 (dt, J=8.1, 1.5 Hz, 1H), 7.81 (dt, J=7.2, 1.5 Hz, 1H), 7.49 (t, J=8.1 Hz, 1H), 1.18-1.34 (m, 2H), 1.07 (d, J=7.5 Hz, 6H), 0.98 (d, J=7.5 Hz, 6H). MS (ES-): m/z 251.03 (100) [MH⁻].

Synthesis of methyl 3-diisopropylsilylbenzoate

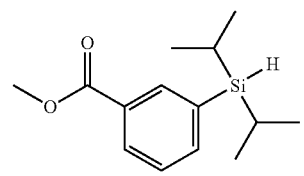 [SMILES: COC(=O)c1cccc([SiH](C(C)C)C(C)C)c1]

A solution of methyl-3-iodo benzoate (1.0 g, 3.82 mmol) in anhy. THF (20 mL) was cooled to 5° C. and dropwise charged with iPrMgCl (2M in THF) (3.82 mL, 7.63 mmol) and stirred at 5° C. for an additional 3 hr. The reaction mixture was charged with chlorodiisopropylsilane (3.26 mL, 19.1 mmol) and allowed to warm to rt and stirred at this temperature for an additional 16 hr. The reaction mixture was partitioned between EtOAc and sat. NaHCO₃ and separated. The aqueous was re-extracted with EtOAc (3×) and the combined organic fractions were dried over Na₂SO₄, filtered, and concentrated in vacuo resulting in a crude oil. The crude was further purified by chromatography on silica gel [ISCO Combiflash, 4 g gold cartridge, eluting with 100% pet. ether→30% EtOAc in pet ether] resulting in 100 mg, 10% yield of the title compound as a clear colorless oil. ¹H NMR (300 MHz, CDCl₃): δ=8.18 (bs, 1H), 8.04 (dt, J=8.1, 1.5 Hz, 1H), 7.70 (dt, J=7.2, 1.5 Hz, 1H), 7.43 (t, J=7.2 Hz, 1H), 3.99 (t, J=3.3 Hz, 1H), 3.92 (s, 3H), 1.18-1.34 (m, 2H), 1.07 (d, J=7.5 Hz, 6H), 0.98 (d, J=7.5 Hz, 6H). MS (ES+): m/z 250.99 (100) [MH+].

Example 6

Synthesis of Tryptase Inhibitors with Silanols Functionality

Seventeen Final targets with Silanol functionality were synthesized. These compounds were synthesized by three different approaches as given below.

Approach-1:—

Desired halo aryl carboxylic acids were first coupled with protected 4-(3-Aminomethyl phenyl) piperidine or 5-Aminomethyl Spiro [benzofuran-3, 4'-piperidine]. Coupled product was reacted with 1,2-diethoxy-1,1,2,2-tetramethyl-disilane to get ethoxydimethyl(Aryl)silanes, which upon treatment with acetic acid and subsequent deprotection afforded in the title compounds. 11 compounds were synthesized from Approach-1.

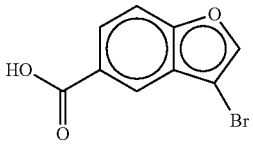

3-bromobenzofuran-5-carboxylic acid
A1-148
1) US2003/232853; (2003)
2) *J. Med. Chem*, 38; (1995); 3094-3105
3) US2011/82098

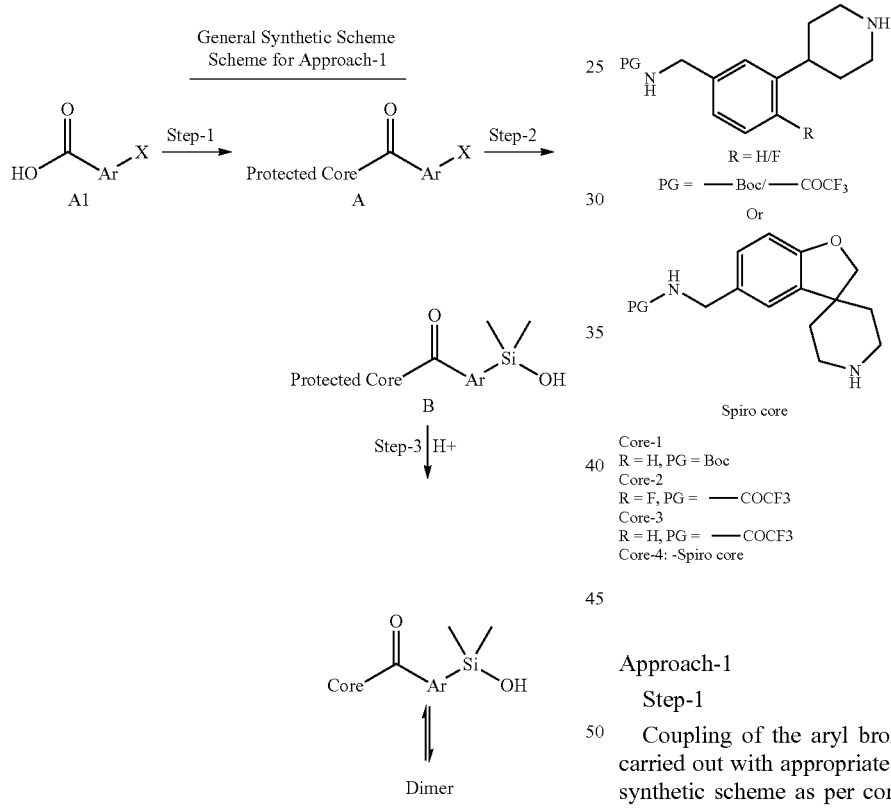

General Synthetic Scheme
Scheme for Approach-1

X = Br/I
Protected Cores

R = H/F
PG = —Boc/ —COCF₃

Or

Spiro core

Core-1
R = H, PG = Boc
Core-2
R = F, PG = —COCF₃
Core-3
R = H, PG = —COCF₃
Core-4: -Spiro core

Approach-1

Step-1

Coupling of the aryl bromo carboxylic acids (A1) was carried out with appropriate protected core as shown in the synthetic scheme as per conditions mentioned in the table below.

| 1. | 148 Spiro | 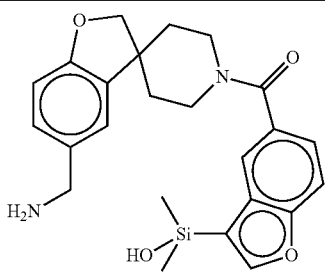 | 4 Apr. 2012 |

| | | | |
|---|---|---|---|
| A-148Spiro | 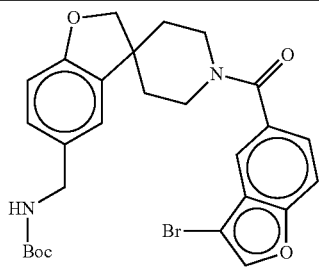<br>tert-butyl ((1'-(3-bromobenzofuran-5-carbonyl)-2H-spiro[benzofuran-3,4'-piperidin]-5-yl)methyl)carbamate | tert-butyl((2H-spiro[benzofuran-3,4'-piperidin]-5-yl)methyl)carbamate, (1 eq.), EDCI (1.5 eq.) DMAP (1.2 eq.), DCM (25 vol) R.T. 15 h; | Yield: ~97%<br>Mol. Wt.: 541.43<br>MS (ES+): m/z = 541, 543 [MH+] |

Step-2

Stirred suspension of coupled products from step-1 in N-methyl pyrrolidine was degassed with argon and palladium chloride, di-isopropyl ethyl amine, and 1,2-diethoxy-1,1,2,2, tetra methyl silane were added to it. Reaction mixture was heated to ~60° C. and reaction monitored by LCMS until most of the starting material was consumed. There after acetonitrile, 1N aq. acetic acid and 2-(dimethyl amino) ethane thiol hydrochloride was added and reaction mixture stirred for 2 hr at room temperature. Reaction mixture was diluted with water, filtered through celite, extracted with ethyl acetate and the combined ethyl acetate extracts were dried over sodium sulfate, filtered, and concentrated in vacuo to get the crude products which were sufficiently pure to be used for deprotection.

The details of the compounds are given below.

| | | | |
|---|---|---|---|
| B-148 Spiro | 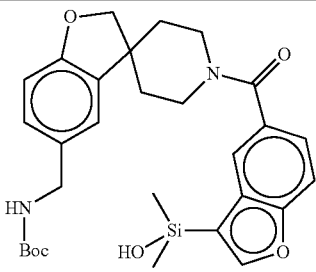<br>tert-butyl ((1'-(3-(hydroxydimethylsilyl)benzofuran-5-carbonyl)-2H-spiro[benzofuran-3,4'-piperidin]-5-yl)methyl)carbamate | 1,2-diethoxy-1,1-2,2-tetramethyl silane(3 eq.) PdCl$_2$ (0.1 eq), DTBPBP (0.2 eq), DIPEA (6 eq), NMP, 50° C., 14 hrs. | Yield 35%.<br>Mol. Wt: 536.69,<br>MS (ES+): m/z = 558.9 [MH+ + Na] |

Step-3

Products of Step-2 were deprotected as per reaction conditions mentioned in the table below to get the silanols. In most of the cases, Compounds were found to be mixture of monomer &dimer as per HPLC as well as NMR data. All reactions were done on 100-200 mg scale.

| | | | |
|---|---|---|---|
| 148 Spiro | 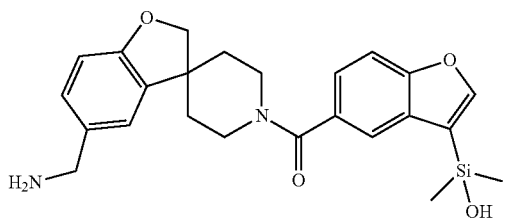<br>(5-(aminomethyl)-2H-spiro[benzofuran-3,4'-piperidin]-1'-yl)(3-(hydroxydimethylsilyl)benzofuran-5-yl)methanone | trifluoroacetic acid (2.5, vol) DCM (50 vol), RT, 1 h. | Yield 10%.<br>Mol. Wt: 436.58(Monomer) 855.14(Dimer)<br>MS (ES+): m/z = 499.70 [MH+ + Na + AcN] (monomer) 854.80[MH+] (dimer)<br>$^1$H NMR (400 MHz, DMSO-d$_6$, D$_2$O): δ 8.01(br.s., 4H), 7.68 (d, J = 8.8 Hz, 1H), 7.63(s, 1H), 7.39-7.37(m, 2H), 7.23(d, J = 8.00 Hz, 1H), 6.84(d, J = 8.00 Hz, 1H), 4.49(s, 2H), 3.94(s, 2H), 3.13(br.s., 3H), 1.38-1.92(m, 5H), .0.42(s, 6H). |

Example 7

The following table (Table 10) contains exemplary compounds. One of ordinary skill in the art will recognize that these compounds may be used to form homodimic or heterodimeric compounds.

TABLE 10

Exemplary Silyl Monomers Targeted to Tryptase.

| Sr. No. | Cmpd. Structure | Cmpd. Code |
|---|---|---|
| 1 | | T130 |
| 2 | | T46-vinyl |
| 3 | | T48-vinyl |
| 4 | | T50 |

TABLE 10-continued

Exemplary Silyl Monomers Targeted to Tryptase.

| Sr. No. | Cmpd. Structure | Cmpd. Code |
|---|---|---|
| 5 | | T51 |
| 6 | | T52 |
| 7 | | T121 |
| 8 | | T122 |
| 9 | | T93 |
| 10 | | T94 |

TABLE 10-continued

Exemplary Silyl Monomers Targeted to Tryptase.

| Sr. No. | Cmpd. Structure | Cmpd. Code |
|---|---|---|
| 11 | | T129 |
| 12 | | T62 silyl |
| 13 | | T116 silyl |
| 14 | | T120 |
| 15 | | T128 |
| 16 | | T148 |

TABLE 10-continued
Exemplary Silyl Monomers Targeted to Tryptase.
| Sr. No. | Cmpd. Structure | Cmpd. Code |
|---|---|---|
| 17 | 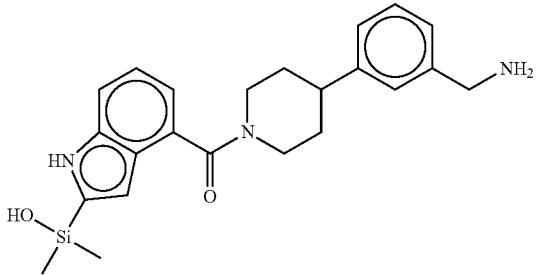 | |
| 18 | 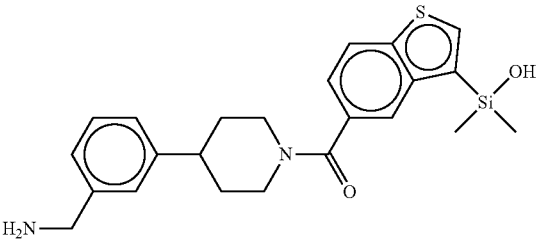 | T149 |
| 19 | 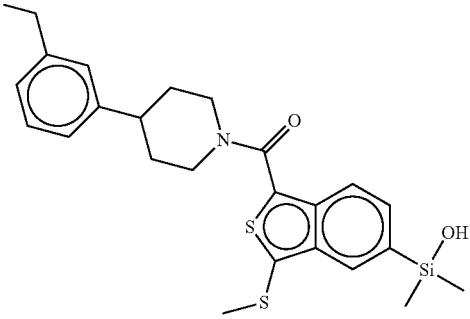 | |
| 20 | 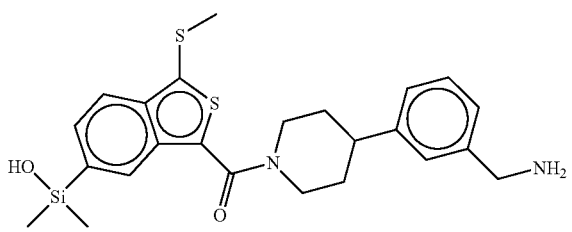 | |
| 21 | 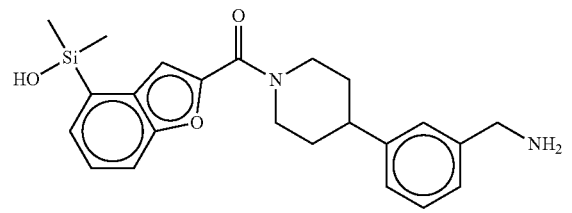 | |

135 136
TABLE 10-continued
Exemplary Silyl Monomers Targeted to Tryptase.
| Sr. No. | Cmpd. Structure | Cmpd. Code |
|---|---|---|
| 22 | 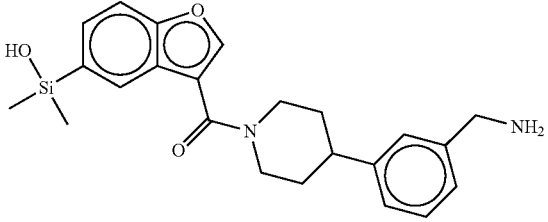 | |
| 23 | 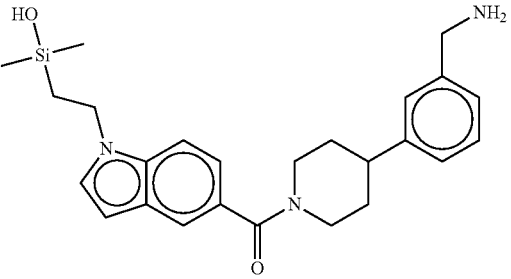 | |
| 24 | 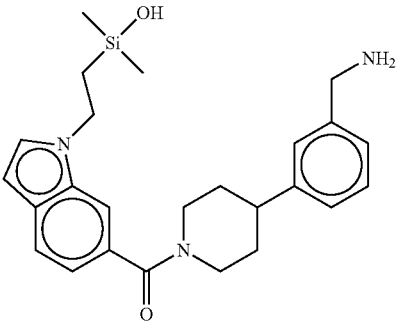 | |
| 25 | 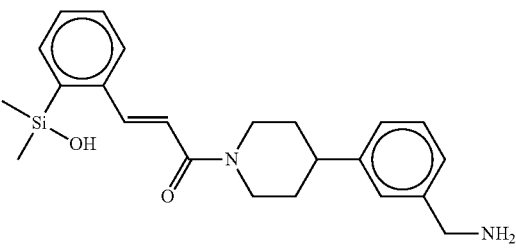 | |
| 26 | 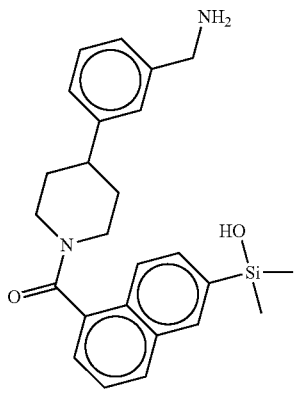 | |

TABLE 10-continued
Exemplary Silyl Monomers Targeted to Tryptase.
| Sr. No. | Cmpd. Structure | Cmpd. Code |
|---|---|---|
| 27 | 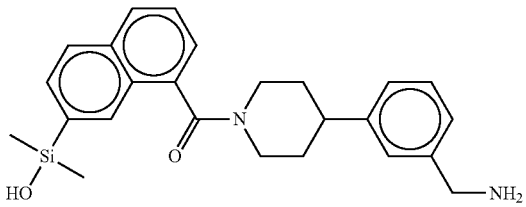 | T11Silyl |
| 28 | 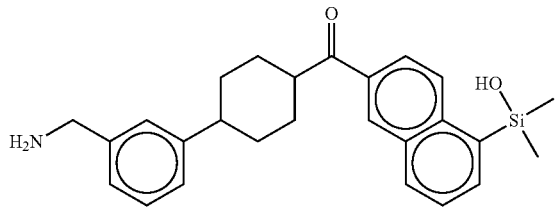 | |
| 29 | 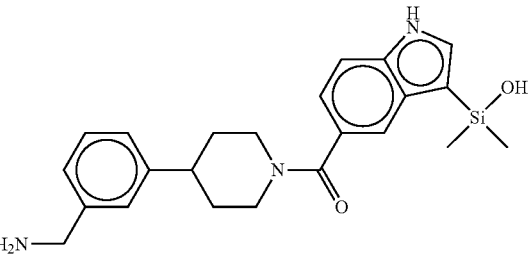 | |
| 30 | 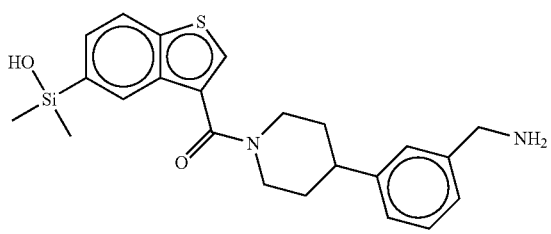 | |
| 31 | 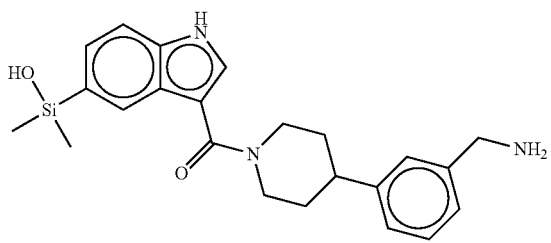 | |
| 32 | 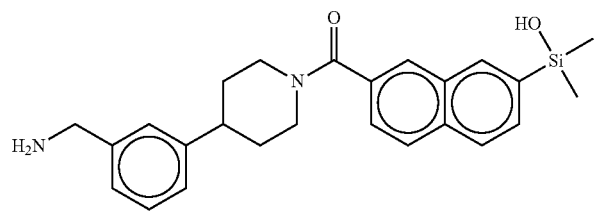 | |

TABLE 10-continued
Exemplary Silyl Monomers Targeted to Tryptase.
| Sr. No. | Cmpd. Structure | Cmpd. Code |
|---|---|---|
| 33 | 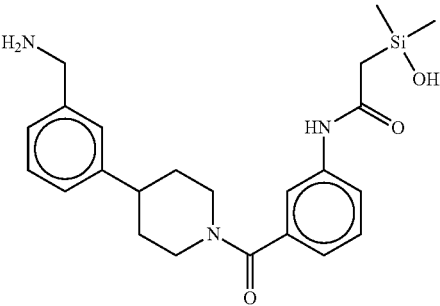 | |
| 34 | 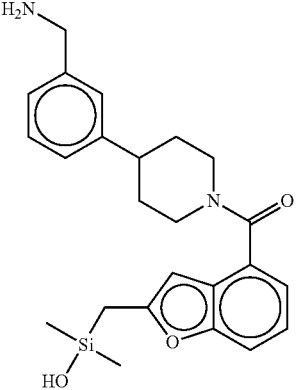 | |
| 35 | 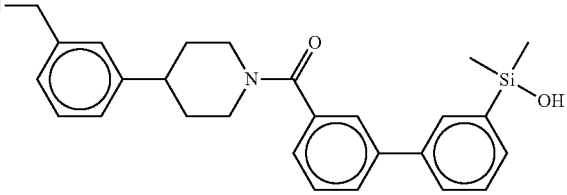 | T35Silyl |
| 36 | 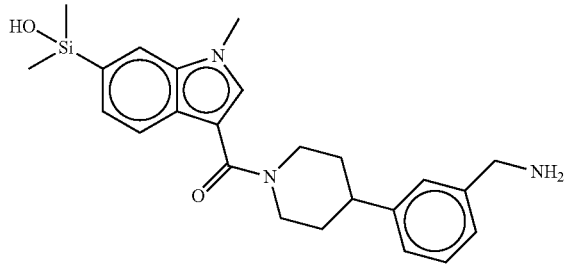 | T152NMethyl |
| 37 | 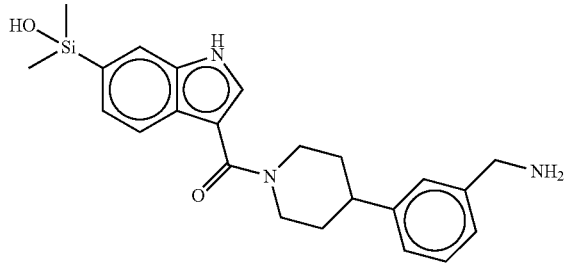 | T152 |

TABLE 10-continued
Exemplary Silyl Monomers Targeted to Tryptase.
| Sr. No. | Cmpd. Structure | Cmpd. Code |
|---|---|---|
| 38 | 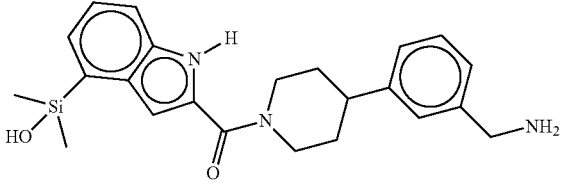 | T32Silyl |
| 39 | 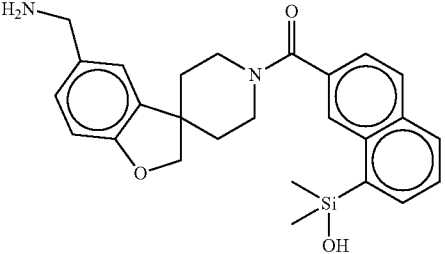 | T52Spiro |
| 40 | 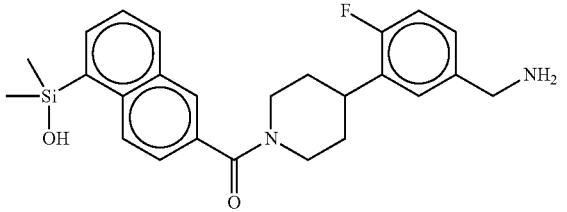 | T120F |
| 41 | 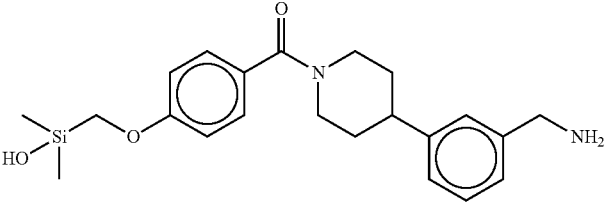 | T137 |
| 42 | 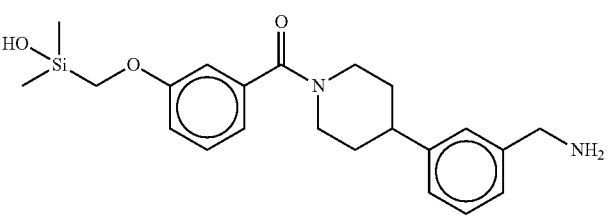 | T138 |
| 43 | 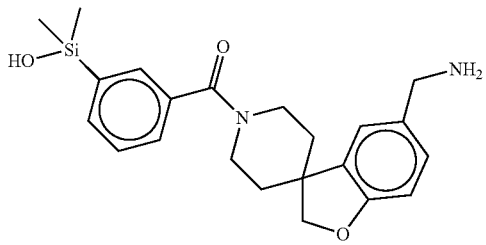 | T129Spiro |

TABLE 10-continued

Exemplary Silyl Monomers Targeted to Tryptase.

| Sr. No. | Cmpd. Structure | Cmpd. Code |
|---|---|---|
| 44 | | T129Smethyl |
| 45 | | T148-spiro |
| 46 | | T52-spiro |
| 47 | | T129-spiro |
| 48 | | |

TABLE 10-continued

Exemplary Silyl Monomers Targeted to Tryptase.

| Sr. No. | Cmpd. Structure | Cmpd. Code |
|---|---|---|
| 49 | | |
| 50 | | |
| 51 | | |

TABLE 10-continued

Exemplary Silyl Monomers Targeted to Tryptase.

| Sr. No. | Cmpd. Structure | Cmpd. Code |
|---|---|---|
| 52 | | |
| 53 | | |
| 54 | | |

TABLE 10-continued

Exemplary Silyl Monomers Targeted to Tryptase.

| Sr. No. | Cmpd. Structure | Cmpd. Code |
|---|---|---|
| 55 | |

TABLE 10-continued

Exemplary Silyl Monomers Targeted to Tryptase.

| Sr. No. | Cmpd. Structure | Cmpd. Code |
|---|---|---|
| 58 | | |
| 59 | | |
| 60 | | |
| 61 | | |
| 62 | | |

TABLE 10-continued

Exemplary Silyl Monomers Targeted to Tryptase.

| Sr. No. | Cmpd. Structure | Cmpd. Code |
|---|---|---|
| 63 | | |
| 64 | | |
| 65 | | |

TABLE 10-continued

Exemplary Silyl Monomers Targeted to Tryptase.

| Sr. No. | Cmpd. Structure | Cmpd. Code |
|---|---|---|
| 66 | | |
| 67 | | |
| 68 | | |
| 69 | | |

TABLE 10-continued

Exemplary Silyl Monomers Targeted to Tryptase.

| Sr. No. | Cmpd. Structure | Cmpd. Code |
|---|---|---|
| 70 | 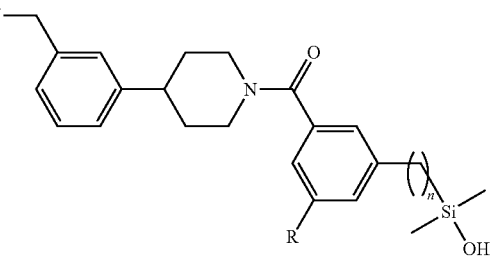 R = -alkyl-aryl, -alkyl-heteroaryl, -alkenyl-aryl, -alkenyl-heteroaryl, -alkynyl-aryl, -alkynyl-heteroaryl, phenyl, or heteroaryl; wherein phenyl and heteroaryl can be optionally substituted by halogen, —CN, —OR, —SR, phenyl, or heteroaryl where phenyl or heteroaryl can be optionally substituted by halogen, cyano, hydroxyl. | |
| 71 | 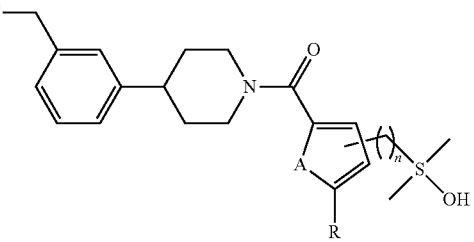 wherein A = O or S, n = 0 or 1; R = -alkyl-aryl, -alkyl-heteroaryl, -alkenyl-aryl, -alkenyl-heteroaryl, -alkynyl-aryl, -alkynyl-heteroaryl, phenyl, heteroaryl, where phenyl and heteroaryl can be optionally substituted by halogen, —CN, —OR, —SR, phenyl, or heteroaryl where phenyl or heteroaryl can be optionally substituted by halogen, cyano, hydroxyl. | |
| 72 | 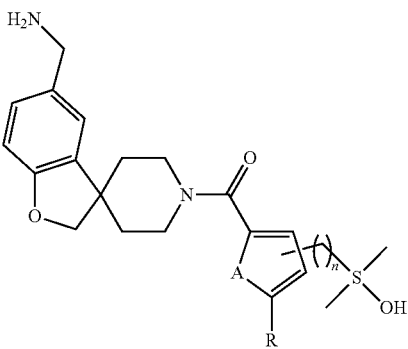 wherein A = O or S, n = 0 or 1; R = -alkyl-aryl, -alkyl-heteroaryl, -alkenyl-aryl, -alkenyl-heteroaryl, -alkynyl-aryl, -alkynyl-heteroaryl, phenyl, heteroaryl, where phenyl and heteroaryl can be optionally substituted by halogen, —CN, —OR, —SR, phenyl, or heteroaryl where phenyl or heteroaryl can be optionally substituted by halogen, cyano, hydroxyl. | |

TABLE 10-continued
Exemplary Silyl Monomers Targeted to Tryptase.
| Sr. No. | Cmpd. Structure | Cmpd. Code |
|---|---|---|
| 73 | 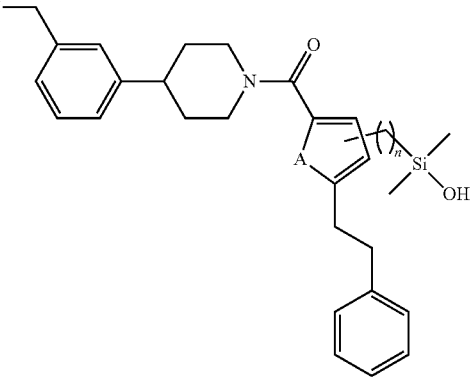
where n = 0 or 1; where A = S or O | |
| 74 | 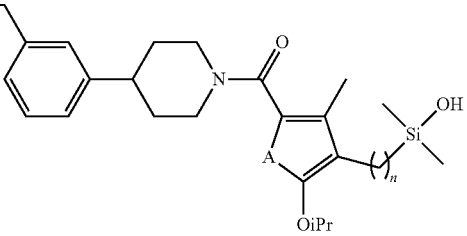
where n = 0 or 1; where A = S or O | |
| 75 | 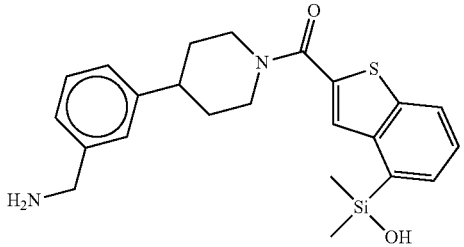 | |
| 76 | 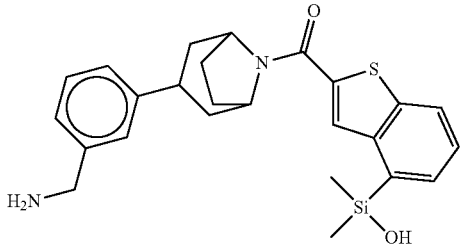 | |
| 77 | 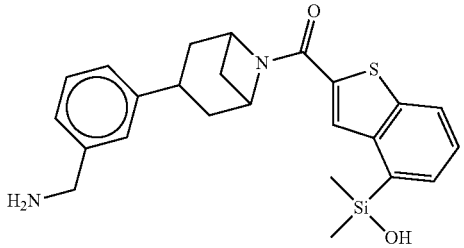 | |

Example 8

The following table (Table 11) contains exemplary compounds that target to the ribosome. In some embodiments, these compounds form heterodimeric compounds.

TABLE 11

Exemplary Silyl Monomers Targeted to the Ribosome.

| Sr. No. | Cmpd. Structure | Cmpd. Code |
|---|---|---|
| 1 | | |
| 2 | | |
| 3 | | |
| 4 | | AzSi-1 |

TABLE 11-continued

Exemplary Silyl Monomers Targeted to the Ribosome.

| Sr. No. | Cmpd. Structure | Cmpd. Code |
|---|---|---|
| 5 | | Cl—Ph—Si-meta |
| 6 | | LZN-Si-3 |
| 7 | | FFL-Si-3 |

Example 9

The following table (Table 12) contains exemplary ligand moieties (i.e., $X^1$, $X^2$, or $X^3$, and the like), where

indicates the attachment point to a connector moiety (i.e., $Y^1$, $Y^2$, or $Y^3$, and the like) or a silyl moiety (i.e., $Z^1$, $Z^2$, or $Z^3$, and the like) if the connector moiety is absent.

TABLE 12

| | Exemplary Ligand Moieties Targeted to Tryptase |
|---|---|
| 1 | |
| 2 | |
| 3 | |
| 4 | |

TABLE 12-continued

Exemplary Ligand Moieties Targeted to Tryptase

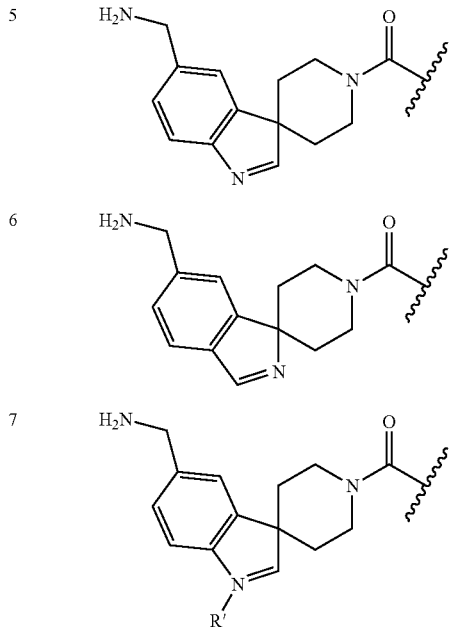

where R' is hydrogen, substituted or unsubstituted aliphatic, and substituted or unsubstituted heteroaliphatic

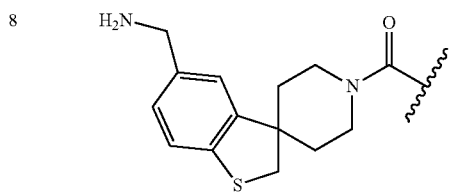

TABLE 12-continued

Exemplary Ligand Moieties Targeted to Tryptase

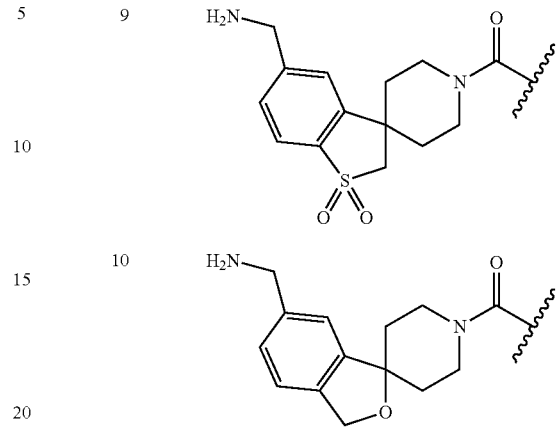

EQUIVALENTS

While specific embodiments have been discussed, the above specification is illustrative and not restrictive. Many variations will become apparent to those skilled in the art upon review of this specification. The full scope of the embodiments should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A dimer compound represented by:

$X^1$—$Y^1$—$Z^{1*}$—O—$Z^{2*}$—$Y^2$—$X^2$ (Formula III) or a pharmaceutically acceptable salt or stereoisomer thereof, wherein $X^1$ is a pharmacophore;

$Y^1$ is selected from the group consisting of:
  (a) a covalent bond;
  (b) a bivalent linker selected from the group consisting of: (i) substituted or unsubstituted $C_1$-$C_{10}$ alkylene, substituted or unsubstituted cycloalkylene, substituted or unsubstituted arylene, substituted or unsubstituted heteroarylene, acylene, sulfonyl, sulfonamide, phosphate, ester, carbonate, carbamate, or amide; and (ii) bivalent $C_{1-10}$ saturated or unsaturated, straight or branched, hydrocarbon chain, wherein one, two, three, or four methylene units of bivalent $C_{1-10}$ are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, phenylene, or a mono or bicyclic heterocyclene ring, wherein R is selected from the group consisting of hydrogen, aliphatic, heteroaliphatic, aryl, heteroaryl, arylalkyl, and heteroarylalkyl; and
  (c) a pharmaceutically acceptable polymer;

$X^2$ is a pharmacophore;

$Y^2$ is selected from the group consisting of:
  (a) a covalent bond;
  (b) a bivalent linker selected from the group consisting of: (i) substituted or unsubstituted $C_1$-$C_{10}$ alkylene, substituted or unsubstituted cycloalkylene, substituted or unsubstituted arylene, substituted or unsubstituted heteroarylene, acylene, sulfonyl, sulfonamide, phosphate, ester, carbonate, carbamate, or amide; and (ii) bivalent $C_{1-10}$ saturated or unsaturated, straight or branched, hydrocarbon chain, wherein one, two, three, or four methylene units of bivalent $C_{1-10}$ are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, phenylene, or a mono or bicyclic heterocyclene ring, wherein R is selected from the group consisting of hydrogen, aliphatic, heteroaliphatic, aryl, heteroaryl, arylalkyl, and heteroarylalkyl; and
  (c) a pharmaceutically acceptable polymer; and $Z^{1*}$ and $Z^{2*}$, independently, for each occurrence, are:

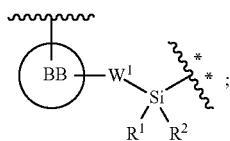

wherein

represents an attachment point to Y if Y is not a covalent bond, or to X if Y is a covalent bond;

represents an attachment point to O;

BB, independently for each occurrence, is a one- or two-ringed aryl or heteroaryl moiety, wherein the aryl or heteroaryl moiety is optionally substituted with one, two, three or more groups represented by $R^{BB}$; wherein:
each $R^{BB}$ is independently selected, for each occurrence, from the group consisting of hydrogen, halogen, hydroxyl, amino, thiol, S—CH$_3$, —COOH, —CONHR', substituted or unsubstituted aliphatic, substituted or unsubstituted heteroaliphatic, —C$_{1-4}$ alkyl, —O—C$_{1-4}$ alkyl, —N(R$^a$)—C$_{1-4}$alkyl, —C(O)C$_{1-4}$alkyl, —C(O)—O—C$_{1-4}$alkyl, and —C(O)—NR$^a$R$^b$; wherein:
R' is independently selected, for each occurrence, from the group consisting of hydrogen, substituted or unsubstituted aliphatic, and substituted or unsubstituted heteroaliphatic; and
R$^a$ and R$^b$ are independently selected, for each occurrence, from the group consisting of hydrogen and C$_{1-4}$alkyl;
W$^1$, independently for each occurrence, is absent or selected from the group consisting of —C$_{1-4}$alkylene, —C$_{2-6}$alkenylene-, and —O—C$_{1-4}$alkylene-; and
R$^1$ and R$^2$ are independently for each occurrence, C$_{1-6}$ alkyl.

2. The dimer compound of claim 1, wherein X$^1$ and X$^2$ are different.

3. The dimer compound of claim 1, wherein W$^1$ is absent.

4. The dimer compound of claim 1, wherein BB is phenyl or heteroaryl.

5. The dimer compound of claim 1 wherein R$^1$ and R$^2$ are methyl.

6. The dimer compound of claim 1, wherein the dimer binds to a target biomolecule with greater affinity than does its corresponding monomers; the dimer is capable of interacting with a larger target site than its corresponding monomers are capable of interacting with; the target comprises two protein domains separated by a distance such that the dimer, but not its corresponding monomers, is capable of binding to both domains essentially simultaneously; the apparent IC$_{50}$ of the dimer is lower than the apparent IC$_{50}$ of its corresponding monomers; the ratio of the smaller of the apparent IC$_{50}$ of each corresponding monomer to the apparent IC$_{50}$ of the dimer is at least 3.0; the dimer has different fluorescent properties than its corresponding monomers; the dimer has greater fluorescent brightness at a particular wavelength than its corresponding monomers; the dimer's peak fluorescence is red- or blue-shifted relative to that of its corresponding monomers; the dimer has stronger inhibition than X$^1$ alone, X$^2$ alone, and/or its corresponding monomers alone; the dimer has greater activation than X$^1$ alone, X$^2$ alone, and/or its corresponding monomers alone; and/or the dimer creates a binding entity covering a larger surface area of a target than the surface area covered by X$^1$ alone, X$^2$ alone, and/or its corresponding monomers alone.

7. A method of treating a disease associated with a target protein or a target protein-protein interaction in a patient in need thereof comprising:
administering to said patient the dimer compound of claim 1,
wherein upon administration, the dimer compound binds to one, two, three or more protein domains in said target protein, or to at least one protein domain in each of the proteins involved in the protein-protein interaction.

8. A method of modulating two or more target biomolecule domains substantially simultaneously comprising:
contacting said biomolecular target with the dimer compound of claim 1, wherein X$^1$ is a first ligand moiety capable of binding to and modulating a first target biomolecule domain; and
X$^2$ is a ligand moiety capable of binding to and modulating a second target biomolecule domain.

9. A method of treating a disease associated with two or more target biomolecule domains in a patient in need thereof comprising: administering to said patient the dimer compound of claim 1, wherein
X$^1$ is a first ligand moiety capable of binding to and modulating a first target biomolecule domain; and
X$^2$ is a second ligand moiety capable of binding to and modulating a second target biomolecule domain.

10. The dimer compound of claim 1, wherein $Z^{1*}$ and $Z^{2*}$, independently for each occurrence, are:

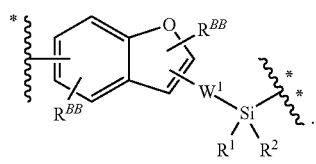

11. The dimer compound of claim 1, represented by:

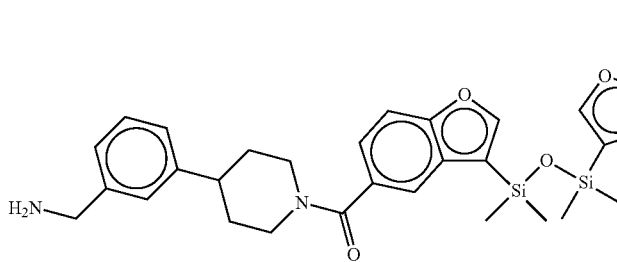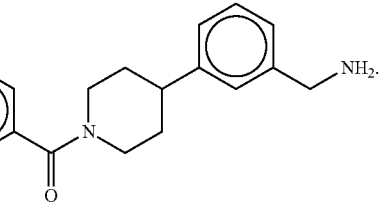

12. The dimer compound of claim 1, wherein $X^1$—$Y^1$—$Z^{1*}$— and $X^2$—$Y^2$—$Z^{2*}$— are different.

13. The dimer compound of claim 1, wherein $X^1$—$Y^1$—$Z^{1*}$— and $X^2$—$Y^2$—$Z^{2*}$— are the same.

14. The dimer compound of claim 1, wherein $Z^{1*}$ and $Z^{2*}$ are the same.

15. The dimer compound of claim 1, wherein $W^1$, independently for each occurrence, is absent or —$C_{1-4}$alkylene-.

16. The dimer compound of claim 1, wherein each $R^{BB}$ is independently selected, for each occurrence, from the group consisting of hydrogen, halogen, hydroxyl, amino, thiol, —COOH, —CONHR', substituted or unsubstituted aliphatic, substituted or unsubstituted heteroaliphatic, —$C_{1-4}$alkyl, —O—$C_{1-4}$alkyl, —N($R^a$)—$C_{1-4}$alkyl, —C(O)$C_{1-4}$alkyl, —C(O)—O—$C_{1-4}$alkyl, and —C(O)—N$R^aR^b$; wherein:
  R' is independently selected, for each occurrence, from the group consisting of hydrogen, substituted or unsubstituted aliphatic, and substituted or unsubstituted heteroaliphatic; and
  $R^a$ and $R^b$ are independently selected, for each occurrence, from the group consisting of hydrogen and $C_{1-4}$ alkyl.

17. The dimer compound of claim 1, wherein $X^1$ and $X^2$ are each, independently, selected from the group consisting of tryptase inhibitors, ribosome inhibitors, antibiotics, (2S, 4R)-4-methylglutamic acid, (VPPPVPPRRR (SEQ ID NO: 9))2K, 1,25 dihydroxy vitamin D, 17-beta-estradiol, 19S, 2',3'-Dideoxyadenosine, 2',5'-Dideoxyadenosine, 2-phenyl indole, A-371191, ABT-737, ABT-751, Acetylcholine, acidic phospholipids, aconitine, Ac-SpYVNVQ-NH2 (SEQ ID NO: 10), adalimumab, aeroplysinin-1, AG18, AG82, AG99, AG112, AG126, AG213, AG490, AG494, AG527, AG555, AG556, AG014699, ALB109564, albuterol, amphiregulin, anti-EGFR antibody C225, apigenin, ATM, ATPA, ATR, atropine, axitinib, AZD2281, BAD, basiliximab, BAY 50-4798, BAY K 8644, benomyl, betacellulin, bevacizumab, BH3I-1, BI-78D3, Bortezomib, BRCT, brompheniramine, BS-201, BS-401, butoxamine, caffeine, CAK, calyculin A, Caproctamine, CARD, caspase, Cdc37, Celastrol, Cetirizine, CGP 28392, Chk1, Chk2, Chlorotrianisene, chlorpheniramine, Cholera toxin, CNQX, curcumin, cyclin A, cyclin E, D24851, D64131, daclizumab, DD, Desloratadine, diacylglycerol, Dienestrol, Diethylstilbestrol, dihydropyridine, diphenhydramine, di-ubiquitin, domoic acid, doxylamine, Epidermal Growth Factor, epinephrine, epiregulin, ERK1-2, estradiol, estramustine, Estriol, estrone, etanercept, everolimus, farnesylthiosalicylic acid, Fexofenadine, FJ9, fluorouracil, Fmoc-Glu-Tyr-Aib-Asn-NH2 (SEQ ID NO: 5), forskolin, Fosfestrol, FtsZ, fumonisin B, G proteins, Galantamine, Glutamate, Granzyme B, GS7904L, H-GYGRKKRRQRRR-G-MPKKKPTPIQLNP-NH2 (SEQ ID NO: 2), Histamine, HL198, HPV E1, ICI 164,384, IGFII, IL2R, indandiones, infliximab, INO-1001, interferon, iodowillardiine, IP3, ipratropium, JNK, kainic acid, Keoxifene, KLVFF (SEQ ID NO: 3), K-ras, LBH589, lincosamides, Linezolid, Loratadine, LSNPTX-NH2 (SEQ ID NO: 7), LVFFA (SEQ ID NO: 4), LY290181, LY293558, LY294486, LY339434, LYASSNPAX-NH2 (SEQ ID NO: 8), MDL-12330A, MDM2, MEK, Memoquin, Mepitiostane, Meriolin, Metrifonate, MI-63, MI-219, MIRA-1, m114, m115, m116, mLST8/GβL, mono-ubiquitin, Naphthamides, Neostigmine, neuregulins, nifedipine, NKY80, nodularin, nolatrexed, norepinephrine, NSC 348900, NSC668036, Nutlins, P1-30, p38 MAPK, p53, pazopanib, PB1, PD98059, PD153035, PDZ, pemetrexed, Peptidimer-c, perifosine, phorbol esters, Phosphatidylinositol, Phosphatidylinositol 3-phosphate, Phosphatidylinositol 4-phosphate, Phosphatidylinositol 5-phosphate, Phosphatidylinositol (3,4)-biphosphate, Phosphatidylinositol (3,5)-biphosphate, Phosphatidylinositol (4,5)-biphosphate, Phosphatidylinositol (1,4,5)-triphosphate, Phosphatidylinositol (3,4,5)-triphosphate, Physostigmine, Pifithrin-a, Pilocarpine, PLX4720, podophyllotoxin, PPXXF motifs, PQIP, PRIMA-1, propranolol, PyD, pyrilamine, R18, raltitrexed, Ranibizumab, Rapamycin, Raptor, RITA, salbutamol, salinosporamide A, salmeterol, saxitoxin, Scopolamine, SH5, SH23, SH24, SH25, shepherdin, SLF-CR, SM102-SM130, SMAC/DIABLO, sorafenib, SP4206, Sparsomycin, Sphingomyelin, SQ22536, STATTIC, Ste-MPKKKPTPIQLNP-NH2 (SEQ ID NO: 1), streptogramins, suberoylanilide hydroxamic acid, substituted 3-(2-indolyl)piperidines, sunitinib, survivin, Tamoxifen, tautomycin, temsirolimus, terbutaline, tetracyclins, tetra-ubiquitin, tetrodotoxin, TGFa, TIJIP, TNFR, trans-4-Iodo,4'-boranyl-chalcone, trichostatin A, tri-ubiquitin, tubulin, U0126, Variolin, veratridine, VPPPVPPRRR (SEQ ID NO: 9), ZD9331, Zeranol, Z-VAD(OMe)-FMK, Z-VAD-CHO, ω-agatoxins, and ω-conotoxin.

* * * * *